United States Patent
Jean et al.

(10) Patent No.: US 9,656,984 B2
(45) Date of Patent: May 23, 2017

(54) PI3K/AKT/MTOR INHIBITORS AND PHARMACEUTICAL USES THEREOF

(71) Applicants: UNIVERSITE DE RENNES 1, Rennes (FR); Centre national de la recherche scientifique, Paris (FR); INSTITUT NATIONAL DE LA SANTE ET DE LA RECHERCHE MEDICALE (INSERM), Paris (FR)

(72) Inventors: Mickael Jean, Lamballe (FR); Amélie Fouque, Neufbosc (FR); Patrick Legembre, Rennes (FR); Pierre Van De Weghe, Rennes (FR)

(73) Assignees: UNIVERSITE DE RENNES 1, Rennes (FR); CENTRE NATIONAL DE LA RECHERCHE SCIENTIFIQUE, Paris (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 0 days.

(21) Appl. No.: 15/025,086

(22) PCT Filed: Sep. 24, 2014

(86) PCT No.: PCT/EP2014/070409
§ 371 (c)(1),
(2) Date: Mar. 25, 2016

(87) PCT Pub. No.: WO2015/044229
PCT Pub. Date: Apr. 2, 2015

(65) Prior Publication Data
US 2016/0244424 A1    Aug. 25, 2016

(30) Foreign Application Priority Data

Sep. 25, 2013    (EP) .................... 13306312

(51) Int. Cl.
| | |
|---|---|
| *C07D 311/60* | (2006.01) |
| *C07D 335/06* | (2006.01) |
| *C07D 407/04* | (2006.01) |
| *C07D 495/04* | (2006.01) |
| *C07D 493/10* | (2006.01) |
| *C07D 409/04* | (2006.01) |
| *C07D 311/64* | (2006.01) |

(52) U.S. Cl.
CPC .......... *C07D 311/60* (2013.01); *C07D 311/64* (2013.01); *C07D 335/06* (2013.01); *C07D 407/04* (2013.01); *C07D 409/04* (2013.01); *C07D 493/10* (2013.01); *C07D 495/04* (2013.01)

(58) Field of Classification Search
None
See application file for complete search history.

(56) References Cited

U.S. PATENT DOCUMENTS 5,763,470 A * 6/1998 Tang .................... A61K 31/352
514/406

FOREIGN PATENT DOCUMENTS

| WO | 9640110 A1 | 12/1996 |
|---|---|---|
| WO | 2010009069 A1 | 1/2010 |

OTHER PUBLICATIONS

Pollizzi, et al.: Equivalent benefit of mTORCI blockade and combined PI3K-mTOR blockade in a mouse model of tuberous sclerosis, Molecular Cancer, Biomed Central Ltd., 8:38, doi:10.1186/1476-4598-8-38, Jun. 15, 2009 (Jun. 15, 2009), pp. 1-9.

Bowman: "Bioactive Compound Synthetic Capacity and Ecological Significance of Marine Bacterial Genus *Pseudoalteromonas*", Marine Drugs, vol. 5, No. 4, Dec. 18, 2007 (Dec. 18, 2007), pp. 220-241.

Mao, et al.: "A small-molecule inhibitor of D-cyclin transactivation displays preclinical efficacy in myeloma and leukemia via phosphoinositide 3-kinase pathway", Blood Journal, Hemotology Library, vol. 117, No. 6, doi:10.1182/blood-2010-05-284810, Feb. 10, 2011 (Feb. 10, 2011), 13 pages.

Yin, et al.: "Preparation of S14161 and its analogues and the discovery of 6-bromo-8-ethoxy-3-nitro-2H-chromene as a more potent antitumor agent in vitro", Bioorganic & Medicinal Chemistry Letters, Mar. 23, 2013 (Mar. 23, 2013), pp. 3314-3319.

* cited by examiner

*Primary Examiner* — Timothy R Rozof
(74) *Attorney, Agent, or Firm* — Troutman Sanders LLP

(57) ABSTRACT

The invention relates to new PI3K/AKT/m TOR inhibitors and their use for the prevention and/or the treatment of a disease selected from the group consisting of: inflammatory diseases, autoimmune diseases, neurodegenerative diseases, cancers, transplant rejection, diseases characterized by a premature aging and tuberous sclerosis.

14 Claims, 14 Drawing Sheets

PI3K/AKT/MTOR INHIBITORS AND PHARMACEUTICAL USES THEREOF

CROSS-REFERENCE TO RELATED APPLICATIONS

This application is the U.S. National Phase of International Patent Application Serial No. PCT/EP2014/070409, filed Sep. 24, 2014, which claims priority to European Patent Application No. 13306312.3, filed Sep. 25, 2013, both of which are herein incorporated by reference in their entireties.

FIELD OF THE INVENTION

The present invention concerns new PI3K/AKT/mTOR inhibitors, their preparation methods and their pharmaceutical uses.

BACKGROUND

Phosphoinositide 3-kinases (also called Phosphatidylinositol 3-kinases or PI3Ks) constitute a family of lipid kinase enzymes that control a range of cellular processes through their regulation of a network of signal transduction pathways, and have emerged as important therapeutic targets in the context of cancer, inflammation and cardiovascular diseases.

PI3Ks are divided into three different classes: Class I, II and III. Class I PI3Ks are intracellular signal transducer enzymes capable of phosphorylating the phosphatidylinositol-4,5-diphosphate (PIP2) to form the phosphatidylinositol-3,4,5-triphosphate (PIP3). The formation of PIP3 plays a role in the PI3K-dependent activation of the PI3K/AKT/mTOR pathway.

Since PIP3 is restricted to the plasma membrane, it allows the recruitment of AKT and PDK1 (PDK1 or Phosphoinositide-Dependent Protein Kinase 1) to the plasma membrane. The colocalization of activated PDK1 and AKT allows AKT to become phosphorylated by PDK1 on threonine 308, leading to partial activation of AKT. AKT (also known as PKB, Protein Kinase B) is a serine/threonine protein kinase that regulates cellular survival and metabolism by binding and regulating many downstream effectors.

Full activation of AKT occurs upon phosphorylation of serine 473 by the TORC2 complex comprising the mTOR protein kinase (the mammalian target of rapamycin). mTOR is a key protein kinase that regulates cell growth and metabolism to maintain cellular and organismal homeostasis. mTOR is expressed ubiquitously and constitutively. It is found in two complexes: mTOR complexe 1 (mTORC1 or mTOR/raptor) which plays a role in the regulation of translation and cell growth and mTOR complexe 2 (mTORC2 or mTOR/rictor) which regulates several substrates, among them AKT.

The PI3K/AKT/mTOR signaling pathway has been shown to be required for an extremely diverse array of cellular activities, such as cell growth, proliferation, differentiation, motility, survival and intracellular trafficking. The inhibition of the PI3K/AKT/mTOR pathway may thus have a particularly interest in the prevention and/or treatment of benign or malignant tumors, diabetes, age-related disorders, auto-immune disorders and transplant rejection (Don Benjamin et al. Nature Reviews Drug Discovery, 868, November 2011, vol. 10). It has also been shown that PI3K/AKT/mTOR inhibition implements aggregation and activation of death receptors in tumor cells (Beneteau, M. et al. Localization of Fas/CD95 into the lipid rafts on down-modulation of the phosphatidylinositol 3-kinase signaling pathway. *Molecular cancer research: MCR* 6, 604-613, (2008); Pizon, M. et al. Actin-independent exclusion of CD95 by PI3K/AKT signalling: Implications for apoptosis. *European journal of immunology* 41, (2011)).

Therefore, PI3K/AKT/mTOR inhibitors are a promising target for drug development, in particular in the prevention and/or the treatment of benign and/or malignant tumors. There is thus a need to provide new PI3K/AKT/mTOR inhibitors.

SUMMARY

The aim of the present invention is to provide new inhibitors of the PI3K/AKT/mTOR pathway, and more specifically mTOR inhibitors. In one embodiment, the compounds of the invention may be competitive inhibitors of mTOR. Another aim of the present invention is to provide new PI3K/AKT/mTOR pathway inhibitors, which demonstrate a cytotoxic effect in tumor cells, for the prevention and/or the treatment of tumors, such as benign and/or malignant tumors.

Another aim of the present invention is to provide new PI3K/AKT/mTOR pathway inhibitors, which prevent migration of tumor cells, for the prevention and/or the treatment of tumors, in particular metastasis.

The present invention thus relates to a compound having the formula (I):

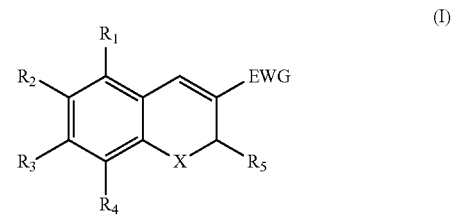

wherein:
X is O or S;
$R_1$, $R_2$, $R_3$ and $R_4$ are independently chosen from the group consisting of: H, $(C_1-C_{10})$alkyl, $(C_1-C_{10})$alkoxyl, $(C_2-C_{10})$alkenyl, $(C_2-C_{10})$alkynyl, OH, a fluorine atom, a bromine atom, a iodine atom, $O(C_1-C_{10})$alkylene-NHCO$(C_1-C_{10})$alkylene-$(C_5-C_{10})$heterocycloalkyl and $O(C_1-C_{10})$alkylene-NH—CS—NH—R" with R" being:

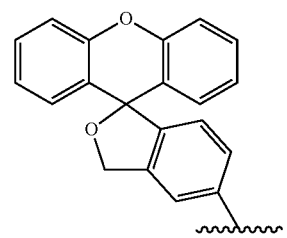

wherein:
$R_2$ and $R_3$ may form together with the carbon atoms carrying them a $(C_6-C_{10})$aryl group; and
R" and the $(C_5-C_{10})$heterocycloalkyl are optionally substituted by at least one substituent selected from OH and =O;

EWG is chosen from the group consisting of:

NO₂, CHO, COR, CN, CN—OH, CONHR, CONRR' and COOR; R and R' being independently from each other chosen from (C₁-C₁₀)alkyl groups;

R₅ is a (C₆-C₁₀)aryl, a (C₅-C₁₀)heteroaryl group, a (C₃-C₁₀)cycloalkyl or a (C₃-C₁₀)heterocycloalkyl group; said aryl and heteroaryl being optionally substituted by at least one substituent independently chosen from halogen, (C₁-C₁₀)alkoxyl and nitro;

R₅ being different from the group:

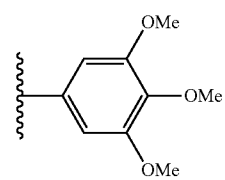 [SMILES: *c1cc(OC)c(OC)c(OC)c1]

and wherein when EWG is COOMe, one of R₁, R₂, R₃ or R₄ is different from H; and provided that the compound of formula (I) is not one of the following compounds:

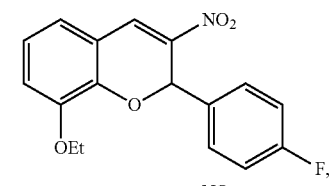

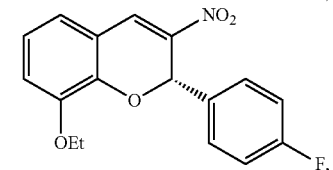

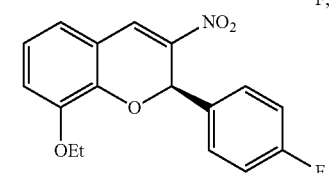

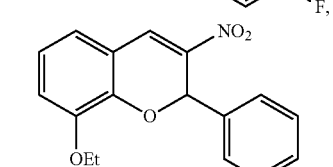

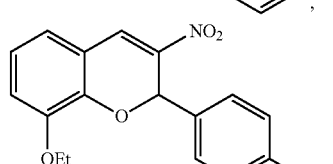

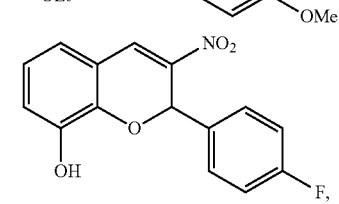

-continued

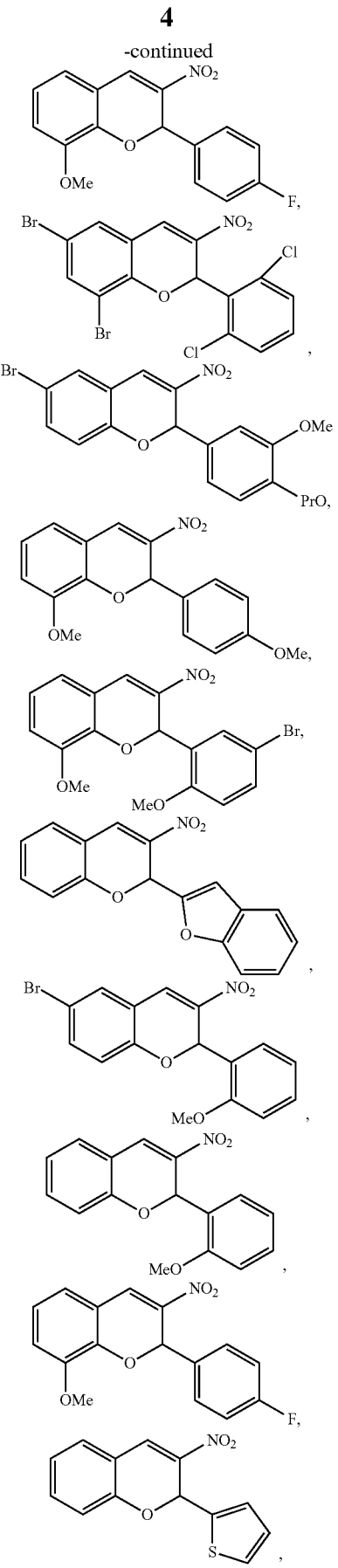

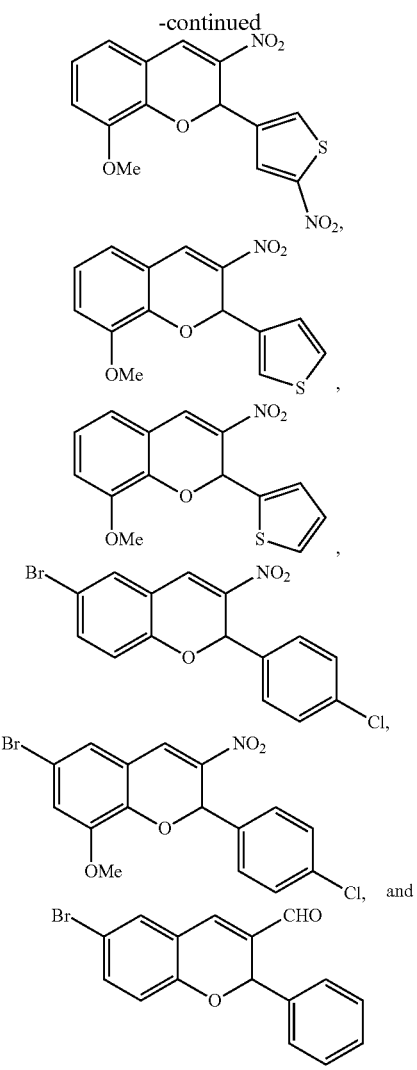

or its pharmaceutically acceptable salts, hydrates or hydrated salts or its polymorphic crystalline structures, racemates, diastereomers or enantiomers.

Document CN 101849934 describes a PI3K inhibitor (also called compound A), of formula:

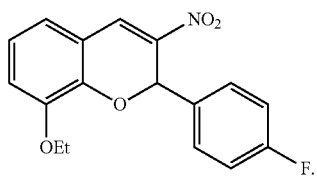

(A)

This compound has been tested according to the same biological tests than the compounds of the invention, as described below.

The compounds of formula (I) are inhibitors of the PI3K/AKT/mTOR pathway. In a particular embodiment, they are mTOR inhibitors.

These molecules inhibit the PI3K/AKT/mTOR pathway and are more potent than the above mentioned compound A and the well-known PI3K inhibitor LY294002.

Even more surprisingly, the new PI3K/AKT/mTOR inhibitors also show an increased cytototoxic effect on tumoral cells.

The term "$(C_1-C_{10})$alkyl" means a saturated aliphatic hydrocarbon group which may be straight or branched having 1 to 10 carbon atoms in the chain. Preferred alkyl groups have 1 to 4 carbon atoms in the chain, preferred alkyl groups are in particular methyl or ethyl groups. "Branched" means that one or lower alkyl groups such as methyl, ethyl or propyl are attached to a linear alkyl chain.

The term "$(C_1-C_{10})$alkylene" means a saturated aliphatic hydrocarbon divalent radical which may be straight or branched having 1 to 10 carbon atoms in the chain. Preferred alkylene groups may have 3, 4, 5 or 6 carbon atoms.

By "$(C_3-C_{10})$cycloalkyl" is meant a cyclic, saturated hydrocarbon group having 3 to 10 carbon atoms, in particular cyclopropyl or cyclohexyl groups.

By "$(C_2-C_{10})$alkenyl" is meant an unsaturated alkyl, comprising at least one double bond between two carbon atoms and comprising from 2 to 10 carbon atoms, preferably from 2 to 4 carbon atoms.

By "$(C_2-C_{10})$alkynyl" is meant an unsaturated alkyl, comprising at least one triple bond between two carbon atoms and comprising from 2 to 10 carbon atoms, preferably from 2 to 4 carbon atoms, more preferably 2 carbon atoms.

The term "$(C_1-C_{10})$alkoxy" refers to an alkyl-O— group wherein the alkyl is defined above. Preferred alkoxy groups are methoxy or ethoxy groups.

The term "$(C_6-C_{10})$aryl" refers to an aromatic monocyclic, bicyclic, or tricyclic hydrocarbon ring system wherein any ring atom capable of substitution may be substituted by a substituent. Examples of aryl moieties include, but are not limited to, phenyl.

The term "$(C_5-C_{10})$heteroaryl" refers to an aromatic monocyclic, bicyclic, or tricyclic hydrocarbon ring system, wherein any ring atom capable of substitution may be substituted by a substituent and wherein one or more carbon atom(s) are replaced by one or more heteroatom(s) such as nitrogen atom(s), oxygen atom(s) and sulphide atom(s); for example 1 or 2 nitrogen atom(s), 1 or 2 oxygen atom(s), 1 or 2 sulphide atom(s) or a combination of different heteroatoms.

The term "heterocycloalkyl" refers to a mono- or bicyclic alkyl group wherein one or more carbon atom(s) are replaced by one or more heteroatom(s) such as nitrogen atom(s), oxygen atom(s) and sulphide atom(s); for example 1 or 2 nitrogen atom(s), 1 or 2 oxygen atom(s), 1 or 2 sulphide atom(s) or a combination of different heteroatoms such as one sulphide atom and two nitrogen atoms. Examples of heterocycloalkyl moieties include, but are not limited to, tetrahydropyranyl or hexahydro-thieno[3,4-d]imidazole.

The term "halogen" refers to the atoms of the group 17 of the periodic table and includes in particular fluorine, chlorine, bromine, and iodine atoms, more preferably fluorine, chlorine and bromine atoms.

The compounds herein described may have asymmetric centers. Compounds of the present invention containing an asymmetrically substituted atom may be isolated in optically active or racemic forms. It is well-known in the art how to prepare optically active forms, such as by resolution of racemic forms or by synthesis from optically active starting materials. All chiral, diastereomeric, racemic forms and all geometric isomeric forms of a compound are intended, unless the stereochemistry or the isomeric form is specifically indicated. In one embodiment, the compounds of formula (I) are in the R enantiomeric form. In another embodiment, the compounds of formula (I) are in the S enantiomeric form.

The term "pharmaceutically acceptable salt" refers to salts which retain the biological effectiveness and properties of the compounds of the invention and which are not biologically or otherwise undesirable. Pharmaceutically acceptable acid addition salts may be prepared from inorganic and organic acids, while pharmaceutically acceptable base addition salts can be prepared from inorganic and organic bases. For a review of pharmaceutically acceptable salts see Berge, et al. ((1977) J. Pharm. Sd, vol. 66, 1). For example, the salts include those derived from inorganic acids such as hydrochloric, hydrobromic, sulfuric, sulfamic, phosphoric, nitric, and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, fumaric, methanesulfonic, and toluenesulfonic acid and the like.

In a particular embodiment, in formula (I) as defined above, EWG is chosen from the group consisting of: $NO_2$, CHO, COOR, CN, CN—OH and CONRR', R and R' being defined above. More particularly, EWG is chosen from $NO_2$, CHO, COOMe, CN, CN—OH and $CONMe_2$. More particularly, EWG is $NO_2$ or CHO.

In a particular embodiment, $R_1$ is H.

In a particular embodiment, $R_2$ is H, $(C_2\text{-}C_{10})$alkynyl, Br, F, I, OH, $O(C_1\text{-}C_{10})$alkylene-NHCO$(C_1\text{-}C_{10})$alkylene-$(C_5\text{-}C_{10})$heterocycloalkyl or $O(C_1\text{-}C_{10})$alkylene-NH—CS—NH—R" with R" being:

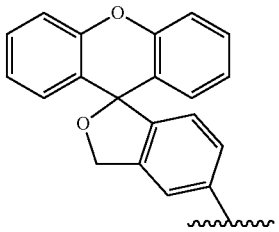

wherein:
R" and the $(C_5\text{-}C_{10})$heterocycloalkyl group are optionally substituted by OH or ═O;
or $R_2$ forms with $R_3$ together with the carbon atoms carrying them a $(C_6\text{-}C_{10})$aryl group.

In one embodiment, $R_2$ is H, $(C_2\text{-}C_4)$alkynyl, Br, F, OH, $O(C_1\text{-}C_5)$alkylene-NHCO$(C_1\text{-}C_5)$alkylene-$(C_5)$heterocycloalkyl or $O(C_1\text{-}C_7)$alkylene-NH—CS—NH—R" with R" being:

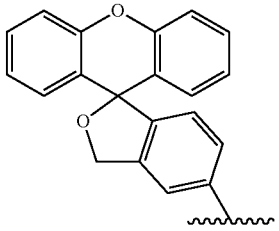

wherein:
R" and the $(C_5)$heterocycloalkyl group are optionally substituted by at least one substituent selected from OH or ═O;

or $R_2$ forms with $R_3$ together with the carbon atoms carrying them a phenyl group.

In a particular embodiment, said $(C_5)$heterocycloalkyl is a hexahydro-thieno[3,4-d]imidazole. In another embodiment, $R_2$ is chosen among H, Br, OH, $C_2$-alkynyl,

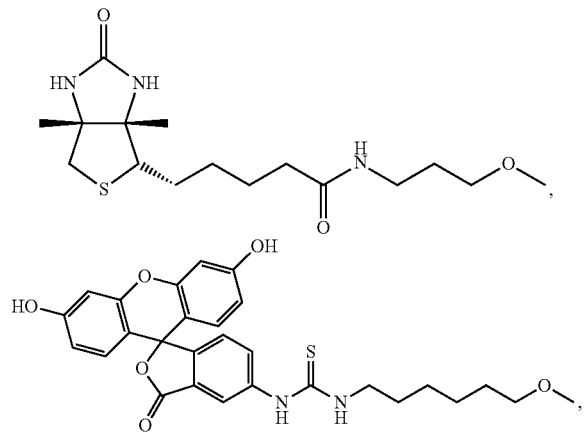

or $R_2$ forms with $R_3$ together with the carbon atoms carrying them a phenyl group.

In another embodiment, $R_2$ may be chosen among H, Br, OH, $C_2$-alkynyl or $R_2$ forms with $R_3$ together with the carbon atoms carrying them a phenyl group.

In a particular embodiment, $R_3$ is H, $(C_1\text{-}C_{10})$alkoxyl or forms together with $R_2$ and the carbon atoms carrying them a $(C_6\text{-}C_{10})$aryl. More particularly, $R_3$ is H, $(C_1\text{-}C_3)$alkoxyl such as $OCH_3$, or forms together with $R_2$ and the carbon atoms carrying them a phenyl group.

In one embodiment, $R_4$ is H, halogen or $(C_1\text{-}C_{10})$alkoxyl. In another embodiment, $R_4$ is H, Br, Cl, F or $(C_1\text{-}C_3)$alkoxyl. More particularly, $R_4$ is H, $OCH_3$, $OC_2H_5$ or Br.

In a particular embodiment, $R_5$ is a possibly substituted $(C_6\text{-}C_{10})$aryl or a $(C_3\text{-}C_{10})$heterocycloalkyl. In another embodiment, $R_5$ is a possibly substituted phenyl or a tetrahydropyranyl group.

In a particular embodiment, $R_5$ is a phenyl group, substituted with at least one substituent chosen from the group consisting of: halogen, nitro, and $(C_1\text{-}C_4)$alkoxyl.

Preferably $R_5$ is a phenyl group, substituted with at least one substituent chosen from the group consisting of: F, Br, Cl, $NO_2$ and $OCH_3$. In a particular embodiment, $R_5$ is a phenyl group optionally substituted by F, Br, Cl or $NO_2$. In a particular embodiment, $R_5$ is a phenyl substituted in para position. In one embodiment $R_5$ is not a thiophene group or a benzofurane.

In a particular embodiment, X is O. In a particular embodiment, X is S.

In a particular embodiment, EWG is $NO_2$, CHO, COOMe, CN, CN—OH or $CONMe_2$ and X is O. In a particular embodiment, EWG is $NO_2$ and X is S.

In another particular embodiment, $R_1$ and $R_3$ are H, EWG is $NO_2$, CHO, COOMe, CN, CN—OH or $CONMe_2$ and X is O.

In a particular embodiment, EWG is $NO_2$, CHO, COOMe, CN, CN—OH or $CONMe_2$, X is O and $R_5$ is a possibly substituted phenyl or a tetrahydropyranyl group.

In a particular embodiment, EWG is $NO_2$, CHO, COOMe, CN, CN—OH or $CONMe_2$, X is O, $R_5$ is a possibly substituted phenyl or a tetrahydropyranyl group and $R_4$ is chosen from H, $OCH_3$, $OC_2H_5$ or Br.

In a particular embodiment, $R_2$ forms together with $R_3$ and with the carbon atoms carrying them a phenyl group, EWG is $NO_2$ and $R_4$ is H.

In a particular embodiment, $R_1$, $R_2$ and $R_3$ are H. In another particular embodiment, $R_1$ and $R_3$ are H and $R_2$ is Br. In another particular embodiment, $R_1$ and $R_3$ are H and $R_2$ and $R_4$ are Br.

The above mentioned particular embodiments can be combined with each other.

In another embodiment, the compounds according to the invention have the following formula (a):

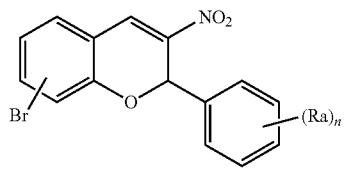

(a)

wherein Ra is the same or different and is chosen from F, Br, Cl or $NO_2$; and n is 1 or 3.

In a particular embodiment, the compounds according to the invention have the following formula (b):

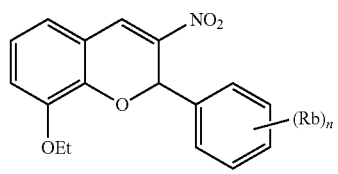

(b)

wherein Rb is the same or different and chosen from Br, Cl or $NO_2$; and n is 1 or 3.

In a particular embodiment, the compounds according to the invention have the following formula (c):

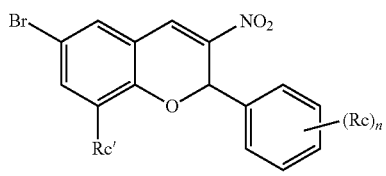

(c)

wherein Rc is the same or different and chosen from F, Br, Cl or $NO_2$;
Rc' is Br or OMe; and n is 1 or 3.

In a particular embodiment, the compounds according to the invention have the following formula (d):

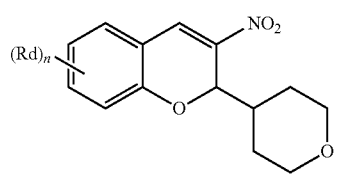

(d)

wherein Rd is the same or different and chosen from Br or OMe and n is 1 or 2.

In a particular embodiment, the compounds according to the invention have the following formula (e):

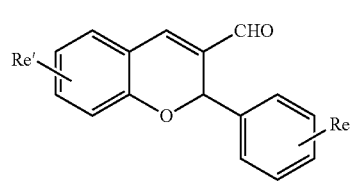

(e)

wherein Re is H, Br or F and Re' is Br or OEt.

In a particular embodiment, the compounds according to the invention have the following formula (f):

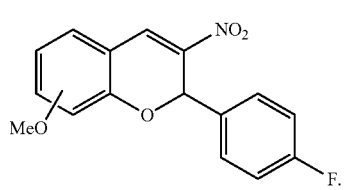

(f)

In a particular embodiment, the compounds according to the invention have the following formula (g):

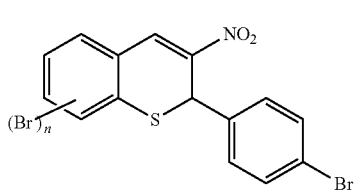

(g)

wherein n is 1 or 2.

In a particular embodiment, the compounds according to the invention have the following formula (h):

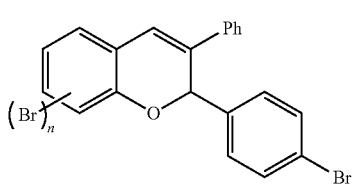

(h)

wherein Rh is chosen from the group consisting of COOMe, $CONMe_2$, CNOH, and CN, and wherein n is 1 or 2.

In a particular embodiment, the compounds according to the invention have the following formula (i):

(i) 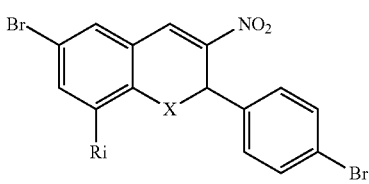

wherein X is O or S and Ri is selected from the group consisting of H, $(C_1-C_{10})$alkyl, $(C_1-C_{10})$alkoxyl, $(C_2-C_{10})$alkenyl, $(C_2-C_{10})$alkynyl, OH, a fluorine atom, a bromine atom and a iodine atom.

Preferably, Ri is selected from the group consisting of H, a fluorine atom, a bromine atom or a iodine atom and more preferably, Ri is H or Br.

Some specific compounds of the invention have one of the following formulae:

2
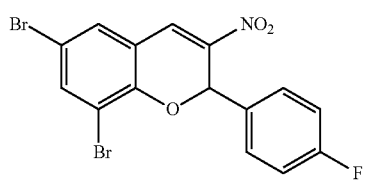

3
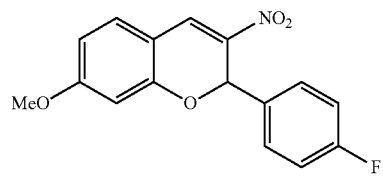

5
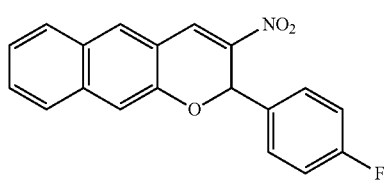

6
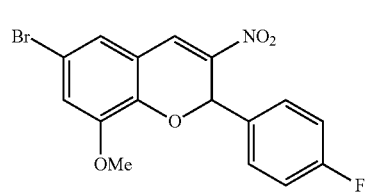

7
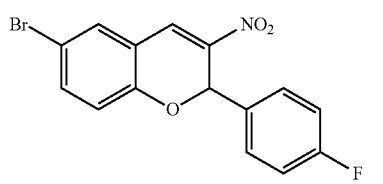

8
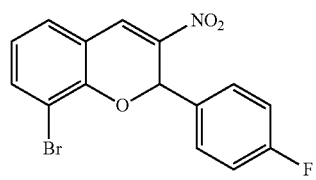

9
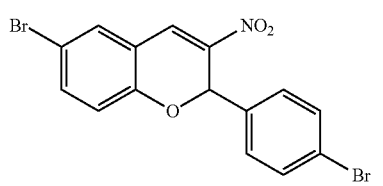

11
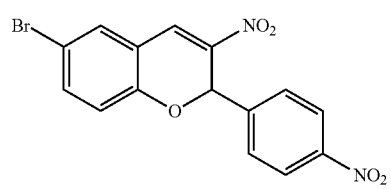

13
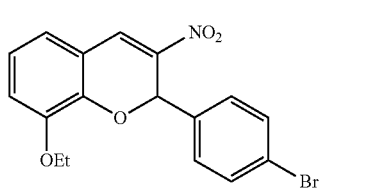

14
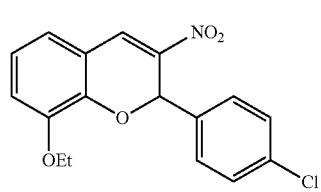

15
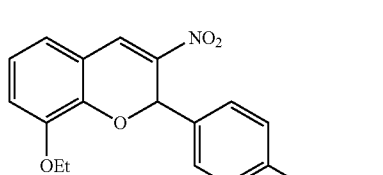

16
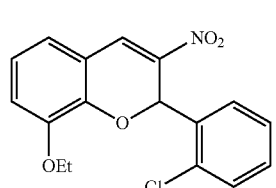

18
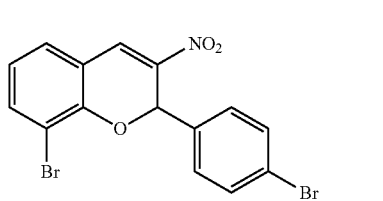

19
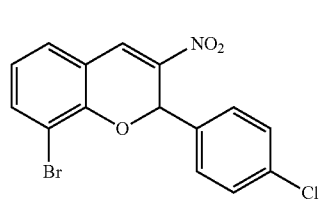

-continued
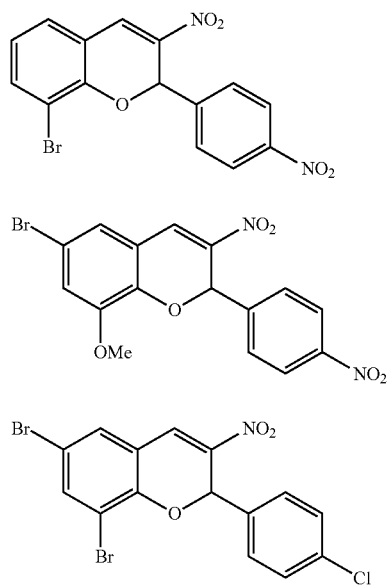
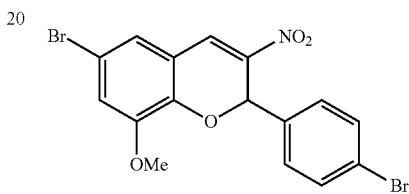
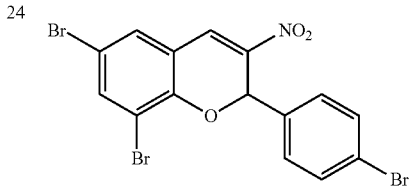
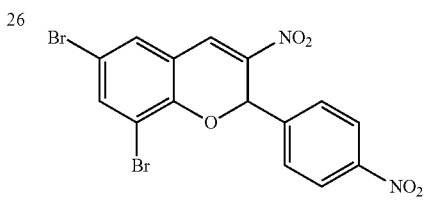
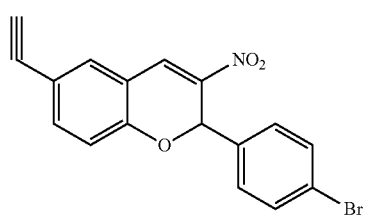
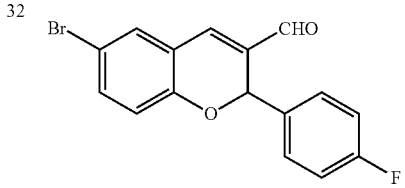
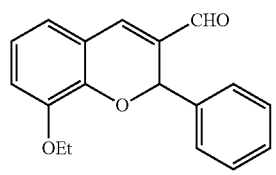
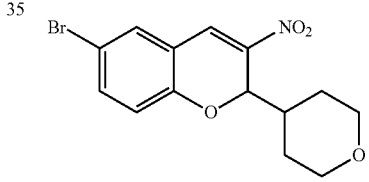
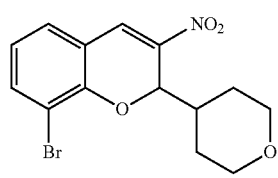
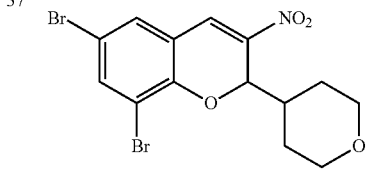
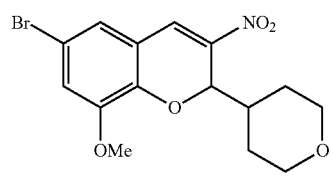
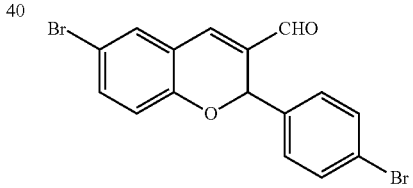
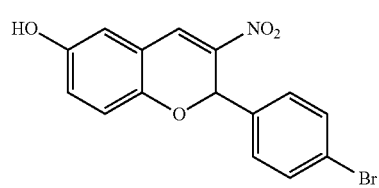

-continued
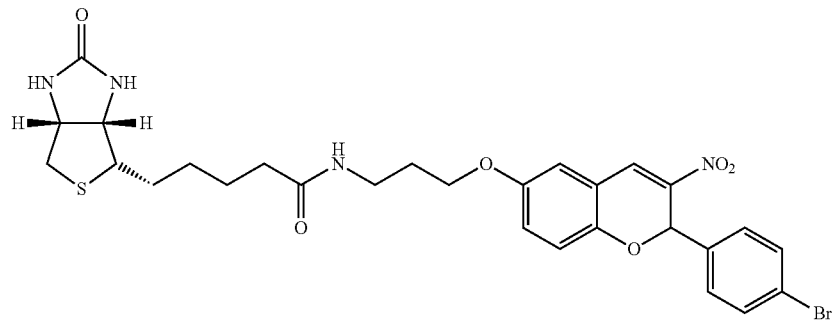
47
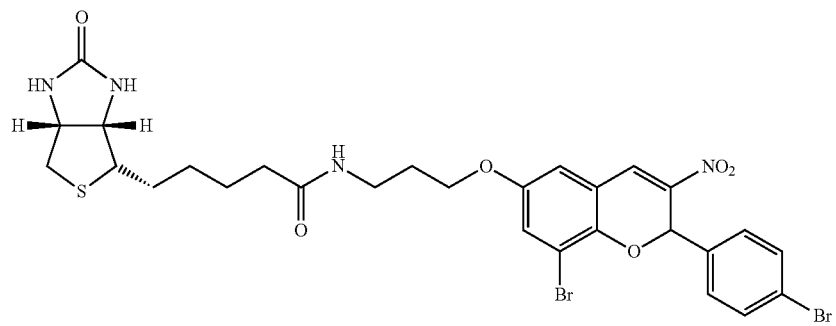
48
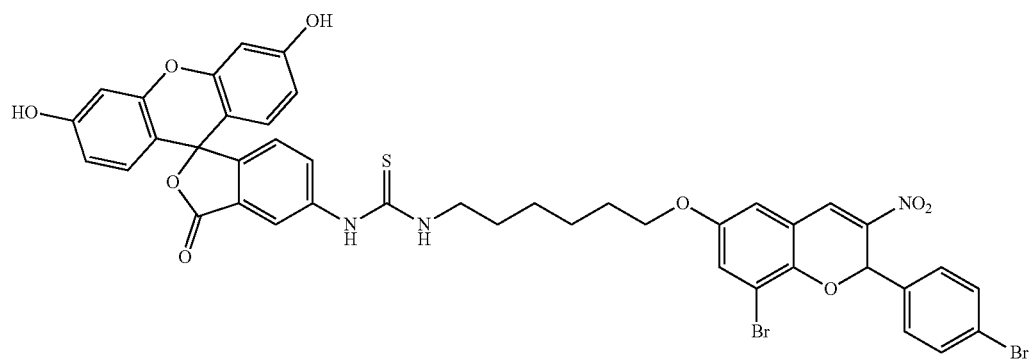
49
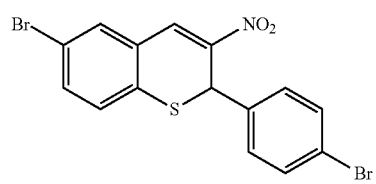
50
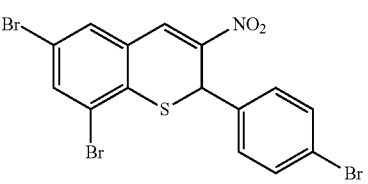
51
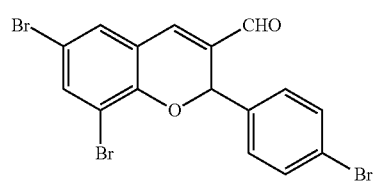
52
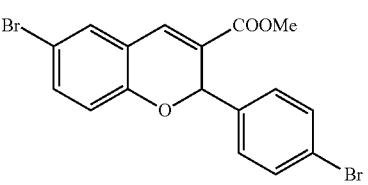
55
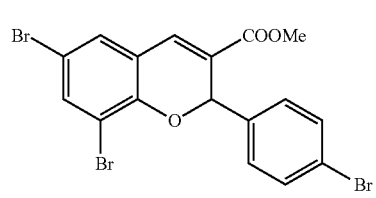
56
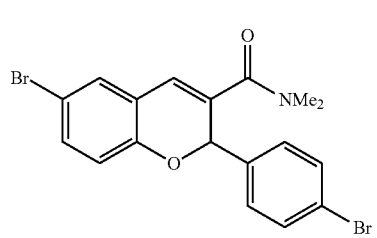
57

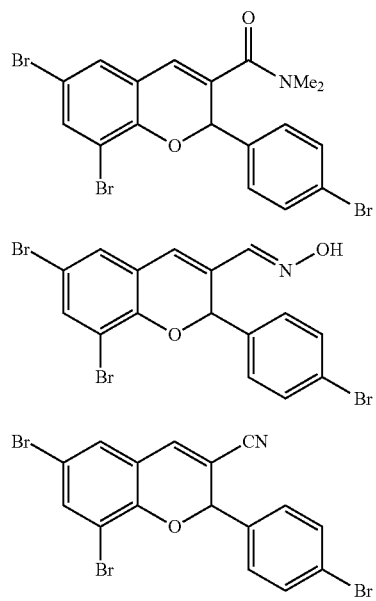
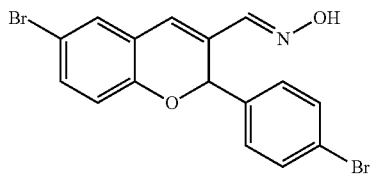
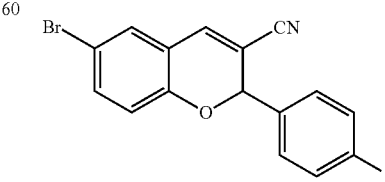
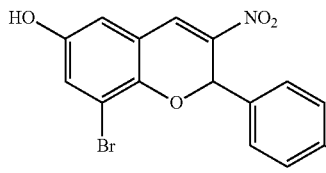

Preferably, some specific compounds of the invention have one of the following formulae:

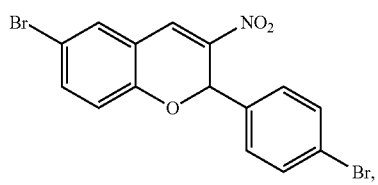
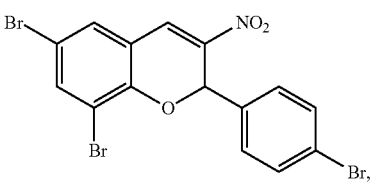
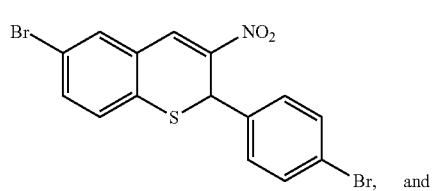
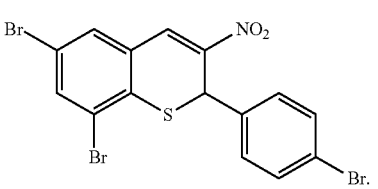

In one particular embodiment, the compound of formula (I) is:

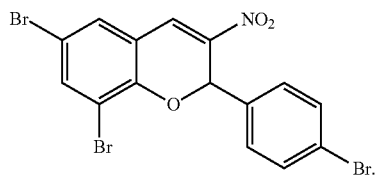

In a particular embodiment, the compound of formula (I) is:

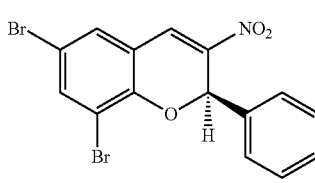

or

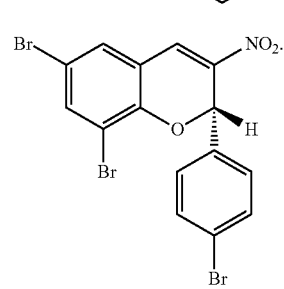

The invention also relates to the compound of formula (I) defined above, for its use for the prevention and/or the treatment of a disease selected from the group consisting of: inflammatory diseases, autoimmune diseases, neurodegenerative diseases, cancers, transplant rejection, diseases characterized by a premature aging, and tuberous sclerosis.

The invention also relates to a compound having formula (I):

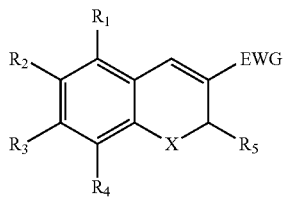

(I)

wherein X, $R_1$, $R_2$, $R_3$, $R_4$, $R_5$ and EWG are defined as above provided that the compound of formula (I) is not one of the following compounds:

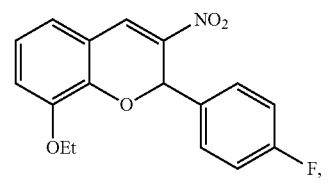

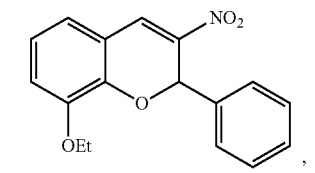

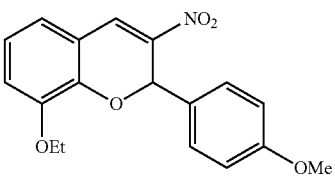

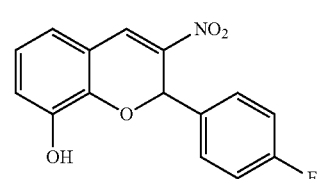

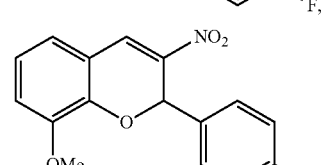

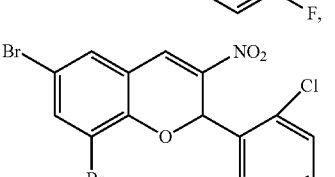

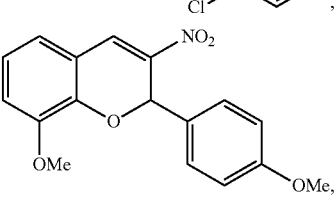

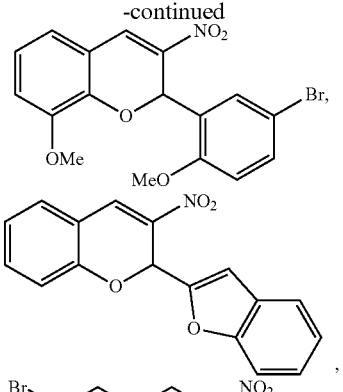

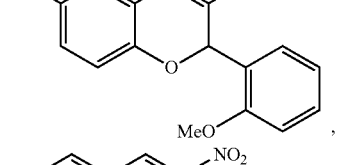

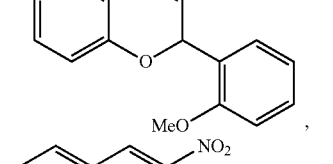

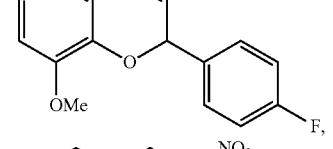

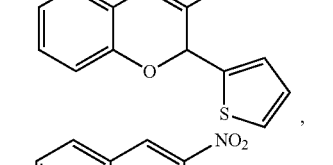

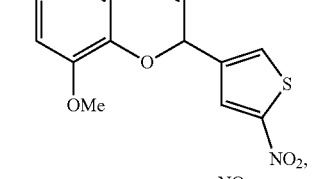

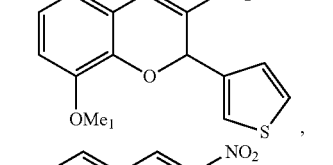

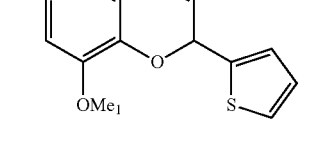

or its pharmaceutically acceptable salts, hydrates or hydrated salts or its polymorphic crystalline structures, racemates, diastereomers or enantiomers, for use for the prevention and/or the treatment of a disease selected from the group consisting of: inflammatory diseases, autoimmune diseases, neurodegenerative diseases, cancers, transplant rejection, diseases characterized by a premature aging, and tuberous sclerosis.

The present invention also relates to a compound having formula (I):

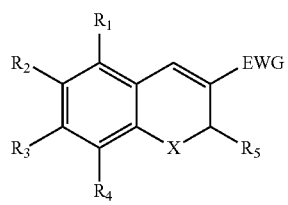

wherein X, $R_1$, $R_2$, $R_3$, $R_4$, $R_5$ and EWG are defined as above, and provided that the compound of formula (I) is not:

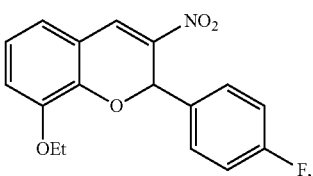

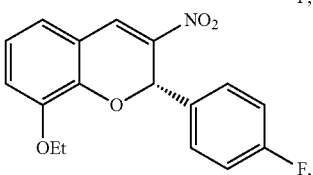

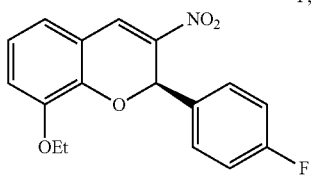

or its pharmaceutically acceptable salts, hydrates or hydrated salts or its polymorphic crystalline structures, racemates, diastereomers or enantiomers, for use for the prevention and/or the treatment of a disease selected from the group consisting of: inflammatory diseases, autoimmune diseases, neurodegenerative diseases, cancers, transplant rejection, diseases characterized by a premature aging and tuberous sclerosis, more particularly for the prevention and/or the treatment of tuberous sclerosis.

The invention also relates to a compound having formula (I):

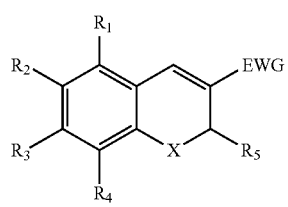

wherein X, $R_1$, $R_2$, $R_3$, $R_4$, $R_5$ and EWG are defined as above provided that the compound of formula (I) is not one of the following compounds:

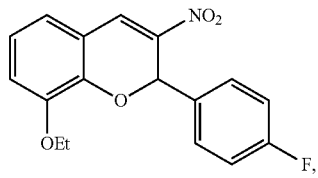

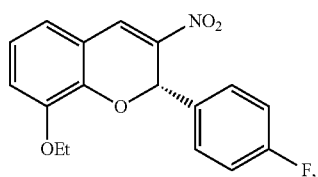

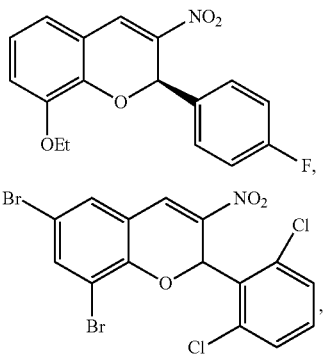

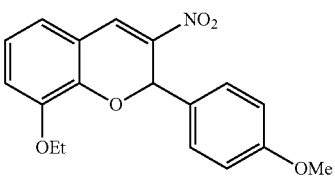

or its pharmaceutically acceptable salts, hydrates or hydrated salts or its polymorphic crystalline structures, racemates, diastereomers or enantiomers, for use for the prevention and/or the treatment of a disease selected from the group consisting of: autoimmune diseases, diseases characterized by a premature aging, and tuberous sclerosis.

In one embodiment, the following compounds are intended for the use as defined above.

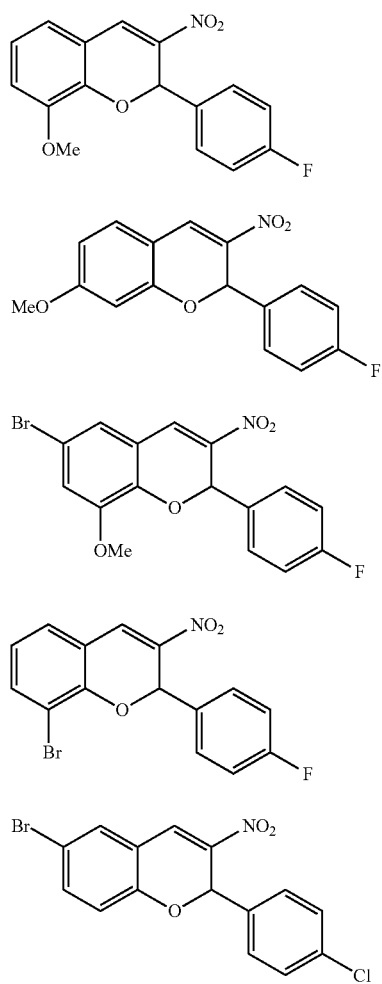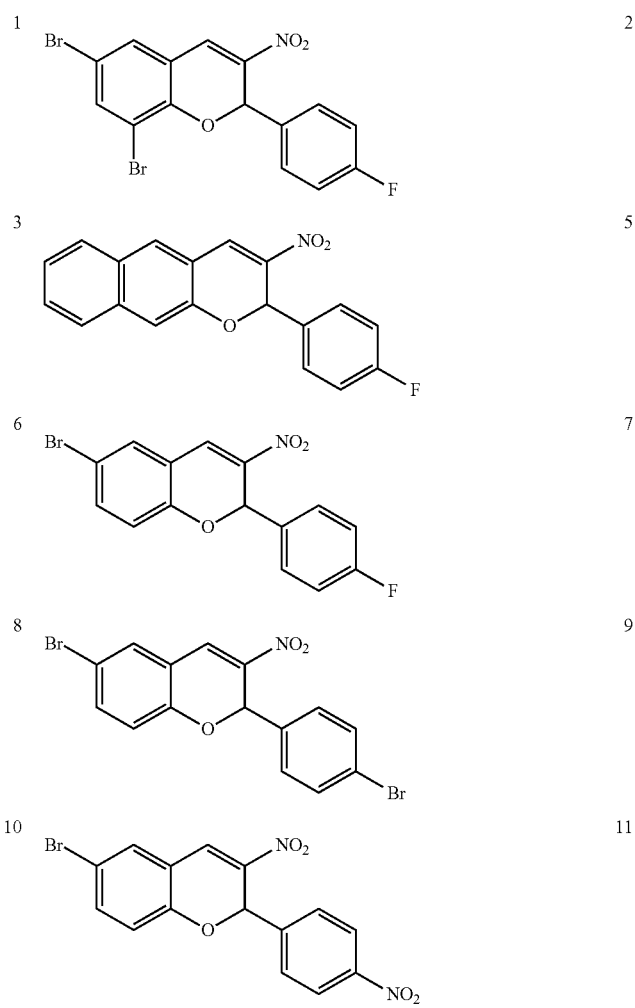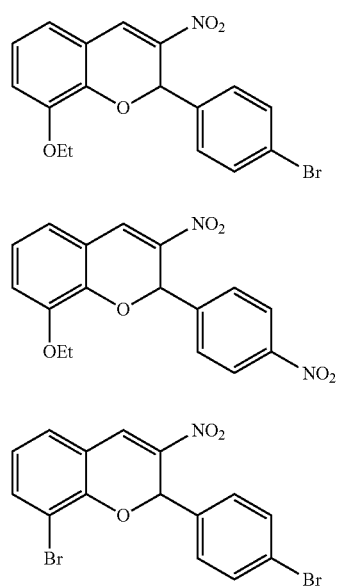

-continued
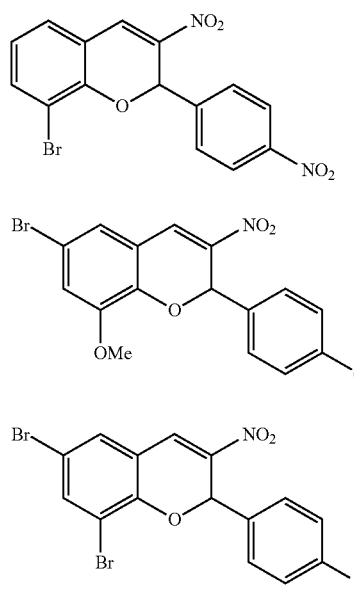
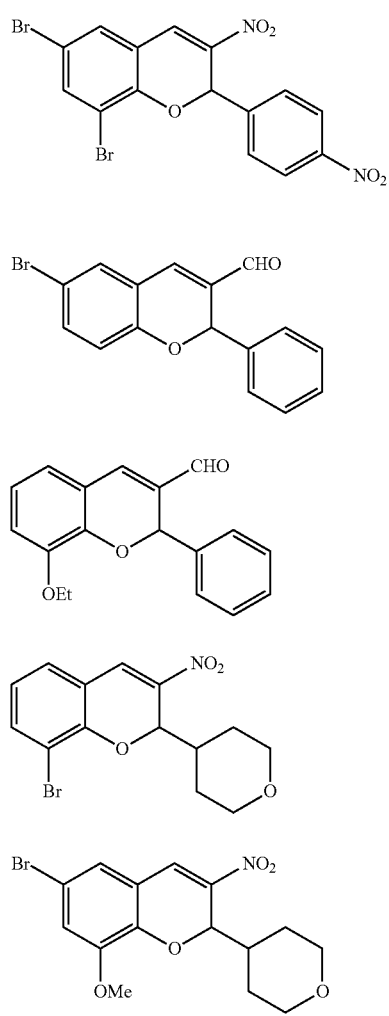
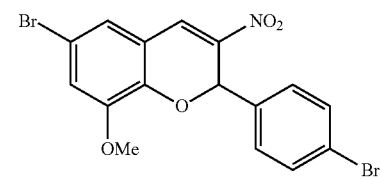
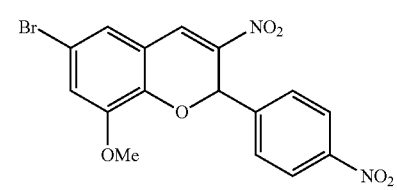
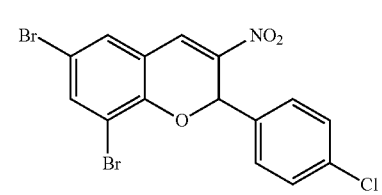
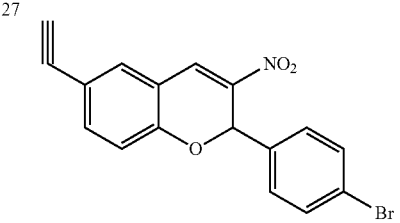
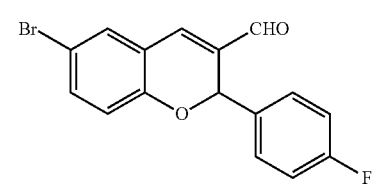
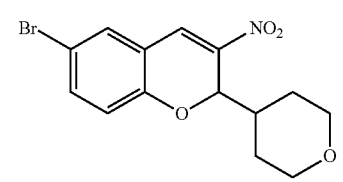
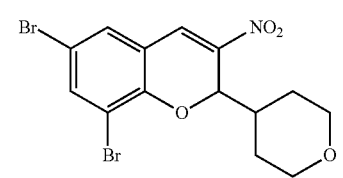
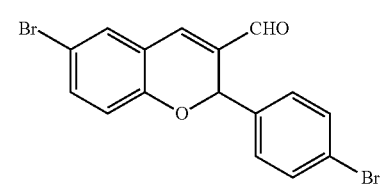

-continued
45
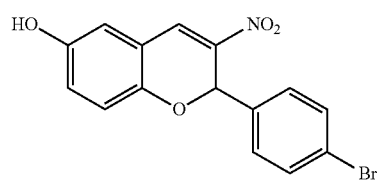
47
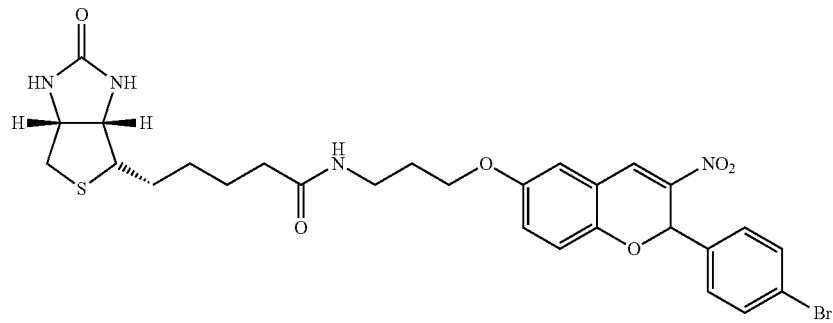
48
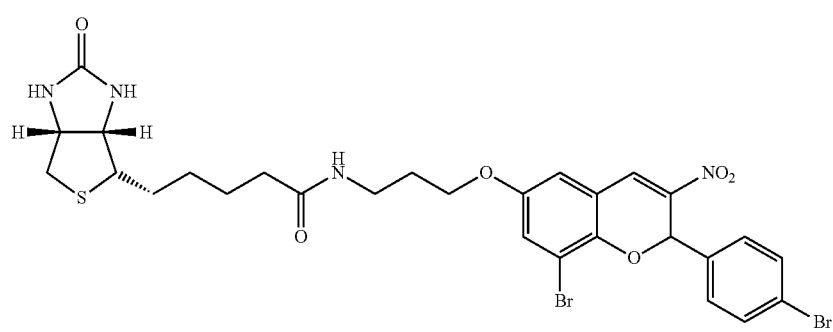
49
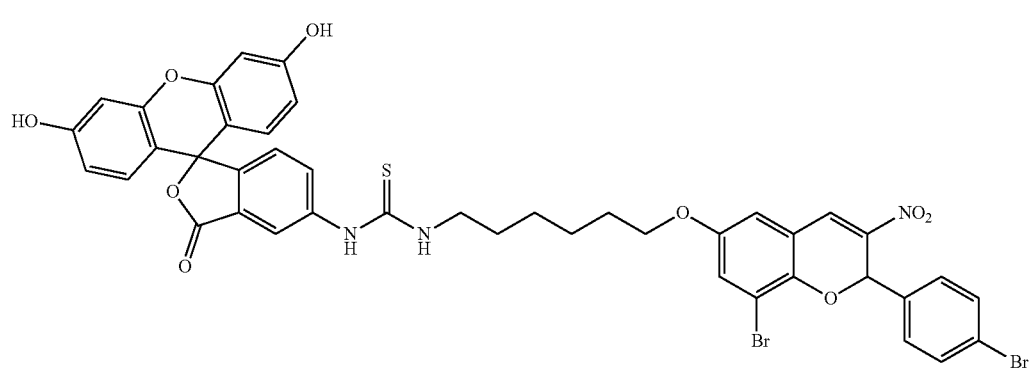
50
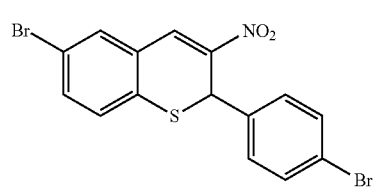
51
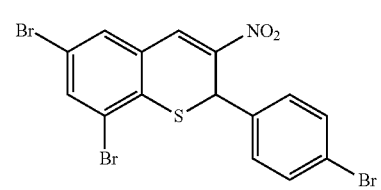
52
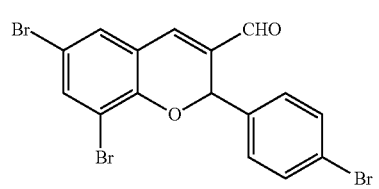
55
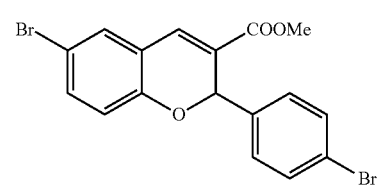

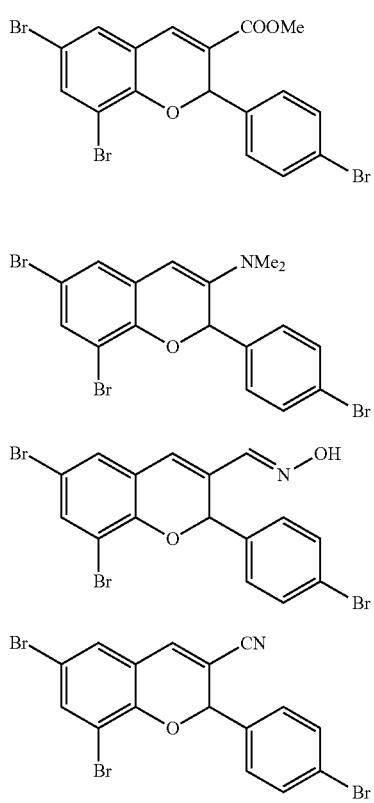
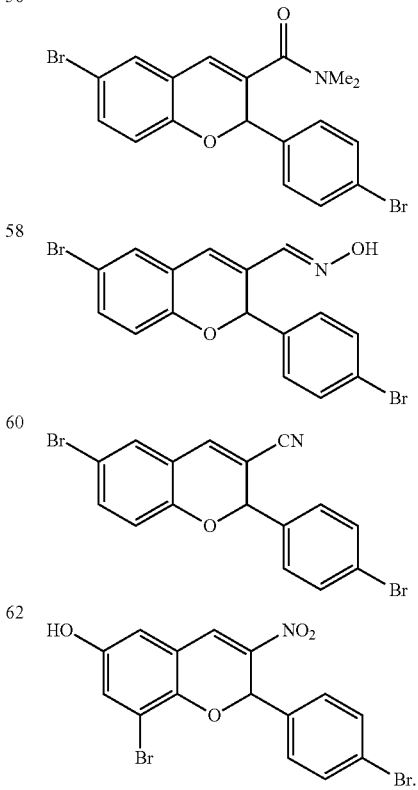
In one embodiment, the compound having formula (I):
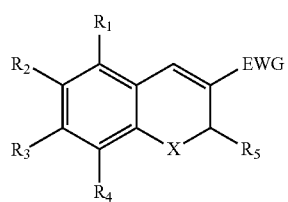
(I)
wherein EWG, X, $R_1$, $R_2$, $R_3$, $R_4$ and $R_5$ are as defined above,
and provided that the compound of formula (I) is not one of the following compounds:
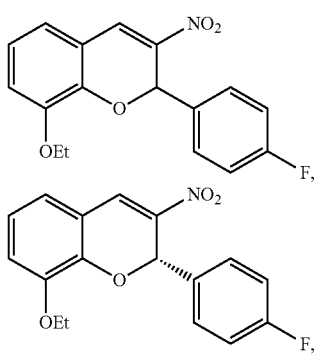
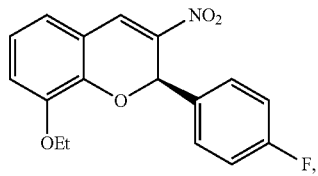
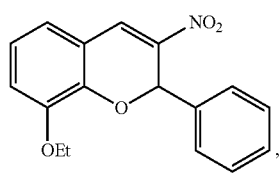
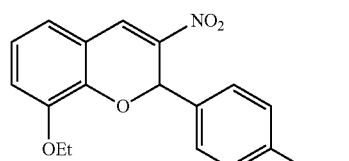
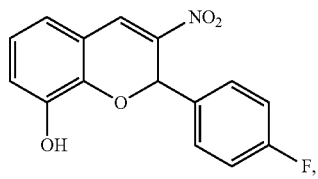

-continued

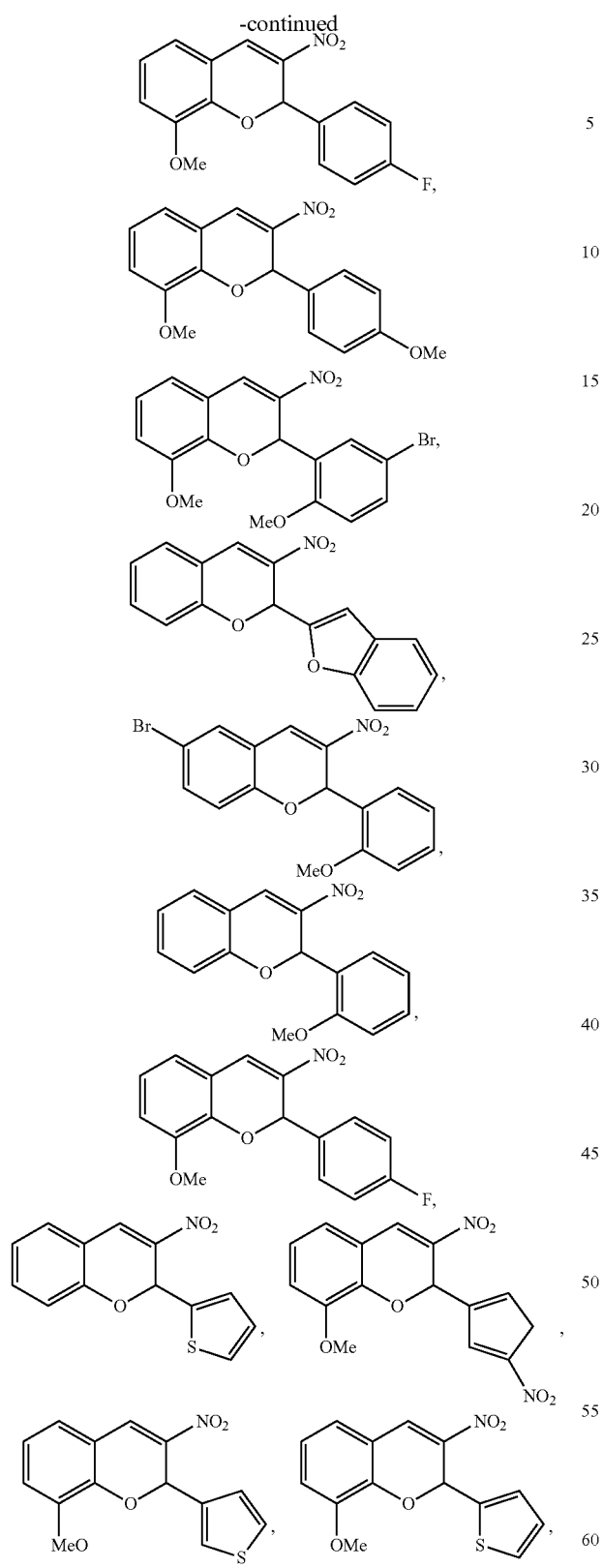

or its pharmaceutically acceptable salts, hydrates or hydrated salts or its polymorphic crystalline structures, racemates, diastereomers or enantiomers, is used for the prevention and/or the treatment of cancers.

In another embodiment, the compound having formula (I):

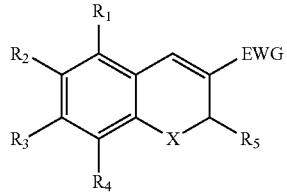

(I)

wherein EWG, X, $R_1$, $R_2$, $R_3$, $R_4$ and $R_5$ are as defined above, and provided that the compound of formula (I) is not one of the following compounds:

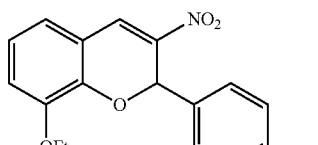

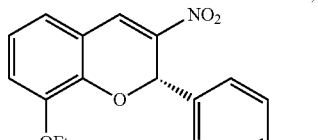

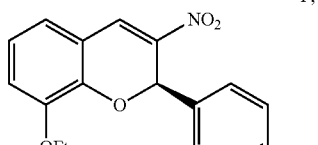

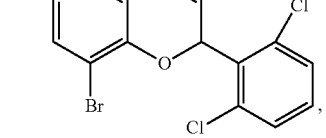

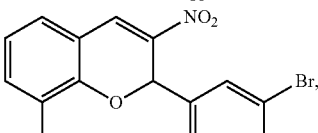

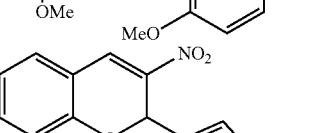

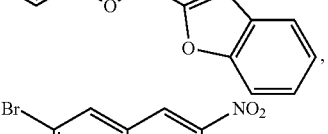

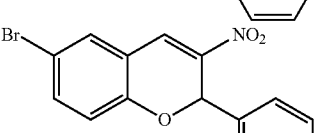

-continued

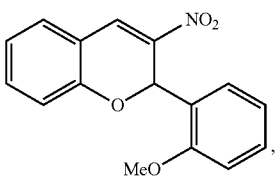

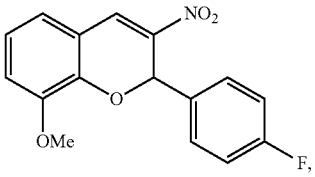

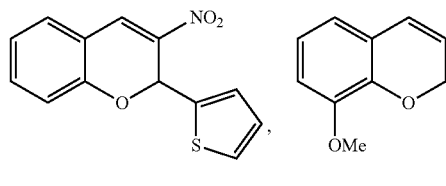

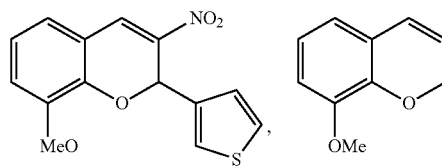

or its pharmaceutically acceptable salts, hydrates or hydrated salts or its polymorphic crystalline structures, racemates, diastereomers or enantiomers, is used for the prevention and/or the treatment of inflammatory diseases.

In another embodiment, the compound having formula (I):

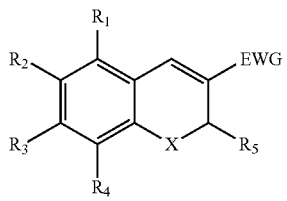

(I)

wherein EWG, X, $R_1$, $R_2$, $R_3$, $R_4$ and $R_5$ are as defined above, and provided that the compound of formula (I) is not one of the following compounds:

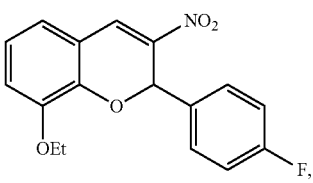

-continued

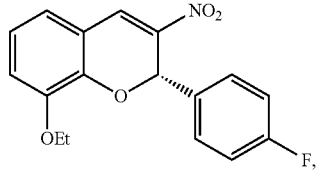

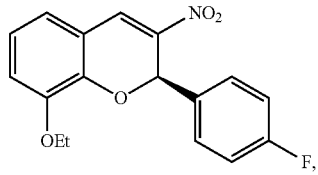

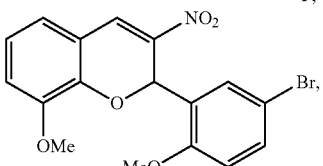

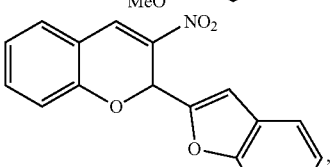

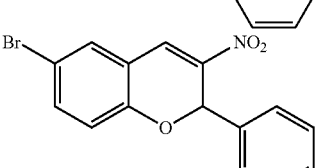

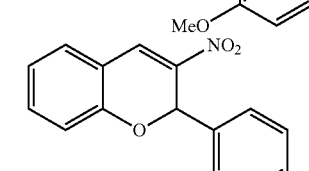

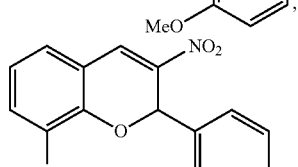

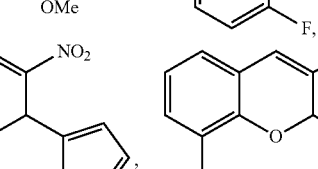

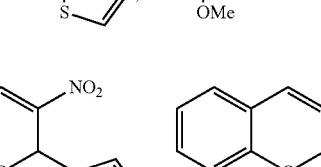

or its pharmaceutically acceptable salts, hydrates or hydrated salts or its polymorphic crystalline structures, racemates, diastereomers or enantiomers, is used for the prevention and/or the treatment of type II diabetes.

In another embodiment, the compound having formula (I):

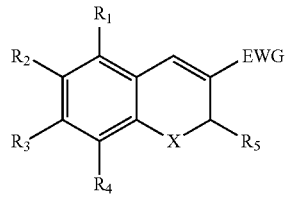

wherein EWG, X, $R_1$, $R_2$, $R_3$, $R_4$ and $R_5$ are as defined above, and provided that the compound of formula (I) is not one of the following compounds:

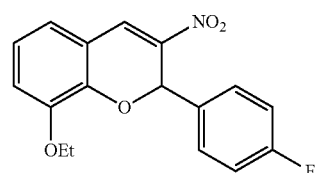

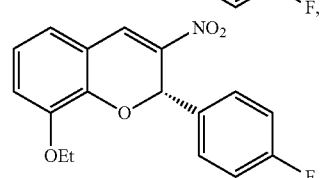

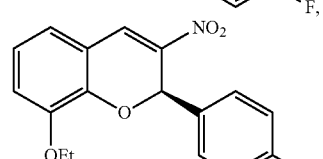

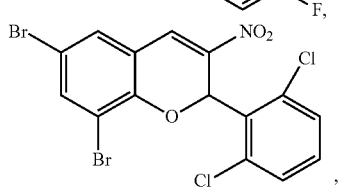

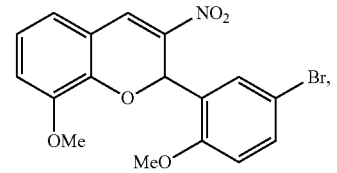

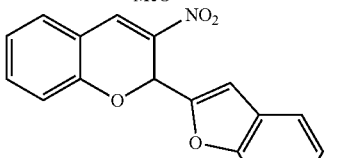

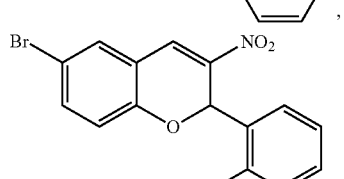

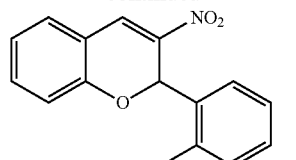

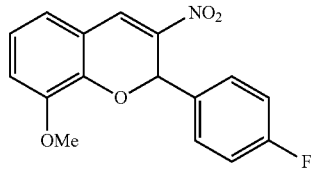

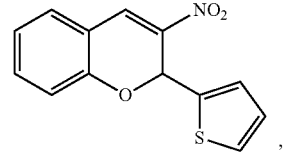

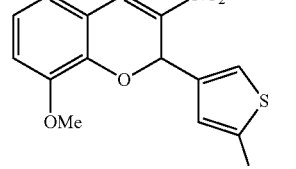

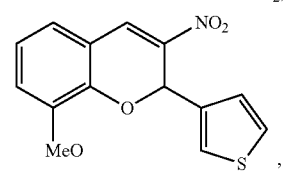

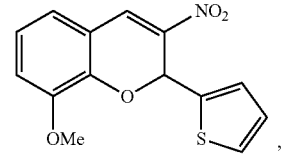

or its pharmaceutically acceptable salts, hydrates or hydrated salts or its polymorphic crystalline structures, racemates, diastereomers or enantiomers, is used for the prevention and/or the treatment of transplant rejection.

In another embodiment, the compound having formula (I):

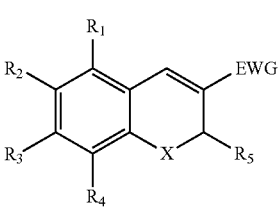

wherein EWG, X, $R_1$, $R_2$, $R_3$, $R_4$ and $R_5$ are as defined above, and provided that the compound of formula (I) is not one of the following compounds:

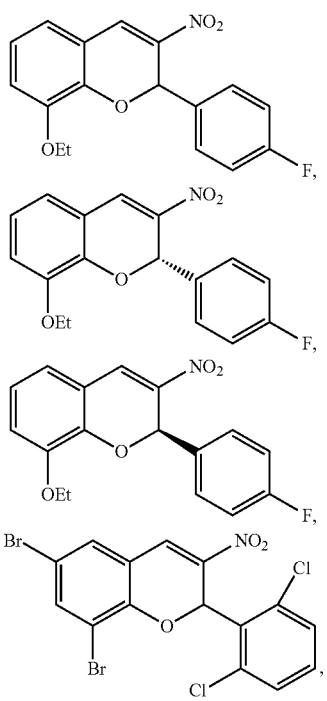

or its pharmaceutically acceptable salts, hydrates or hydrated salts or its polymorphic crystalline structures, racemates, diastereomers or enantiomers,
is used for the prevention and/or the treatment of autoimmune diseases.

In another embodiment, the compound having formula (I):

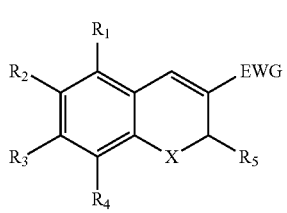

(I)

wherein EWG, X, $R_1$, $R_2$, $R_3$, $R_4$ and $R_5$ are as defined above,
and provided that the compound of formula (I) is not one of the following compounds:

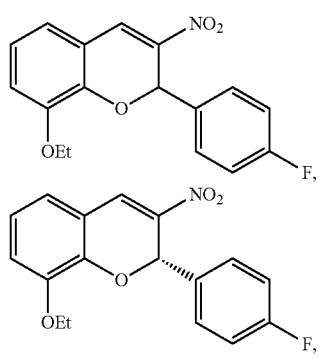

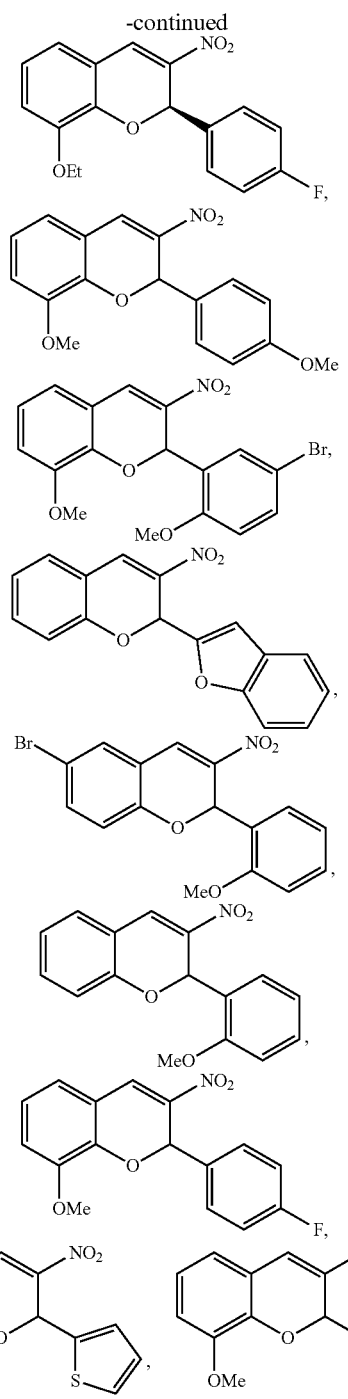

or its pharmaceutically acceptable salts, hydrates or hydrated salts or its polymorphic crystalline structures, racemates, diastereomers or enantiomers,
is used for the prevention and/or the treatment of neurodegenerative diseases.

In another embodiment, the compound having formula (I):

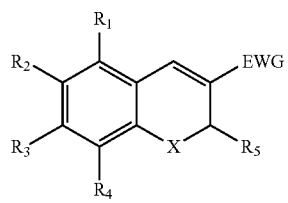

wherein EWG, X, $R_1$, $R_2$, $R_3$, $R_4$ and $R_5$ are as defined above,
or its pharmaceutically acceptable salts, hydrates or hydrated salts or its polymorphic crystalline structures, racemates, diastereomers or enantiomers, is used for the prevention and/or the treatment of diseases characterized by a premature aging.

The invention also relates to the compound of formula (I) defined above, for its use for the prevention and/or the treatment of proliferative diseases such as benign and/or malignant tumors. A tumor (neoplasm) is a pathological volume increase of a tissue due to an abnormal cell proliferation. Malignant tumors are called hereafter "cancers". Contrarily to malignant tumors, benign tumors do not form metastasis. In one particular embodiment, the compound of formula (I) as defined above is used to treat skin, renal, pulmonary and/or cerebral benign tumors.

By the term "cancer" is meant malignant solid tumors and/or disseminated hematological cancers and/or their metastasis. The terms "metastasis" or "metastatic diseases" refer to secondary malignant tumors that are formed by cells from a primary malignant tumor, which have moved to another localization. The term "hematological cancers" refers to types of cancer that affect blood, bone marrow, and lymph nodes such as myelomas, lymphomas or leukemias.

More particularly, the invention relates to the compound of formula (I) defined above for its use for the treatment and/or prevention of leukaemia, lymphoma, colorectal cancers, pancreatic cancers, lung cancers, ovarian cancers, liver cancers, breast cancers, more preferably triple negative breast cancers, and metastatic diseases.

Preferably, compounds according to the invention are useful in the prevention and/or the treatment of breast cancer and/or the metastasis of primary malignant breast tumor(s). For example of breast cancer, it may be cited Estrogen Receptor-positive breast cancer, HER2-positive breast cancer, anti-estrogen resistant Estrogen Receptor-positive breast cancer, trastuzumab refractory HER2-positive (Human Epidermal Growth Factor Receptor 2-positive) breast cancer and triple-negative breast cancer (Pradip De et al. Cancer Treat. Rev., 2013). More preferably, the breast cancers to be prevented and/or treated are triple-negative breast cancers.

Indeed, it has been shown that PI3K/AKT/mTOR pathway inhibitors have significant anti-proliferative effects (P. De et al. Cancer Treat. Rev. 2013). A significant fraction of patients with breast cancer relapse and the PI3K/AKT/mTOR signaling pathway plays a pivotal role in the chemotherapy resistance observed in these breast cancer patients (Miller, T. W., Balko, J. M. & Arteaga, C. L. Phosphatidylinositol 3-kinase and antiestrogen resistance in breast cancer. *Journal of clinical oncology: official journal of the American Society of Clinical Oncology* 29, 4452-4461, (2011) and Sokolosky, M. L. et al. Involvement of Akt-1 and mTOR in sensitivity of breast cancer to targeted therapy. *Oncotarget* 2, 538-550 (2011)). Triple-negative breast cancer, a subtype distinguished by negative immunohistochemical staining for expression of the estrogen and progesterone receptors (ER/PR) and human epidermal growth factor receptor-2 (HER2) represents between 10 and 20% of all breast cancers. Triple-negative tumors cannot be treated with endocrine therapy or therapies targeted to HER2. Given that triple-negative cancers demonstrate higher levels of AKT activation compared with non-triple-negative breast cancers (Adamo, B. et al. Phosphatidylinositol 3-kinase pathway activation in breast cancer brain metastases. *Breast cancer research: BCR* 13, R125, (2011), the inhibition of the PI3K/AKT signaling pathway may block the process of tumor survival and cell migration in this aggressive sub-group of malignant tumor.

In particular embodiment, the compound of formula (I) defined above is used for the prevention and/or the treatment of tuberous sclerosis. Tuberous sclerosis or tuberous sclerosis complex (TSC), also called Bourneville's disease, is a rare multi-system autosomal dominant genetic disease that causes non-malignant tumors (benign tumors) in the brain and in other vital organs such as the kidneys, heart, eyes, lungs, and skin. TSC may be characterized by the formation of hamartia, hamartomas (benign tumors such as facial angiofibroma and subependymal nodules), renal angiomyolipomas (benign tumors), pulmonary lymphangiomyomatosis and, very rarely, cancerous hamartoblastomas.

In TSC, mutations on genes TCS1, encoding for hamartin, and TSC2, encoding for tuberin, lead to a hamartin-tuberin complex that does not inhibit mTOR as it should do. mTOR is thus constitutively expressed in patients suffering from TSC (Peter B. Crino et al., The New England Journal of Medicine Sep. 28, 2006 355; 1345-56.).

The compounds of formula (I) are also intended as anti-aging drugs: it is known that mTOR pathway inhibition has a positive effect on mice life span (Dudley W. Lamming et al., J. Clin. Invest. 2013; 123(3):980-989). Accordingly, the compounds of formula (I) may be used for the prevention and/or treatment of "diseases characterized by a premature aging" such as progeria. It has been shown that rapamycin, a mTOR inhibitor, ameliorates premature senescence in cells derived from patients with Hutchinson-Gilford progeria (Dudley W. Lamming et al., J. Clin. Invest. 2013; 123(3): 980-989).

The role of the PI3K/AKT/mTOR pathway in aging is thus related to aged-related disorders such as the neurodegenerative disorders (Don Benjamin et al. Nature Reviews Drug Discovery, 868, November 2011, vol. 10 and Dudley W. Lamming et al., J. Clin. Invest. 2013; 123(3):980-989). The term "neurodegenerative diseases" includes pathologies characterized by the progressive loss of structure and/or function of neurons, sometimes leading to their death. Among the neurodegenerative diseases, Parkinson's disease, Alzheimer's disease or Huntington's disease may be cited.

Furthermore, it has been shown that the inhibition of the PI3K/AKT/mTOR pathway plays a role in diabetes, age-related disorders, auto-immune disorders and transplant rejection (Don Benjamin et al. Nature Reviews Drug Discovery, 868, November 2011, vol. 10).

The compounds of formula (I) defined above are thus also intended to prevent and/or treat type II diabetes (Dudley W. Lamming et al., J. Clin. Invest. 2013; 123(3):980-989).

The terms "inflammatory diseases" refers to diseases characterized by a chronic inflammation. By "inflammation" is meant the phenomena by which the human body usually defends itself against aggression and which can manifest itself in various symptoms such as swelling, heat or redness of the skin. The terms "autoimmune diseases" refers to diseases in which the immune system is dysregulated meaning that the immune response of the body against substances or tissues normally present in the body is inappropriate. Among autoimmune diseases, it can be cited Crohn's disease or systemic lupus erythematosus (lupus). The term "transplant rejection" refers to the host reaction against the graft or the graft-versus-host disease. In one embodiment, the compound of formula (I) as defined above may be used as an immunosuppressant drug, more particularly as an immunosuppressant drug to prevent transplant rejection.

The present invention also relates to the use of a compound of formula (I) for the preparation of a medicament for the prevention and/or treatment of a disease selected from the group consisting of: inflammatory diseases, autoimmune diseases, neurodegenerative diseases, cancers, transplant rejection, diseases characterized by a premature aging and tuberous sclerosis.

The present invention also relates to a method of prevention and/or treatment of a disease selected from the group consisting of: inflammatory diseases, autoimmune diseases, neurodegenerative diseases, cancers, transplant rejection, diseases characterized by a premature aging and tuberous sclerosis comprising the administration of a pharmaceutical acceptable amount of a compound of formula (I) defined above to a patient in need thereof.

More particularly, the invention relates to a method of prevention and/or treatment of tuberous sclerosis, comprising the administration of a pharmaceutical acceptable amount of a compound of formula (I) defined above to a patient in need thereof.

In the context of the invention, the term "treating" or "treatment", as used herein, means reversing, alleviating, inhibiting the progress of, or preventing the disorder or condition to which such term applies, or one or more symptoms of such disorder or condition.

The present invention also relates to a pharmaceutical composition, comprising a compound having formula (I) as defined above, in association with at least one pharmaceutically acceptable excipient.

The present invention also relates to a drug, comprising a compound having formula (I) as defined above.

While it is possible for the compounds of the invention having formula (I) to be administered alone, it is preferred to present them as pharmaceutical compositions. The pharmaceutical compositions, both for veterinary and for human use, useful according to the present invention comprise at least one compound having formula (I) as above defined, together with one or more pharmaceutically acceptable carriers and possibly other therapeutic ingredients.

In certain preferred embodiments, active ingredients necessary in combination therapy may be combined in a single pharmaceutical composition for simultaneous administration.

As used herein, the term "pharmaceutically acceptable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use can also be prepared. The preparation can also be emulsified. In particular, the pharmaceutical compositions may be formulated in solid dosage form, for example capsules, tablets, pills, powders, dragees or granules.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

The pharmaceutical compositions can be administered in a suitable formulation to humans and animals by topical or systemic administration, including oral, rectal, nasal, buccal, ocular, sublingual, transdermal, rectal, topical, vaginal, parenteral (including subcutaneous, intra-arterial, intramuscular, intravenous, intradermal, intrathecal and epidural), intracisternal and intraperitoneal. It will be appreciated that the preferred route may vary with for example the condition of the recipient.

The formulations can be prepared in unit dosage form by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

DESCRIPTION OF THE FIGURES

FIG. 12A shows the inhibition of the phosphorylation of AKT at serine 473 and of 4EBP1 at threonine 37/46. FIG. 12B shows the binding of compound 48 to the protein mTOR.

FIG. 13A shows the body weight of the tested mice in grams versus the time in days. FIG. 13B shows the percentage of survival of the tested mice versus the time in days.

FIG. 14A shows the cell number of $TSC2^{-/-}$ (white circles) and $TSC2^{+/+}$ (black circles) obtained in culture over time (in hours). FIG. 14B shows the percentage of cell death (metabolic activity) of $TSC2^{-/-}$ (white circles) and $TSC2^{+/+}$ (black circles) versus the concentration of compound 25 in μM. FIG. 14C shows the percentage of cell death (metabolic activity) of $TSC2^{-/-}$ (white circles) and $TSC2^{+/+}$ (black circles) versus the concentration of rapamycin in μM.

Figure 1:
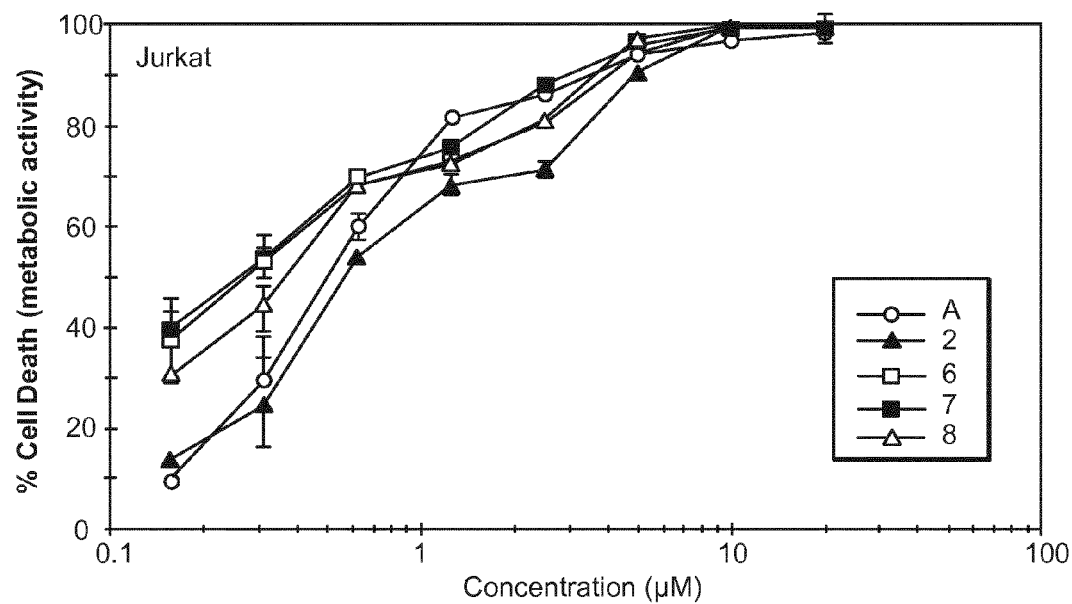
FIG. 1 and FIG. 6 show the percentage of cell death of leukemic T-cells Jurkat, versus the concentration of some compounds of formula (I).

The following examples show the improved PI3K/AKT/mTOR inhibition and the increased cytotoxic effect of the compounds of formula (I). Some preparative examples are also given below, without limitation of the present invention.

DETAILED DESCRIPTION

Preparative Examples

1. Preparation of Compounds 1 to 40

General Procedure to Prepare Compounds of Formula (I) Wherein EWG is $NO_2$:

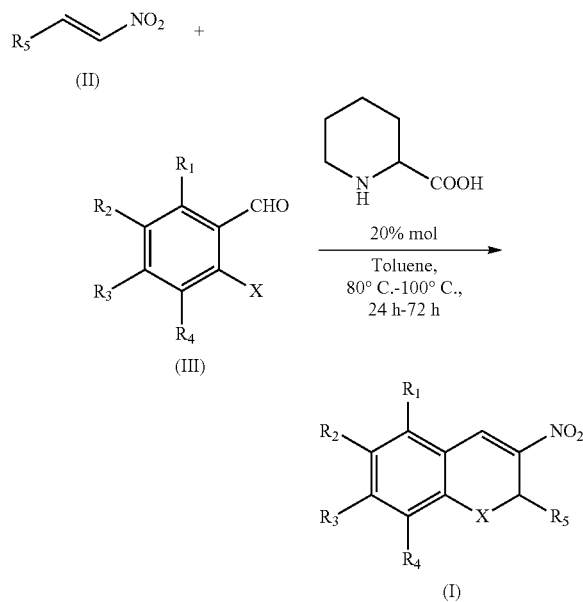

The mixture of nitrostyrene derivative (1 mmol), salicylaldehyde compound (1 mmol) and pipecolic acid (0.2 mmol) in 1.5 mL of dry toluene was heated at 80-100° C. for 24-72 h under nitrogen atmosphere (conversion followed by TLC). After cooling to the room temperature, the mixture was charged directly on the silica gel column for the separation to give desired chromene (yields=40-75%). Room temperature is comprised between 18° C. and 25° C.

$R_1$, $R_2$, $R_3$, $R_4$, $R_5$ and X are defined above.

General Procedure to Prepare Compounds of Formula (I) Wherein EWG is CHO:

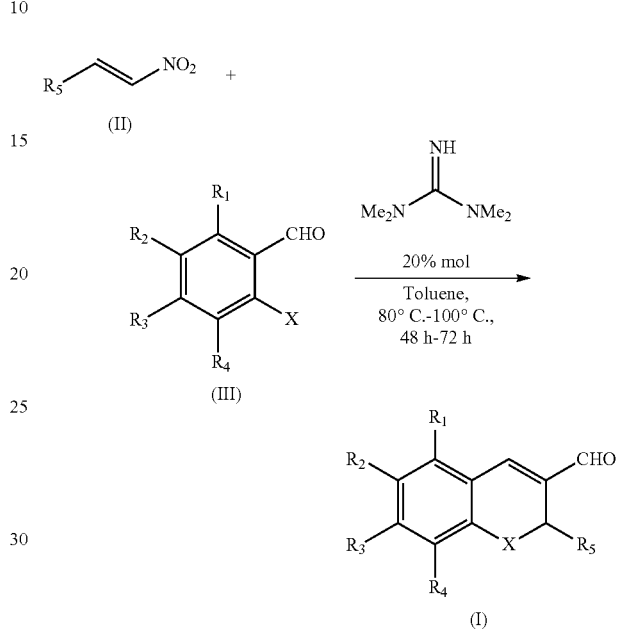

The mixture of cinnamaldehyde derivative (1 mmol), salicylaldehyde compound (1 mmol) and 1,1,3,3-Tetramethylguanidine (0.2 mmol) in 1.5 mL of dry toluene was heated at 80-100° C. for 48-72 h under nitrogen atmosphere (conversion followed by TLC). After cooling to room temperature, the mixture was charged directly on the silica gel column for the separation to give desired chromene (yields=30-55%). Room temperature is comprised between 18° C. and 25° C.

$R_1$, $R_2$, $R_3$, $R_4$, $R_5$ and X are defined above. The starting products used were obtained as follows:

| Compounds of formula (III) | Corresponding compounds of formula (I) |
|---|---|
| 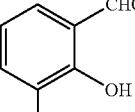 marketed by Aldrich CAS [148-53-8] | 1. |
| 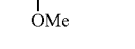 marketed by Aldrich CAS [492-88-6] | 13 to 16 and 35. |

-continued

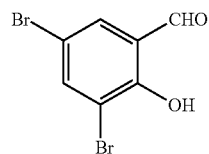

2, 25 to 27 and 39.

marketed by Aldrich
CAS [90-59-5]

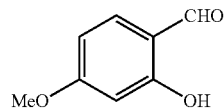

3.

marketed by Aldrich
CAS [673-22-3]

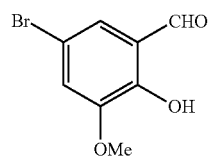

6, 22 to 24 and 40.

marketed by Aldrich
CAS [5034-74-2]

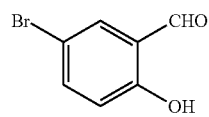

7, 9 to 11, 33, 34 and 36.

marketed by Aldrich
CAS [1761-61-1]

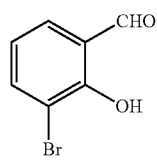

8, 18 to 20 and 37.

marketed by Aldrich
CAS [1829-34-1]

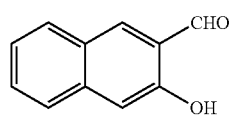 [SMILES: O=Cc1cc2ccccc2cc1O]

5.

prepared according to B. Legoin et al., Eur. J. Org. Chem. 2010, 5503-5508.

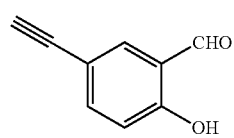

32.

prepared according to Y. Xu et al., Chem. Eur. J., 2010, 16, 12898-12903.

-continued

| Compounds of formula (II) | Corresponding compounds of formula (I) |
|---|---|
| 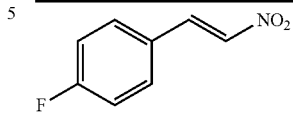 marketed by Aldrich CAS [706-08-1] | 1 to 3 and 5 to 8. |
| 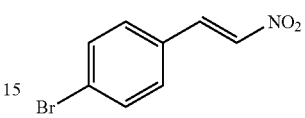 marketed by Aldrich CAS [5153-71-9] | 9, 13, 18, 22, 25 and 32. |
| 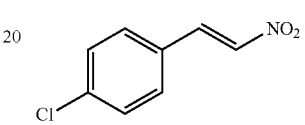 marketed by Aldrich CAS [706-07-0] | 10, 14, 19, 23 and 26. |
| 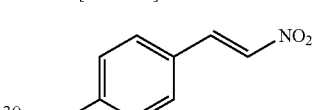 prepared according to J. A. Burkhard et al., Angew. Chem. Int. Ed. 2011, 50, 5379-5382. | 11, 15, 20, 24 and 27. |
| 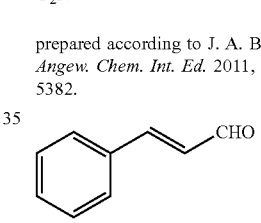 marketed by Aldrich CAS [104-55-2] | 33, 35. |
| 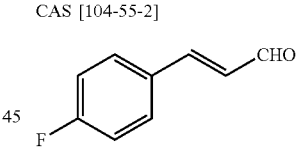 marketed by Aldrich CAS [51791-26-5] | 34. |
| 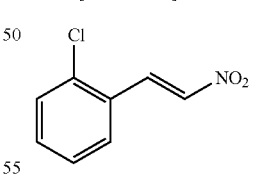 marketed by Aldrich CAS [3156-34-1] | 16. |
| 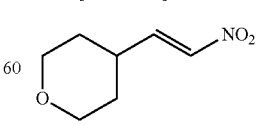 prepared according to D. A. DiRocco, T. Rovis, J. Am. Chem. Soc., 2011, 133, 10402-10405. | 36, 37, 39 and 40. |

2. Preparation of Compounds 41 to 63

Preparation of Compounds 50 and 51

Dimethylthiocarbamic Acid O-(4-Bromo-2-Formylphenyl) Ester

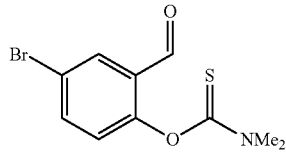 [SMILES: CN(C)C(=S)Oc1ccc(Br)cc1C=O]

To a solution of 5-bromosalicylaldehyde (5.0 g, 25.0 mmol) in dry acetonitrile (25 mL) was added potassium carbonate (13.75 g, 100.0 mmol, 4.0 eq.) at room temperature. After 10 minutes dimethylthiocarbamoyl chloride (3.7 g, 30.0 mmol, 1.2 eq.) was added and the mixture was heated at reflux for 4 h. Then the reaction mixture was then cooled to room temperature, diluted with EtOAc and washed with a saturated aqueous NaHCO$_3$ solution. The combined organic layers were washed with brine, dried over MgSO$_4$, filtered and the filtrate concentrated under reduced pressure. The title compound was purified by column chromatography on silica gel using PE/EtOAc 9/1 to 7/3 as eluent affording a yellow solid (5.5 g, 77%). Mp=144-146° C. $^1$H-NMR (CDCl$_3$, 500 MHz) δ 3.42 (s, 3H), 3.47 (s, 3H), 7.03 (d, J=8.5, 1H), 7.72 (dd, J=8.5, 2.2, 1H), 8.02 (d, J=2.2, 1H), 9.99 (s, 1H). $^{13}$C-NMR (CDCl$_3$, 125 MHz) δ 39.0, 43.5, 119.9, 126.3, 130.5, 132.1, 137.6, 154.3, 186.7, 186.7.

Dimethylthiocarbamic acid S-(4-bromo-2-formylphenyl) ester

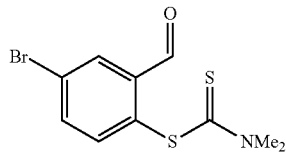 [SMILES: CN(C)C(=S)Sc1ccc(Br)cc1C=O]

Dimethylthiocarbamic acid O-(4-bromo-2-formylphenyl) ester (5.4 g, 18.7 mmol) was heated neat at 150° C. for 15 h then cooled to room temperature. The title compound was purified by column chromatography on silica gel using PhMe/Et$_2$O 95/5 to 90/10 as eluent affording a yellow solid (1.1 g, 20%). Mp=116-118° C. $^1$H-NMR (CDCl$_3$, 300 MHz) δ 3.03 (s, 3H), 3.16 (s, 3H), 7.42 (d, J=8.2, 1H), 7.70 (dd, J=8.2, 2.4, 1H), 8.14 (d, J=2.4, 1H), 10.25 (s, 1H). $^{13}$C-NMR (CDCl$_3$, 75 MHz) δ 37.1, 37.3, 124.9, 131.1, 131.6, 136.5, 138.7, 138.9, 164.6, 189.8.

6-Bromo-2-(4-bromophenyl)-3-nitro-2H-thiochromene (50)

To a solution of dimethylthiocarbamic acid S-(4-bromo-2-formylphenyl) ester (200 mg, 0.69 mmol) in methanol (4.3 mL) was added an aqueous NaOH solution (0.8 M, 4.3 mL, 3.45 mmol, 5 eq.) at room temperature. After 2 h, a 10% (w/v) aqueous citric acid solution was added followed by water and the mixture was extracted with EtOAc. The combined organic layers were washed with brine, dried over MgSO$_4$, filtered and the filtrate concentrated under reduced pressure. The resulting crude thiophenol was dissolved in dry toluene and 1-bromo-4-(2-nitrovinyl)benzene (158 mg, 1 eq., 0.69 mmol) was added followed by pipecolic acid (45 mg, 0.5 eq., 0.35 mmol). The reaction mixture was heated at 100° C. for 12 h then cooled to room temperature. The solvent was removed under reduce pressure and the title compound was purified by column chromatography on silica gel using PE/PhMe 4/1 as eluent affording a yellow solid (115 mg, 39%).

Dimethylthiocarbamic acid O-(2,4-dibromo-6-formylphenyl) ester

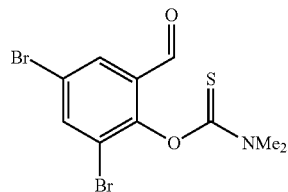 [SMILES: CN(C)C(=S)Oc1c(Br)cc(Br)cc1C=O]

To a solution of 3,5-dibromosalicylaldehyde (1.2 g, 4.3 mmol) in dry tetrahydrofurane (10 mL) was added sodium hydride (60% in oil, 0.19 g, 4.7 mmol, 1.1 eq.) at 0° C. After 15 minutes at 0° C. and 1 h at room temperature a solution of dimethylthiocarbamoyl chloride (0.65 g, 5.2 mmol, 1.2 eq.) in dry tetrahydrofurane (2 mL) was added at 0° C. and the mixture was stirred at room temperature for 12 h. Then a saturated aqueous NH$_4$Cl solution was added and the mixture was extracted with EtOAc. The combined organic layers were washed with brine, dried over MgSO$_4$, filtered and the filtrate concentrated under reduced pressure. The title compound was purified by column chromatography on silica gel using PE/Et$_2$O 9/1 to 7/3 as eluent affording a yellow solid (0.4 g, 25%). $^1$H-NMR (CDCl$_3$, 500 MHz) δ 3.48 (s, 3H), 3.49 (s, 3H), 7.96 (d, J=2.4, 1H), 7.99 (d, J=2.4, 1H), 9.94 (s, 1H). $^{13}$C-NMR (CDCl$_3$, 125 MHz) δ 39.2, 43.8, 119.6, 120.2, 130.8, 132.3, 140.4, 151.9, 185.1, 186.2.

Dimethylthiocarbamic acid S-(2,4-dibromo-6-formylphenyl) ester

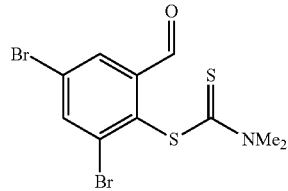

Dimethylthiocarbamic acid O-(2,4-dibromo-6-formylphenyl) ester (0.26 g, 0.71 mmol) was heated neat at 150° C. for 15 h then cooled to room temperature. The title compound was purified by column chromatography on silica gel using PhMe/Et$_2$O 9/1 as eluent affording a yellow solid (0.17 g, 53%). Mp=134-136° C. $^1$H-NMR (CDCl$_3$, 500 MHz) δ 3.04 (s, 3H), 3.22 (s, 3H), 8.06 (d, J=2.2, 1H), 8.09 (d, J=2.2, 1H), 10.25 (s, 1H). $^{13}$C-NMR (CDCl$_3$, 125 MHz) δ 37.3, 37.4, 125.2, 130.7, 132.6, 133.0, 140.0, 140.9, 163.1, 189.7.

6,8-Dibromo-2-(4-bromophenyl)-3-nitro-2H-thiochromene (51)

To a solution of dimethylthiocarbamic acid S-(2,4-dibromo-6-formylphenyl) ester (160 mg, 0.43 mmol) in methanol (2.7 mL) was added an aqueous NaOH solution (0.8 M, 2.7 mL, 2.15 mmol, 5 eq.) at room temperature. After 2 h, a 10% (w/v) aqueous citric acid solution was added followed by water and the mixture was extracted with EtOAc. The combined organic layers were washed with brine, dried over $MgSO_4$, filtered and the filtrate concentrated under reduced pressure. The resulting crude thiophenol was dissolved in dry toluene and 1-bromo-4-(2-nitrovinyl)benzene (98 mg, 1 eq., 0.43 mmol) was added followed by pipecolic acid (28 mg, 0.5 eq., 0.22 mmol). The reaction mixture was heated at 100° C. for 12 h then cooled to room temperature. The solvent was removed under reduce pressure and the title compound was purified by column chromatography on silica gel using PE/PhMe 4/1 as eluent followed by a preparative thin layer chromatography using PE/PhMe 3/2 as eluent affording a yellow solid (40 mg, 19%).

Preparation of Compounds 44 and 52

To a solution of salicylaldehyde derivative was placed in dry toluene and 1-bromo-4-(2-nitrovinyl)benzene (1.1 eq.) was added followed by tetramethylguanidine (0.5 eq.) and benzoic acid (0.5 eq.). The reaction mixture was heated at 100° C. for 16 h then cooled to room temperature. The solvent was removed under reduce pressure and the title compound was purified by column chromatography on silica gel using PhMe/$Et_2O$ 7/3 as eluant affording a yellow solid.

Preparation of Compounds 55 and 56

To a solution of carboxylic acid 53 or 54 in methanol, thionyl chloride (1.6 eq.) was added. The reaction mixture was heated at reflux for 20 h then cooled to room temperature. The solvent was removed under reduce pressure and the title compound was purified by column chromatography on silica gel using PhMe/PE 3/1 as eluant.

Preparation of Compounds 57 and 58

To a solution of carboxylic acid 53 or 54 in methylene chloride in the presence of one drop of DMF, oxalyle chloride (1.15 eq.) was added. The reaction mixture was stirred 20 h at room temperature and $Me_2NH.HCl$ (2 eq.) and $Et_3N$ (5 eq.) were added. The reaction mixture was stirred 4 h at room temperature and after addition of HCl 1M, the aqueous phase was extracted with EtOAc. The combined organic layers were washed with brine, dried over $MgSO_4$, filtered and the filtrate concentrated under reduced pressure. The title compound was purified by column chromatography on silica gel using $CH_2Cl_2$/AcOEt 8/2 as eluant.

Preparation of Compounds 59 and 60

To a solution of aldehyde 44 or 52 in methanol, were successively added hydroxylamine chlorhydrate (5 eq.) and triethylamine (5 eq.). The reaction mixture was stirred 16 h at room temperature. After addition of HCl 1M the solution was extracted with EtOAc. The combined organic layers were washed with brine, dried over $MgSO_4$, filtered and the filtrate concentrated under reduced pressure. The title compound was purified by column chromatography on silica gel using PhMe/PE 7/3 as eluant.

Preparation of Cyano 61 and 62

A solution of aldehyde 44 or 52 and $NH_2OH.HCl$ (1.5 eq.) in DMSO was stirred at 100° C. for 20 h. After addition of water, the solution was extracted with $Et_2O$. The combined organic layers were washed with brine, dried over $MgSO_4$, filtered and the filtrate concentrated under reduced pressure. The title compound was purified by column chromatography on silica gel using PE/AcOEt 85/15 as eluant.

Analytic Data:

8-ethoxy-2-(4-fluoropheneyl)-3-nitro-3,4-dihydro-2H-chromene (compound A)

$^1$H NMR ($CDCl_3$, 500 MHz): δ (ppm)=1.36 (s, 3H, J=7.1 Hz), 3.97-4.08 (m, 2H, J=7.1 Hz), 6.64 (s, 1H), 6.93-6.99 (m, 5H), 7.37 (d, 1H; J=5.2 Hz), 7.38 (d, 1H, J=5.2 Hz), 8.03 (s, 1H).

$^{13}$C NMR ($CDCl_3$, 125 MHz): δ (ppm)=164.2, 162.2, 148.0, 143.0, 141.3, 132.6, 129.5, 128.9, 128.8, 122.6, 122.2, 118.9, 118.7, 115.8, 115.6, 65.2, 14.7.

2-(4-fluorophenyl)-8-methoxy-3-nitro-3,4-dihydro-2H-chromene (1)

$^1$H NMR ($CDCl_3$, 500 MHz): δ (ppm)=4.11 (s, 3H), 6.93 (s, 1H), 7.24-7;30 (m, 5H), 7.66 (d, 2H), 7.69 (d, 1H), 8.33 (s, 1H).

$^{13}$C NMR ($CDCl_3$, 125 MHz): δ (ppm)=164.3, 162.3, 148.7, 142.5, 141.3, 132.6, 129.3, 129.0, 128.9, 122.6, 122.1, 118.6, 115.9, 115.7, 56.3.

6,8-dibromo-2-(4-fluorophenyl)-3-nitro-3,4-dihydro-2H-chromene (2)

$^1$H NMR ($CDCl_3$, 500 MHz) δ (ppm)=6.68 (s, 1H), 7.02 (m, 2H), 7.34 (d, 1H), 7.36 (d, 1H), 7.40 (s, 1H), 7.65 (s, 1H), 7.94 (s, 1H).

$^{13}$C NMR ($CDCl_3$, 125 MHz) δ (ppm)=164.4, 162.4, 149.3, 142.5, 139.1, 131.6, 128.9, 128.8, 127.4, 120.6, 116.9, 116.2, 116.0, 114.8, 112.4.

2-(4-fluorophenyl)-7-methoxy-3-nitro-3,4-dihydro-2H-chromene (3)

$^1$H NMR ($CDCl_3$, 500 MHz) δ (ppm)=6.39 (d, 1H), 6.53 (s, 1H), 6.57 (dd, 1H), 7.0 (m, 2H), 7.24 (d, 1H), 7.34-7.36 (m, 2H), 8.04 (s, 1H).

$^{13}$C NMR ($CDCl_3$, 125 MHz) δ (ppm)=165.2, 164.2, 162.3, 155.4, 138.2, 133.0, 131.8, 129.9, 129.0, 115.9, 115.8, 110.0, 109.9, 102.3, 55.7.

2-(4-fluorophenyl)-3-nitro-3,4-dihydro-2H-benzo[g]chromene (5)

$^1$H NMR ($CDCl_3$, 300 MHz) δ (ppm)=6.49 (s, 1H), 6.90-6.97 (m, 4H), 7.23-7.31 (m, 5H), 7.99 (s, 1H).

$^{13}$C NMR ($CDCl_3$, 75 MHz) δ (ppm)=164.9, 161.6, 153.3, 141.0, 134.5, 132.8, 132.7, 130.5, 129.4, 129.1, 128.9, 128.5, 127.1, 122.7, 117.8, 117.3, 116.0, 115.7.

6-bromo-2-(4-fluorophenyl)-8-methoxy-3-nitro-3,4-dihydro-2H-chromene (6)

$^1$H NMR (CDCl$_3$, 300 MHz) δ (ppm)=3.76 (s, 3H), 6.59 (s, 1H), 6.94-7.03 (m, 4H), 7.49 (d, 1H), 7.53 (d, 1H), 7.92 (s, 1H).

6-bromo-2-(4-fluorophenyl)-3-nitro-3,4-dihydro-2H-chromene (7)

$^1$H NMR (CDCl$_3$, 300 MHz) δ (ppm)=6.54 (s, 1H), 6.75 (d, 1H, J=8.6 Hz), 7.00 (t, 2H, J=8.6 Hz), 7.32 (d, 1H, J=5.2 Hz), 7.35 (d, 1H, J=5.2 Hz), 7.45 (d, 1H, J=2.3 Hz), 7.96 (s, 1H).

8-bromo-2-(4-fluorophenyl)-3-nitro-3,4-dihydro-2H-chromene (8)

$^1$H NMR (CDCl$_3$, 300 MHz) δ (ppm)=6.60 (s, 1H), 6.81 (t, 1H), 6.90 (t, 2H), 7.20 (dd, 1H), 7.27-7.30 (m, 2H), 7.44 (dd, 1H), 7.94 (s, 1H).

6-bromo-2-(4-bromo-phenyl)-3-nitro-2H-chromene (9)

$^1$H NMR (CDCl$_3$, 300 MHz) δ (ppm)=6.52 (s, 1H), 6.77 (d, 1H, J=8.6 Hz), 7.23 (d, 2H, J=8.6 Hz), 7.45 (m, 4H), 7.61 (dd, 1H, J=6.1 and 2.9 Hz), 7.97 (s, 1H).
$^{13}$C NMR (CDCl$_3$, 75 MHz) δ (ppm)=73.8, 114.8, 119.1, 119.6, 124.0, 128.0, 128.7, 132.2, 132.5, 135.2, 136.9, 141.7, 152.2.

6-bromo-2-(4-chloro-phenyl)-3-nitro-2H-chromene (10)

$^1$H NMR (CDCl$_3$, 300 MHz) δ (ppm)=6.54 (s, 1H), 6.77 (d, 1H, J=8.6 Hz) 7.29-7.32 (m, 4H), 7.39-7.46 (m, 2H), 7.97 (s, 1H).
$^{13}$C NMR (CDCl$_3$, 75 MHz) δ (ppm)=73.7, 114.7, 119.0, 119.5, 127.9, 128.3, 128.4, 129.2, 129.8, 130.2, 132.4, 134.7, 135.7, 136.8, 137.6, 141.6, 152.0.

6-bromo-2-(4-nitro-phenyl)-3-nitro-2H-chromene (11)

$^1$H NMR (CDCl$_3$, 300 MHz) δ (ppm)=6.66 (s, 1H), 6.81 (d, 1H, J=8.6 Hz), 7.43-7.56 (m, 4H), 8.02 (s, 1H), 8.21 (m, 2H).
$^{13}$C NMR (CDCl$_3$, 75 MHz) δ (ppm)=73.2, 115.2, 119.0, 119.3, 124.2, 128.0, 128.6, 132.7, 137.2, 141.0, 142.9, 148.5, 152.0.

2-(4-bromo-phenyl)-8-ethoxy-3-nitro-2H-chromene (13)

$^1$H NMR (CDCl$_3$, 300 MHz) δ (ppm)=1.39 (t, 3H, J=6.9 Hz), 4.04 (q, 2H, J=7.1 Hz), 6.62 (s, 1H), 6.69 (m, 3H), 7.28 (m, 2H), 7.44 (dd, 2H, J=8.4 and 1.6 Hz), 8.03 (s, 1H).
$^{13}$C NMR (CDCl$_3$, 75 MHz) δ (ppm)=14.7, 65.0, 73.2, 118.5, 118.8, 122.1, 122.7, 123.4, 128.5, 129.6, 131.8, 135.7, 141.0, 142.8, 147.9.

2-(4-chloro-phenyl)-8-ethoxy-3-nitro-2H-chromene (14)

$^1$H NMR (CDCl$_3$, 300 MHz) δ (ppm)=1.38 (t, 3H, J=7 Hz), 3.97-4.08 (m, 2H), 6.63 (s, 1H), 6.91-6.96 (m, 3H), 7.25-7.34 (m, 4H), 8.03 (s, 1H).
$^{13}$C NMR (CDCl$_3$, 75 MHz) δ (ppm)=14.7, 65.0, 73.1, 118.6, 118.9, 122.2, 122.6, 128.3, 129.0, 129.6, 135.3, 141.1, 142.9, 148.0.

2-(4-nitro-phenyl)-8-ethoxy-3-nitro-2H-chromene (15)

$^1$H NMR (CDCl$_3$, 300 MHz) δ (ppm)=1.41 (t, 3H, J=7.0 Hz), 4.06 (m, 2H), 6.74 (s, 1H), 6.95 (m, 3H), 7.58 (d, 2H, J=8.5 Hz), 8.07 (s, 1H), 8.15 (d, 2H, J=8.9 Hz).
$^{13}$C NMR (CDCl$_3$, 75 MHz) δ (ppm)=14.7, 64.9, 72.6, 118.4, 118.6, 122.2, 123.1, 123.9, 127.7, 130.1, 140.5, 142.4, 143.7, 147.9, 148.28.

2-(2-chloro-phenyl)-8-ethoxy-3-nitro-2H-chromene (16)

$^1$H NMR (CDCl$_3$, 300 MHz) δ (ppm)=1.29 (t, 3H, J=7.0 Hz), 3.94 (q, 2H, J=3.6 Hz), 7.00 (m, 3H), 7.11-7.27 (m, 3H), 7.28 (m, 2H), 7.49 (dd, 1H, J=1.0, 7.9 Hz), 8.17 (s, 1H).
$^{13}$C NMR (CDCl$_3$, 75 MHz) δ (ppm)=14.7, 65.8, 70.8, 118.9, 120.6, 122.5, 122.6, 127.0, 128.0, 130.5, 130.6, 130.9, 133.0, 134.5, 140.1, 143.2, 148.14.

8-bromo-2-(4-bromo-phenyl)-3-nitro-2H-chromene (18)

$^1$H NMR (CDCl$_3$, 300 MHz) δ (ppm)=6.67 (s, 1H), 6.92 (t, 1H, J=7.9 Hz), 7.29 (m, 2H), 7.46 (m, 2H), 7.45-7.61 (m, 2H), 8.03 (s, 1H).
$^{13}$C NMR (CDCl$_3$, 75 MHz) δ (ppm)=72.8, 111.5, 119.4, 123.7, 123.8, 128.5, 128.9, 129.6, 132.1, 135.2, 137.5, 141.5, 150.1.

8-bromo-2-(4-chloro-phenyl)-3-nitro-2H-chromene (19)

$^1$H NMR (CDCl$_3$, 300 MHz) δ (ppm)=6.69 (s, 1H), 6.93 (t, 1H, J=7.7 Hz), 7.28-7.35 (m, 5H), 7.56 (dd, 1H, J=6.5 and 1.5 Hz), 8.03 (s, 1H).
$^{13}$C NMR (CDCl$_3$, 75 MHz) δ (ppm)=73.7, 111.4, 119.3, 123.6, 128.2, 128.8, 129.0, 129.50, 134.6, 135.5, 137.5, 141.5, 150.0.

8-bromo-2-(4-nitro-phenyl)-3-nitro-2H-chromene (20)

$^1$H NMR (CDCl$_3$, 300 MHz) δ (ppm)=6.80 (s, 1H), 6.94 (t, 1H, J=7.0 Hz), 7.31 (dd, 1H, J=7.0 and 1.0 Hz), 7.59 (m, 3H), 8.07 (s, 1H), 8.20 (d, 2H, J=7.0 Hz).
$^{13}$C NMR (CDCl$_3$, 75 MHz) δ (ppm)=73.3, 111.5, 119.2, 124.1, 124.5, 127.8, 129.4, 129.7, 129.8, 136.0, 137.8, 143.0, 149.9.

6-bromo-2-(4-bromo-phenyl)-8-methoxy-3-nitro-2H-chromene (22)

$^1$H NMR (CDCl$_3$, 300 MHz) δ (ppm)=3.82 (s, 3H), 6.60 (s, 1H), 7.04 (d, 1H, J=2.1 Hz), 7.08 (d, 1H, J=2.1 Hz), 7.24 (td, 2H, J=2.2 and 8.3 Hz), 7.47 (td, 2H, J=2.2 and 8.6 Hz), 7.95 (s, 1H).

$^{13}$C NMR (CDCl$_3$, 75 MHz) δ (ppm)=56.5, 73.6, 111.4, 119.7, 119.5, 123.9, 128.0, 128.5, 129.5, 132.1, 135.1, 141.7, 149.3.

6-Bromo-2-(4-chloro-phenyl)-8-methoxy-3-nitro-2H-chromene (23)

$^1$H NMR (CDCl$_3$, 300 MHz) δ (ppm)=3.82 (s, 3H), 6.60 (s, 1H), 7.08 (dd, 2H, J=13.1 and 2.0 Hz); 7.3 (s, 4H), 7.95 (s, 1H).

6-Bromo-2-(4-nitro-phenyl)-8-methoxy-3-nitro-2H-chromene (24)

$^1$H NMR (CDCl$_3$, 300 MHz) δ (ppm)=3.86 (s, 3H) 6.75 (s, 1H), 7.07 (d, 1H, J=2.1 Hz), 7.11 (d, 1H, J=2.1 Hz), 7.55 (td, 2H, J=2.0 and 8.5 Hz), 7.99 (s, 1H), 8.19 (td, 2H J=2.0 and 8.9 Hz).

6,8-dibromo-2-(4-bromo-phenyl)-3-nitro-2H-chromene (25)

$^1$H NMR (CDCl$_3$, 300 MHz) δ (ppm)=6.67 (s, 1H), 7.24 (m, 2H), 7.40 (d, 1H, J=2.2 Hz), 7.48 (m, 2H, J=8.5 and 1.95 Hz), 7.67 (d, 1H, J=2.2 Hz), 7.95 (s, 1H).
$^{13}$C NMR (CDCl$_3$, 75 MHz) δ (ppm)=73.9, 112.4, 114.8, 120.6, 124.1, 127.5, 128.4, 129.5, 121.5, 132.2, 132.7, 134.6, 139.1, 142.2, 149.2.

6,8-dibromo-2-(4-chloro-phenyl)-3-nitro-2H-chromene (26)

$^1$H NMR (CDCl$_3$, 300 MHz) δ (ppm)=6.68 (s, 1H), 7.41 (d, 1H, J=2.0 Hz), 7.43 (d, 2H, J=8.0 Hz), 7.49 (m, 2H, J=8.0 Hz), 7.67 (d, 1H, J=2.0 Hz), 7.98 (s, 1H).

6,8-dibromo-2-(4-nitro-phenyl)-3-nitro-2H-chromene (27)

$^1$H NMR (CDCl$_3$, 300 MHz) δ (ppm)=8.28 (d, 2H, J=8.3 Hz), 8.00 (s, 1H), 7.70 (dd, 1H, J=1.0 and 2.2 Hz), 7.58 (td, 2H, J=2.0 and 8.5 Hz), 7.44 (d, 1H, J=2.2 Hz), 6.80 (s, 1H).
$^{13}$C NMR (CDCl$_3$, 75 MHz) δ (ppm)=73.4, 112.4, 115.3, 120.3, 124.2, 127.8, 128.1, 131.8, 139.5, 142.4, 148.98.

2-(4-bromo-phenyl)-6-ethynyl-3-nitro-2H-chromene (32)

$^1$H NMR (CDCl$_3$, 300 MHz) δ (ppm)=3.06 (s, 1H), 6.54 (s, 1H), 6.82 (d, 1H, J=6.0 Hz), 7.23 (m, 2H), 7.45 (m, 4H), 8.00 (s, 1H).
$^{13}$C NMR (CDCl$_3$, 75 MHz) δ (ppm)=155.4, 141.3, 137.9, 135.4, 133.9, 132.1, 128.7, 128.5, 124.0, 117.8, 117.5, 116.7, 81.8, 73.9.

6-bromo-2-phenyl-2H-chromene-3-carbaldehyde (33)

$^1$H NMR (CDCl$_3$, 300 MHz) δ (ppm)=6.32 (s, 1H), 6.76 (d, 1H, J=8.2 Hz), 7.27-7.32 (m, 5H), 7.34-7.38 (m, 3H), 9.65 (s, 1H).

6-bromo-2-(4-fluoro-phenyl)-2H-chromene-3-carbaldehyde (34)

$^1$H NMR (CDCl$_3$, 300 MHz) δ (ppm)=6.29 (s, 1H), 6.76 (d, 1H, J=8.8 Hz), 6.97 (m, 2H), 7.27-7.32 (m, 3H), 7.38 (m, 3H), 9.65 (s, 1H).

8-ethoxy-2-phenyl-2H-chromene-3-carbaldehyde (35)

$^1$H NMR (CDCl$_3$, 300 MHz) δ (ppm)=1.37 (t, 3H, J=7.0 Hz), 4.04 (q, 2H, J=3.9) 6.43 (s, 1H) 6.86 (m, 2H), 6.92 (m, 1H, J=5.3 Hz), 7.25 (m, 3H), 7.35 (m, 2H), 7.38 (s, 1H); 9.67 (s, 1H).

6-bromo-3-nitro-2-(tetrahydro-pyran-4-yl)-2H-chromene (36)

$^1$H NMR (CDCl$_3$, 300 MHz) δ (ppm)=1.45 (m, 2H), 1.68 (m, 2H), 2.07 (m, 1H); 3.27 (m, 2H), 3.95 (m, 2H); 5.48 (d, 1H, J=6.4 Hz), 6.85 (d, 1H, J=8.6 Hz), 7.40 (d, 1H, J=2.3 Hz), 7.45 (dd, 1H, J=8.6 and 2.3 Hz), 7.79 (s, 1H).

8-bromo-3-nitro-2-(tetrahydro-pyran-4-yl)-2H-chromene (37)

$^1$H NMR (CDCl$_3$, 300 MHz) δ (ppm)=1.45 (m, 2H); 1.83 (m, 2H), 2.07 (m, 1H), 3.28 (m, 2H), 3.97 (m, 2H), 5.60 (d, 1H, J=6.7 Hz), 6.91 (t, 1H, J=7.7 Hz), 7.24 (dd, 1H, J=6.2 and 1.4 Hz), 7.58 (dd, 1H, J=6.5 and 1.5 Hz), 7.86 (s, 1H).

6,8-dibromo-3-nitro-2-(tetrahydro-pyran-4-yl)-2H-chromene (39)

$^1$H NMR (CDCl$_3$, 300 MHz) δ (ppm)=1.43 (m, 2H), 1.76 (m, 2H), 2.05 (m, 1H, H-5), 3.28 (m, 2H), 3.98 (m, 2H), 5.59 (d, 1H, J=6.6 Hz), 7.37 (d, 1H, J=2.2 Hz), 7.71 (d, 1H, J=2.2 Hz), 7.78 (s, 1H).

6-bromo-8-methoxy-3-nitro-2-(tetrahydro-pyran-4-yl)-2H-chromene (40)

$^1$H NMR (CDCl$_3$, 300 MHz) δ (ppm)=1.49 (m, 2H), 1.72 (m, 2H), 2.04 (m, 1H), 3.26 (m, 2H), 3.89 (s, 3H); 3.98 (m, 2H), 5.53 (d, 1H, J=6.86 Hz), 7.04 (d, 1H, J=2.1 Hz), 7.07 (d, 1H, J=2.1 Hz), 7.78 (s, 1H).

6-Bromo-2-(4-bromophenyl)-2H-chromene-3-carbaldehyde (44)

Mp=144-146° C. $^1$H-NMR (CDCl$_3$, 300 MHz) δ 6.27 (s, 1H), 6.76 (d, J=8.5, 1H), 7.19 (d, J=8.5, 2H), 7.35-7.40 (m, 4H), 7.43 (s, 1H), 9.66 (s, 1H). $^{13}$C-NMR (CDCl$_3$, 75 MHz) δ 73.7, 113.9, 119.0, 121.5, 123.0, 128.5, 131.5, 131.8, 134.0, 136.2, 137.4, 139.2, 153.4, 189.6.

2-(4-Bromo-phenyl)-3-nitro-2H-chromen-6-ol (45)

MMJ $^1$H-NMR (300 MHz, CDCl$_3$) δ 6.47 (s, 1H), 6.71-6.86 (m, 2H), 6.80 (s, 1H), 7.22 (d, J=8.5, 2H), 7.44 (d, J=8.5, 2H), 7.97 (s, 1H). $^{13}$C-NMR (75 MHz, CDCl$_3$) δ 73.2, 115.6, 118.1, 118.4, 121.6, 123.5, 128.7, 129.6, 131.9, 135.6, 141.3, 146.6, 151.6.

Compound (47)

MJ/4/140-1

¹H NMR (500 MHz, CDCl₃) δ 1.39-1.47 (m, 2H), 1.62-1.74 (m, 4H), 1.93-2.02 (m, 2H), 2.21 (t, J=7.4, 2H), 2.68 (d, J=12.8, 1H), 2.84-2.88 (dd, J=4.7, 12.8, 1H), 3.08-3.14 (m, 1H), 3.38-3.45 (m, 2H), 3.96 (t, J=6.0, 2H), 4.24-4.27 (m, 1H), 4.41-4.45 (m, 1H), 5.57 (bs, 1H), 6.44 (t, J=5.6, 1H), 6.47 (s, 1H), 6.53 (bs, 1H), 6.77 (d, J=8.6, 1H), 6.85 (t, J=2.7, 1H), 6.88 (dd, J=2.9, 8.6, 1H), 7.21 (d, J=8.4, 2H), 7.43 (d, J=8.4, 2H), 8.02 (s, 1H). ¹³C NMR (125 MHz, CDCl₃) δ 25.6, 28.0, 28.1, 29.1, 35.8, 36.9, 40.5, 55.6, 60.3, 61.8, 66.7, 73.3, 114.6, 114.6, 118.1, 118.4, 121.4, 121.4, 123.5, 128.7, 129.7, 131.9, 135.6, 141.2, 147.2, 154.0, 163.9, 173.6.

Compound (48)

MJ/4/188-2

1H NMR (500 MHz, CDCl3) δ 1.38-1.44 (m, 2H), 1.60-1.74 (m, 4H), 1.94-1.99 (m, 2H), 2.21 (t, J=7.2, 2H), 2.68 (d, J=12.7, 1H), 2.84-2.88 (m, 1H), 3.09-3.13 (m, 1H), 3.38-3.41 (m, 2H), 3.94 (t, J=5.8, 2H), 4.24-4.27 (m, 1H), 4.41-4.45 (m, 1H), 5.51 (bs, 1H), 6.41 (bs, 1H), 6.53 (bs, 1H), 6.60 (s, 1H), 6.84 (t, J=2.2, 1H), 7.11 (d, J=2.0, 1H), 7.25 (dd, J=2.2, 8.6, 2H), 7.44 (d, J=8.6, 2H), 8.02 (s, 1H). 13C NMR (125 MHz, CDCl3) δ 25.5, 27.9, 28.0, 29.0, 35.8, 36.5, 40.5, 55.5, 60.1, 61.6, 66.7, 73.4, 111.5, 114.5, 114.5, 119.5, 123.6, 123.7, 123.7, 128.4, 129.2, 129.2, 131.9, 135.0, 142.0, 142.0, 144.0, 154.0, 163.9, 173.4.

Compound (49)

MJ/4/191-1

¹H NMR (500 MHz, CDCl₃) δ 1.37-1.47 (m, 4H), 1.57-1.63 (m, 2H), 1.69-1.74 (m, 2H), 3.50-3.53 (m, 2H), 3.95 (t, J=6.2, 2H), 6.56 (dd, J=2.2, 8.6, 2H), 6.60 (d, J=8.6, 2H), 6.67 (d, J=2.2, 2H), 6.72 (s, 1H), 7.17 (d, J=8.2, 1H), 7.26 (d, J=2.7, 1H), 7.28 (d, J=2.7, 1H), 7.34 (d, J=8.5, 2H), 7.57 (d, J=8.5, 2H), 7.71-7.74 (m, 1H), 8.07 (bs, 1H), 8.22 (s, 1H), 8.38 (s, 1H), 9.85 (bs, 1H), 10.11 (s, 2H). ¹³C NMR (125 MHz, DMSO) δ 25.1, 26.0, 28.2, 28.4, 30.7, 35.7, 68.3, 72.8, 82.9, 102.1, 109.6, 110.2, 112.4, 115.8, 119.9, 122.7, 122.8, 128.9, 129.0, 129.7, 131.7, 135.3, 141.6, 142.8, 151.7, 153.8, 159.3, 162.2, 168.4.

6-Bromo-2-(4-bromophenyl)-3-nitro-2H-thiochromene (50)

¹H-NMR (CDCl₃, 300 MHz) δ 5.50 (s, 1H), 7.05 (d, J=8.6, 2H), 7.13 (d, J=8.4, 1H), 7.36 (d, J=8.6, 2H), 7.44 (dd, J=8.4, 2.2, 1H), 7.61 (d, J=2.2, 1H), 8.13 (s, 1H). ¹³C-NMR (CDCl₃, 75 MHz) δ 39.2, 119.7, 122.7, 127.8, 128.7, 129.8, 130.6, 131.0, 132.1, 134.2, 135.1, 138.3, 144.0.

6,8-Dibromo-2-(4-bromophenyl)-3-nitro-2H-thiochromene (51)

¹H-NMR (CDCl₃, 300 MHz) δ 5.59 (s, 1H), 7.06 (d, J=8.5, 2H), 7.38 (d, J=8.6, 2H), 7.57 (d, J=1.9, 1H), 7.71 (d, J=1.9, 1H), 8.10 (s, 1H). ¹³C-NMR (CDCl₃, 75 MHz) δ 40.1, 119.2, 122.1, 122.9, 127.9, 130.5, 130.8, 132.3, 133.1, 133.3, 138.1, 138.2, 144.1.

6,8-Dibromo-2-(4-bromophenyl)-2H-chromene-3-carbaldehyde (52)

¹H-NMR (CDCl₃, 300 MHz) δ 6.42 (s, 1H), 7.19 (d, J=8.2, 2H), 7.33 (s, 1H), 7.34 (d, J=2.2, 1H), 7.42 (d, J=8.2, 2H), 7.65 (d, J=2.2, 1H), 9.72 (s, 1H). ¹³C-NMR (CDCl₃, 75 MHz) δ 74.1, 112.2, 114.0, 122.6, 123.1, 128.2, 130.6, 131.8, 134.8, 136.8, 138.5, 138.6, 150.4, 189.3.

6-bromo-2-(4-bromophenyl)-2H-chromene-3-carboxylic acid (53)

Mp=208-210° C. ¹H-NMR (DMSO-d₆, 300 MHz) δ 6.23 (s, 1H), 6.78 (d, J=8.6, 1H), 7.22-7.32 (m, 2H), 7.38 (dd, J=8.6, 2.5, 1H), 7.50-7.60 (m, 2H), 7.66 (d, J=2.5, 1H), 7.74 (s, 1H). ¹³C-NMR (DMSO-d₆, 75 MHz) δ 74.0, 112.9, 118.6, 122.1, 122.5, 125.9, 129.3, 131.1, 131.9, 131.6, 134.4, 137.7, 151.6, 165.3.

6,8-dibromo-2(4-bromophenyl)-2H-chromene-3-carboxylic acid (54)

Mp=256-258° C. ¹H-NMR (DMSO-d₆, 300 MHz) δ 7.71 (d, J=2.3, 1H), 6.37 (s, 1H), 7.29 (d, J=8.4, 2H), 7.56 (d, J=8.5, 2H), 7.71 (d, J=2.3, 1H), 7.73-7.78 (m, 2H). ¹³C-NMR (DMSO-d₆, 75 MHz) δ 75.1, 111.5, 113.8, 122.8, 124.1, 127.3, 129.6, 131.2, 131.5, 132.2, 136.8, 137.8, 149.1, 165.5.

Methyl-6-Bromo-2-(4-bromophenyl)-2H-chromene-3-carboxylate (55)

Mp=118-120° C. ¹H-NMR (CDCl₃, 300 MHz) δ 3.77 (s, 3H), 6.22 (s, 1H), 6.67 (d, J=7.9, 1H), 7.21 (d, J=8.5, 2H), 7.27-7.31 (m, 2H), 7.41 (d, J=8.5, 2H), 7.59 (s, 1H). ¹³C-NMR (CDCl₃, 75 MHz) δ 52.2, 74.7, 113.7, 118.7, 122.0, 123.1, 125.1, 128.9, 131.1, 131.8, 132.2, 134.9, 137.5, 152.3, 164.7.

Methyl 6,8-Dibromo-2-(4-bromophényl)-2H-chromène-3-carboxylate (56)

¹H-NMR (CDCl₃, 300 MHz) δ 3.81 (s, 3H), 6.36 (s, 1H), 7.21-7.31 (m, 3H), 7.38-7.48 (m, 2H), 7.55 (d, J=2.2, 1H), 7.57 (s, 1H). ¹³C-NMR (CDCl₃, 75 MHz) δ 52.4, 75.0, 111.9, 113.9, 123.1, 123.2, 126.1, 128.7, 130.2, 131.8, 131.9, 137.0, 137.3, 149.4, 164.5.

6-Bromo-2-(4-bromophenyl)-N,N-dimethyl-2H-chromene-3-carboxamide (57)

¹H-NMR (CDCl₃, 500 MHz) δ 2.96 (s, 6H), 6.18 (s, 1H), 6.54 (s, 1H), 6.71 (d, J=8.6, 1H), 7.19 (d, J=2.4, 1H), 7.27 (d, J=1.3, 3H), 7.44 (d, J=8.4, 2H). ¹³C-NMR (CDCl₃, 125 MHz) δ 35.2, 38.5, 76.8, 113.5, 118.1, 121.8, 122.9, 123.2, 128.6, 130.0, 130.4, 131.8, 133.4, 137.9, 151.6, 167.8.

6,8-Bromo-2-(4-bromophenyl)-N,N-dimethyl-2H-chromene-3-carboxamide (58)

¹H-NMR (CDCl₃, 500 MHz) δ 2.99 (s, 6H), 6.29 (s, 1H), 6.56 (s, 1H), 7.15 (d, J=2.2, 1H), 7.22-7.34 (m, 2H), 7.44 (d, J=8.5, 2H), 7.52 (d, J=2.2, 1H). ¹³C-NMR (CDCl₃, 125 MHz) δ 35.3, 38.5, 111.3, 113.7, 122.9, 123.0, 123.1, 128.4, 129.2, 131.3, 131.8, 136.0, 137.3, 148.6, 162.3, 167.5.

6-Bromo-2-(4-bromophenyl)-2H-chromene-3-carbaldehyde oxime (59)

Mp=158-160° C. $^1$H-NMR (DMSO-d$_6$, 500 MHz) δ 6.28 (s, 1H), 6.74 (d, J=8.7, 1H), 7.09 (s, 1H), 7.29 (dd, J=8.5, 3.2, 3H), 7.47 (d, J=2.4, 1H), 7.49-7.57 (m, 2H), 7.97 (s, 1H), 11.44 (s, 1H). $^{13}$C-NMR (DMSO-d$_6$, 125 MHz) δ 74.3, 113.5, 119.0, 122.4, 124.3, 126.0, 130.0, 130.0, 130.2, 132.0, 133.0, 137.8, 147.6, 151.4.

6,8-Bromo-2-(4-bromophenyl)-2H-chromene-3-carbaldehyde oxime (60)

Mp=214-216° C. $^1$H-NMR (DMSO-d$_6$, 500 MHz) δ 6.43 (s, 1H), 7.10 (s, 1H), 7.30 (d, J=8.4, 2H), 7.52 (dd, J=17.8, 5.4, 3H), 7.62 (d, J=2.3, 1H), 8.01 (s, 1H), 11.57 (s, 1H). $^{13}$C-NMR (DMSO-d$_6$, 125 MHz) δ75.0, 111.4, 113.8, 122.6, 125.5, 125.5, 129.5, 129.9, 131.1, 132.0, 134.9, 137.4, 147.4, 148.3.

6-Bromo-2-(4-bromophenyl)-2H-chromene-3-carbonitrile (61)

Mp=136-138° C. $^1$H-NMR (CDCl$_3$, 500 MHz) δ 5.88 (s, 1H), 6.75 (d, J=8.6, 1H), 7.23 (s, 1H), 7.27 (d, J=2.3, 1H), 7.31 (d, J=8.4, 2H), 7.37 (dd, J=8.7, 2.4, 1H), 7.50-7.56 (m, 2H). $^{13}$C-NMR (CDCl$_3$, 125 MHz) δ 75.6, 107.8, 114.5, 116.1, 118.8, 120.7, 124.0, 128.8, 130.6, 132.3, 135.7, 135.7, 137.1, 151.9.

6,8-Dibromo-2-(4-bromophenyl)-2H-chromene-3-carbonitrile (62)

Mp=196-198° C. $^1$H-NMR (CDCl$_3$, 500 MHz) δ 6.01 (s, 1H), 7.23 (d, J=1.1, 2H), 7.33 (d, J=8.5, 2H), 7.54 (d, J=8.5, 2H), 7.63 (d, J=2.2, 1H). $^{13}$C-NMR (CDCl$_3$, 125 MHz) δ 75.8, 108.6, 112.1, 114.6, 115.8, 121.6, 124.1, 128.5, 129.8, 132.3, 135.2, 136.6, 138.3, 148.9.

8-Bromo-2-(4-bromo-phenyl)-3-nitro-2H-chromene-6-ol (63)

MJ/4/180-2

$^1$H NMR (500 MHz, CDCl$_3$) δ 5.16 (bs, 1H), 6.61 (s, 1H), 6.77 (d, J=2.9, 1H), 7.08 (d, J=2.9, 1H), 7.24 (d, J=8.5, 2H), 7.45 (d, J=8.5, 2H), 8.05 (s, 1H). $^{13}$C NMR (125 MHz, CDCl$_3$) δ 73.5, 111.6, 115.5, 119.7, 123.7, 124.4, 128.4, 128.7, 132.0, 135.0, 142.3, 144.1, 151.0.

EXAMPLES

Example 1

Cytotoxic Effect of the Compounds of Formula (I)

It has been shown that the Jurkat and CEM cell lines are addicted to the PI3K/AKT/mTOR signaling pathway to survive and to proliferate (Beneteau, M. et al. Localization of Fas/CD95 into the lipid rafts on down-modulation of the phosphatidylinositol 3-kinase signaling pathway. *Molecular cancer research: MCR* 6, 604-613, (2008); Pizon, M. et al. Actin-independent exclusion of CD95 by PI3K/AKT signalling: Implications for apoptosis. *European journal of immunology* 41, (2011)).

Protocol:
Leukemic T-cell lines Jurkat and CEM were incubated for 24 hours (see FIGS. 1, 2, 3, 4 and 5) or for 20 hours (see FIG. 6) with compounds of formula (I) and with compound A, at the indicated concentrations and cell death was assessed using the viability assay MTT, which estimates the metabolic state of the cell.

Results:
The results are shown in FIGS. 1, 2, 3, 4, 5 and 6. The compounds of formula (I) trigger a strong cell death signal in CEM and Jurkat cells as measured by MTT assay.

Figure 2:
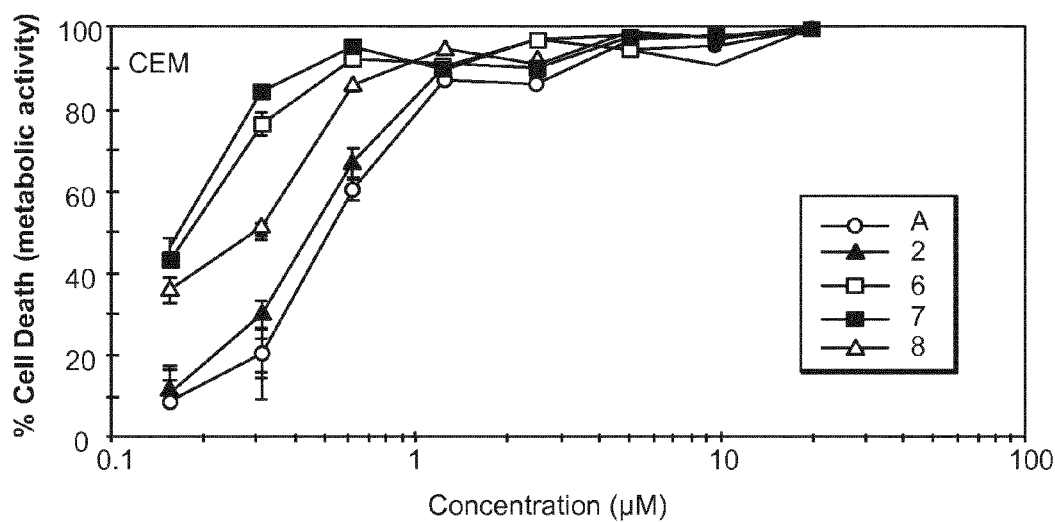
FIGS. 2, 3, 4 and 5 show the percentage of cell death of leucemic T-cells CEM, versus the concentration of some compounds of formula (I).

In FIGS. 1 and 2, compound A shows a lower percentage of cell death than most of the compounds of formula (I).

Figure 3:
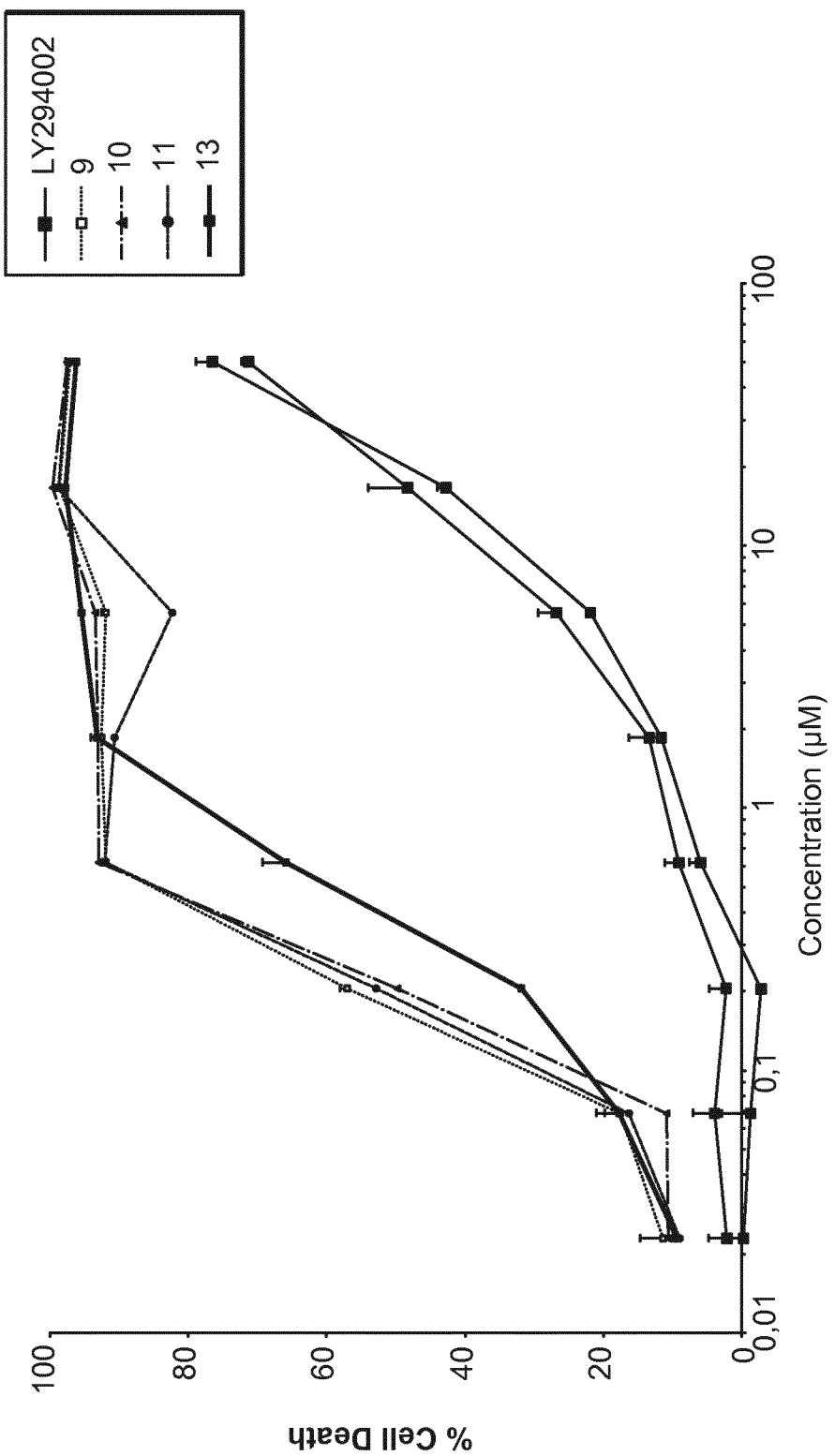
Figure 4:
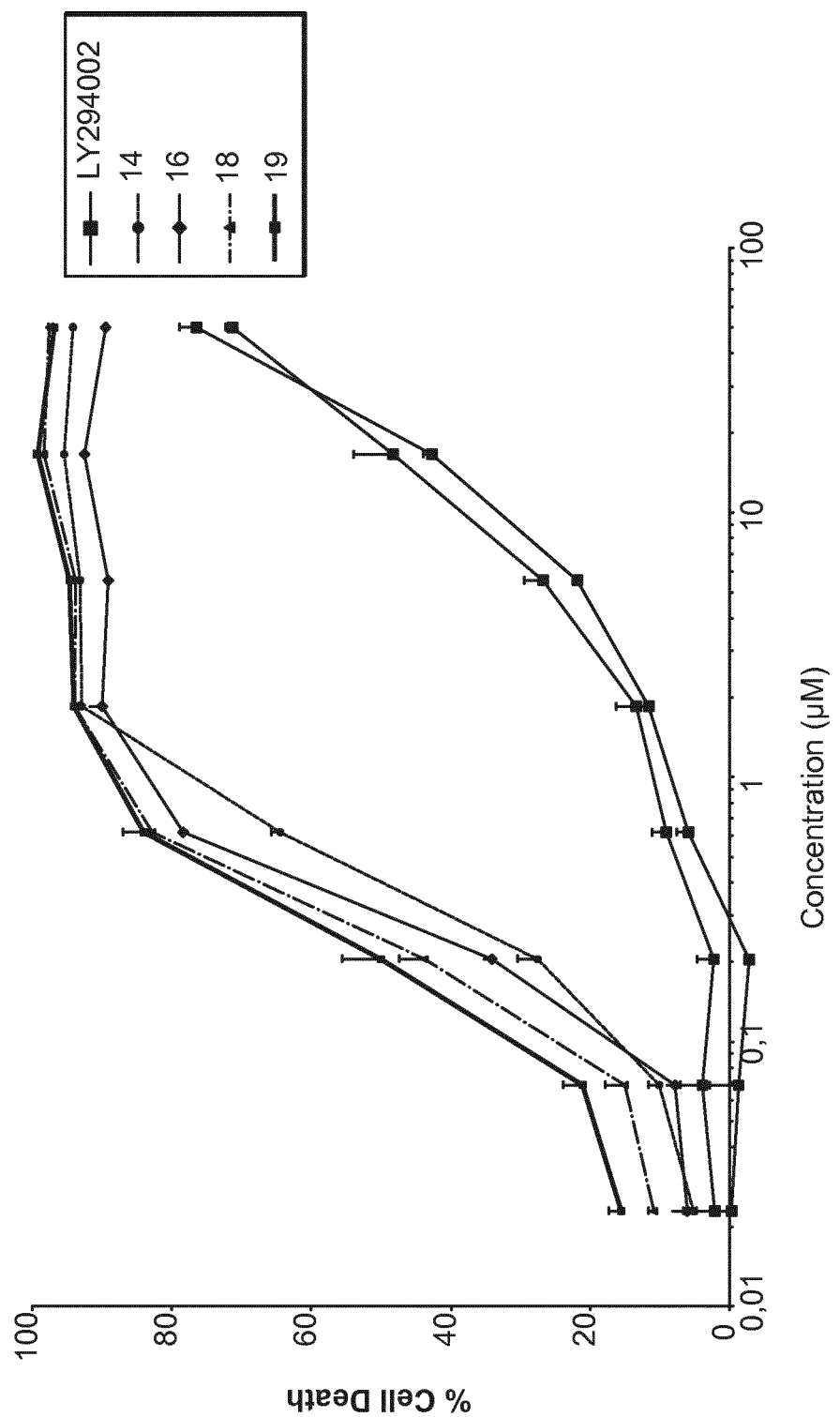
Figure 5:
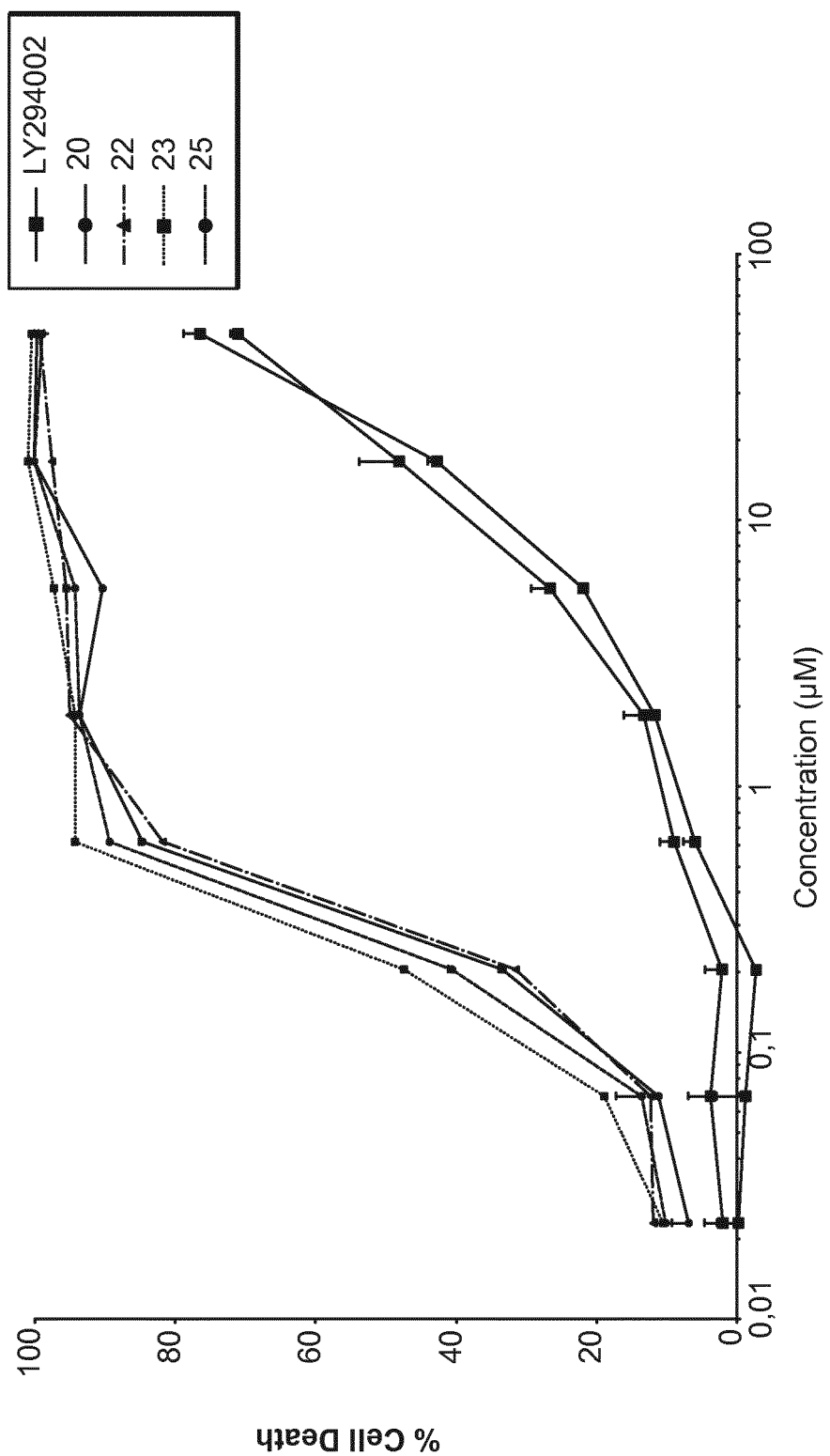
Figure 6:
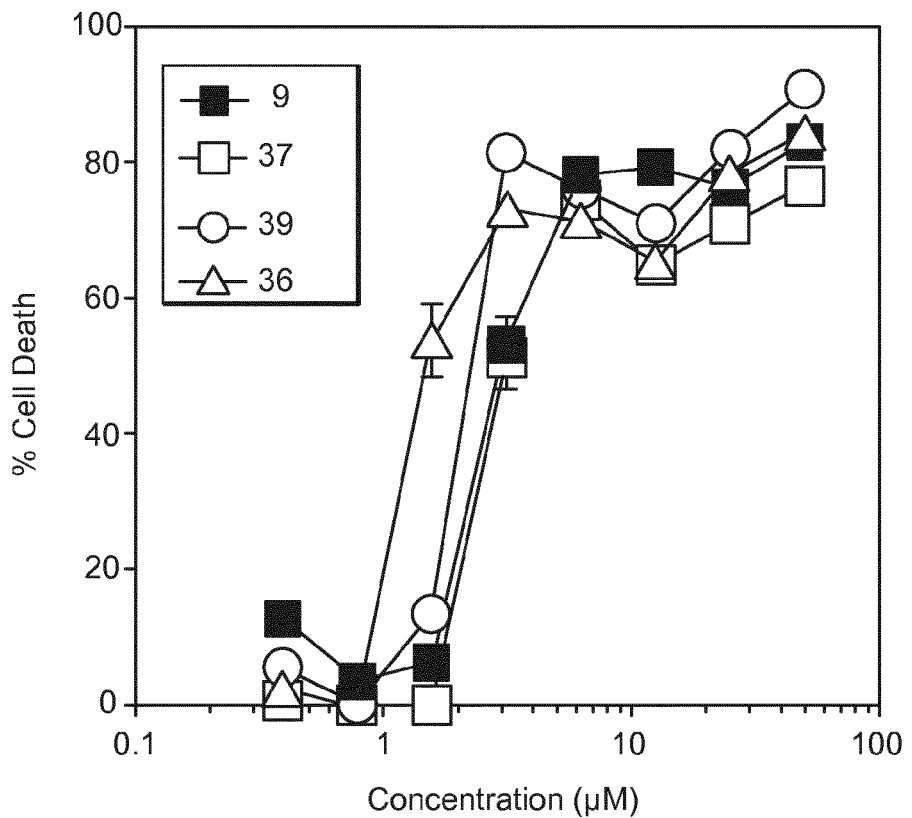

In FIGS. 3, 4 and 5, LY294002 shows a much lower cell death percentage than the compounds of formula (I).

These results demonstrate the strong cytotoxic activity of the compounds of formula (I), in comparison with other PI3K/AKT/mTOR pathway inhibitors such as compound A and LY294002.

Example 2

PI3K/AKT/mTOR Pathway Inhibitory Activity of the Compounds of Formula (I)

Protocol:
The CEM cell was incubated with 10 μM of each mentioned compound of formula (I) for the indicated times and then cells were lysed and 100 μg of protein was loaded per line and resolved by SDS-PAGE. The levels of AKT phosphorylation (hallmark of PI3K activation) and total AKT (loading control) were analyzed by Western blot and the amount of AKT phosphorylation relative to the total amount of protein AKT was quantified by densitometric analysis, the intensity of each band was scanned and the level of AKT phosphorylation was reported to the amount of whole AKT and the percentage of phosphorylated-AKT was depicted.

Figure 7:
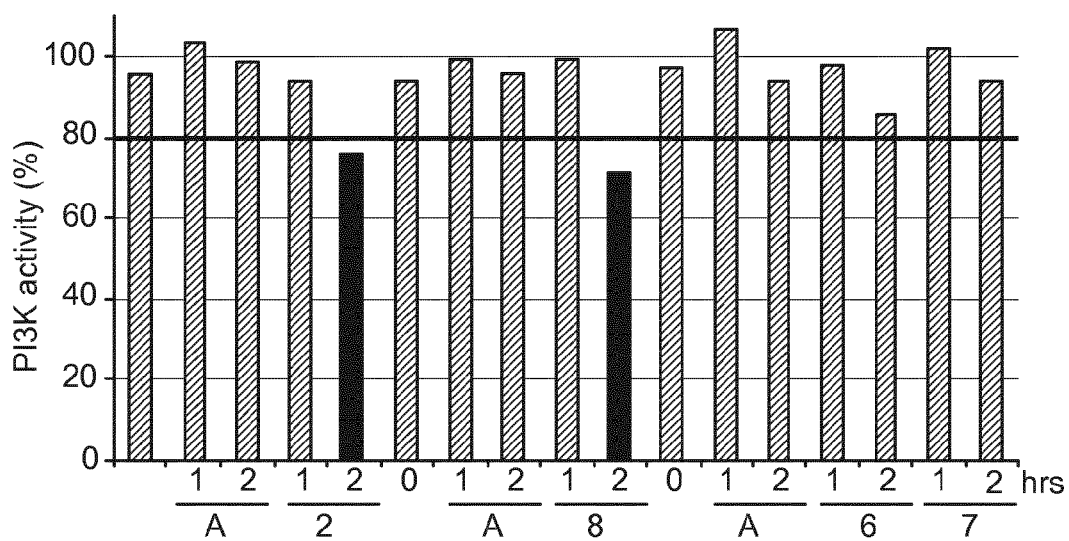
FIG. 7 and FIG. 8 show the PI3K activity, represented by the level of AKT phosphorylation, versus the time of incubation of CEM cells with compounds of formula (I) at a concentration of 10 μM.
Figure 8:
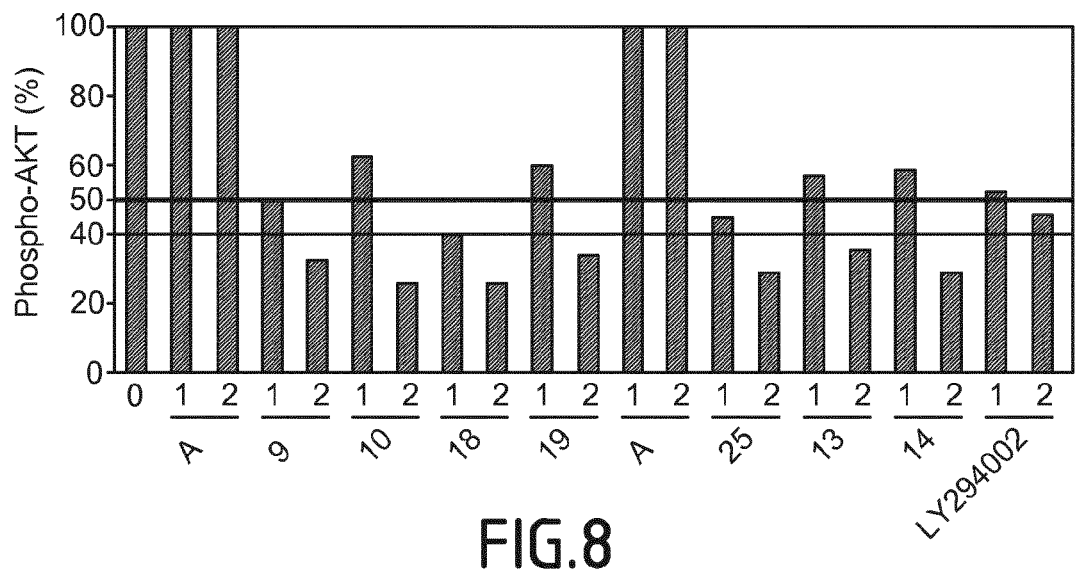

Results:
As shown in FIGS. 7 and 8 the compounds of formula (I) are very strong inhibitors of the PI3K/AKT activity, in particular the compounds 9, 10, 13, 14, 18, 19 and 25 (see FIG. 8). The other tested compounds also show a strong inhibitory activity (see FIG. 7).

It has to be noted that compound A, which has been described in prior art as PI3K inhibitor shows a very weak inhibitory activity on PI3K, even no inhibitory activity (see FIGS. 7 and 8). Moreover, as shown in FIG. 8, compounds of formula (I) show a stronger inhibitory activity on the PI3K/AKT/mTOR pathway than LY294002.

The results confirm that the compounds of the invention strongly inhibit the PI3K/AKT/mTOR pathway and are more potent than other PI3K/AKT/mTOR pathway inhibitors such as compound A and LY294002, especially much more potent than compound A.

Example 3

In Cellulo IC$_{50}$ of Compounds of Formula (I)

Protocol:
CEM cells were incubated for 2 hours with the indicated concentrations of each mentioned compound of formula (I).

Cells were then lysed and 100 µg of protein was loaded per line in an SDS-PAGE. Bands from AKT phosphorylation and whole AKT observed by Western blot were scanned and quantified by densitometric analysis. Based on these values, an in cellulo $IC_{50}$ (half maximal inhibitory concentration) was measured for each compound of formula (I).

The obtained $IC_{50}$ of the tested compounds are mentioned below in Table 1:

TABLE 1

| Compound | In vivo $IC_{50}$ (µM) |
|---|---|
| 9 | 0.4 |
| 10 | 2 |
| 13 | 8 |
| 14 | 10 |
| 18 | 1.5 |
| 19 | >10 |
| 25 | 3 |
| LY294002 | >10 |

It is noteworthy that among the tested compounds, the most effective reagent designated compound 9, possesses an in cellulo $IC_{50}$ at 0.4 µM, which is much more efficient than the LY294002 $IC_{50}$, which is higher than 10 µM.

Example 4

Compounds of Formula (I) as Potent Inducers of Cell Death in Triple Negative Breast Cancer Cells Protocol:
The Triple-negative tumor cell lines MDA-MB-231 and MDA-MB-468 were incubated with the indicated concentrations of each mentioned compound of formula (I) for 24 hours and then cell death was assessed using MTT assay.

Figure 9:
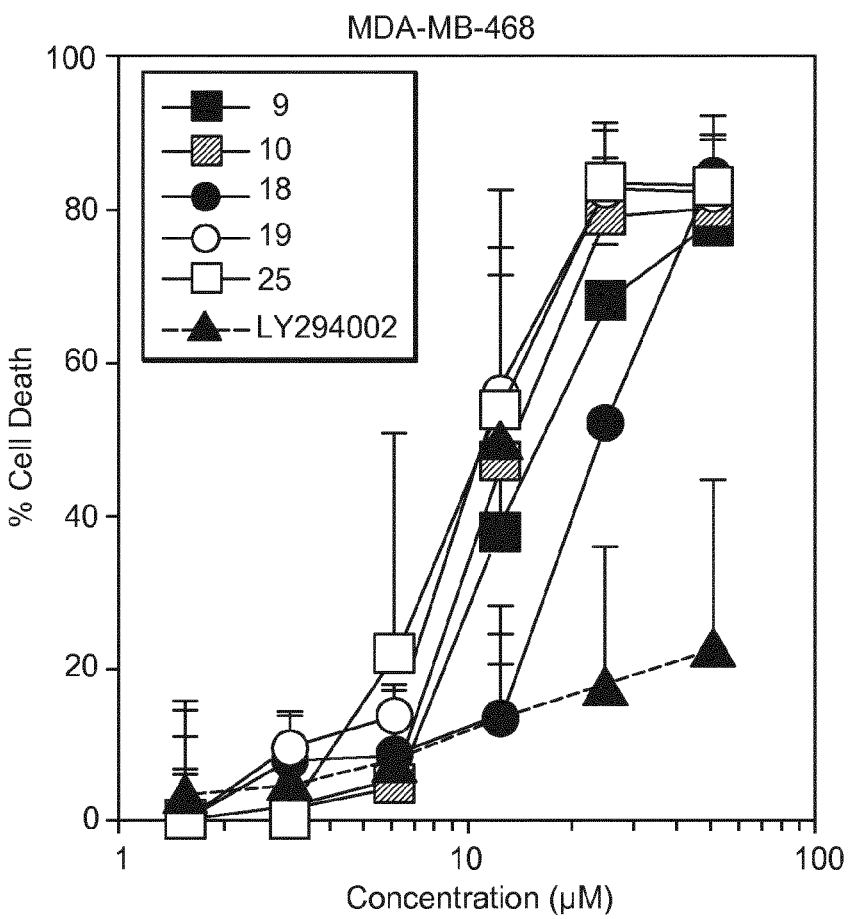
FIG. 9 and FIG. 10 show the percentage of cell death of triple-negative breast cancer cells (respectively MDA-MB-468 and MDA-MB-231 cell lines), versus the concentration of some compounds of formula (I).
Figure 10:
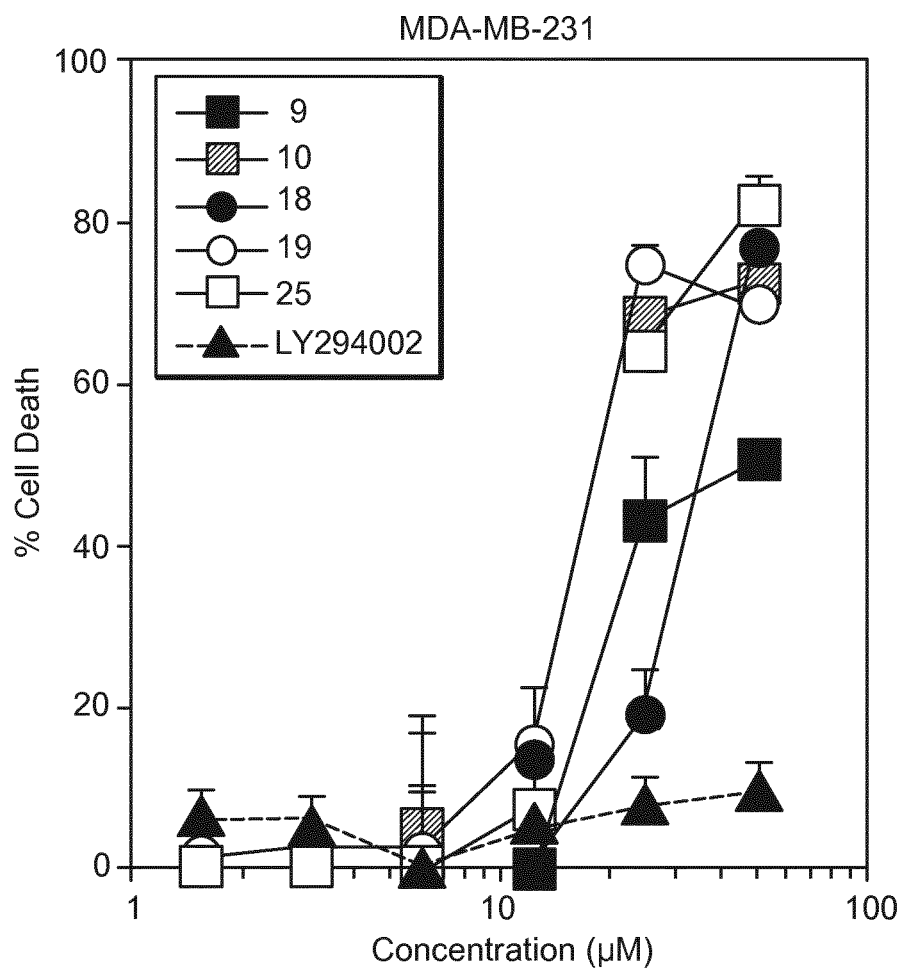
Figure 11:
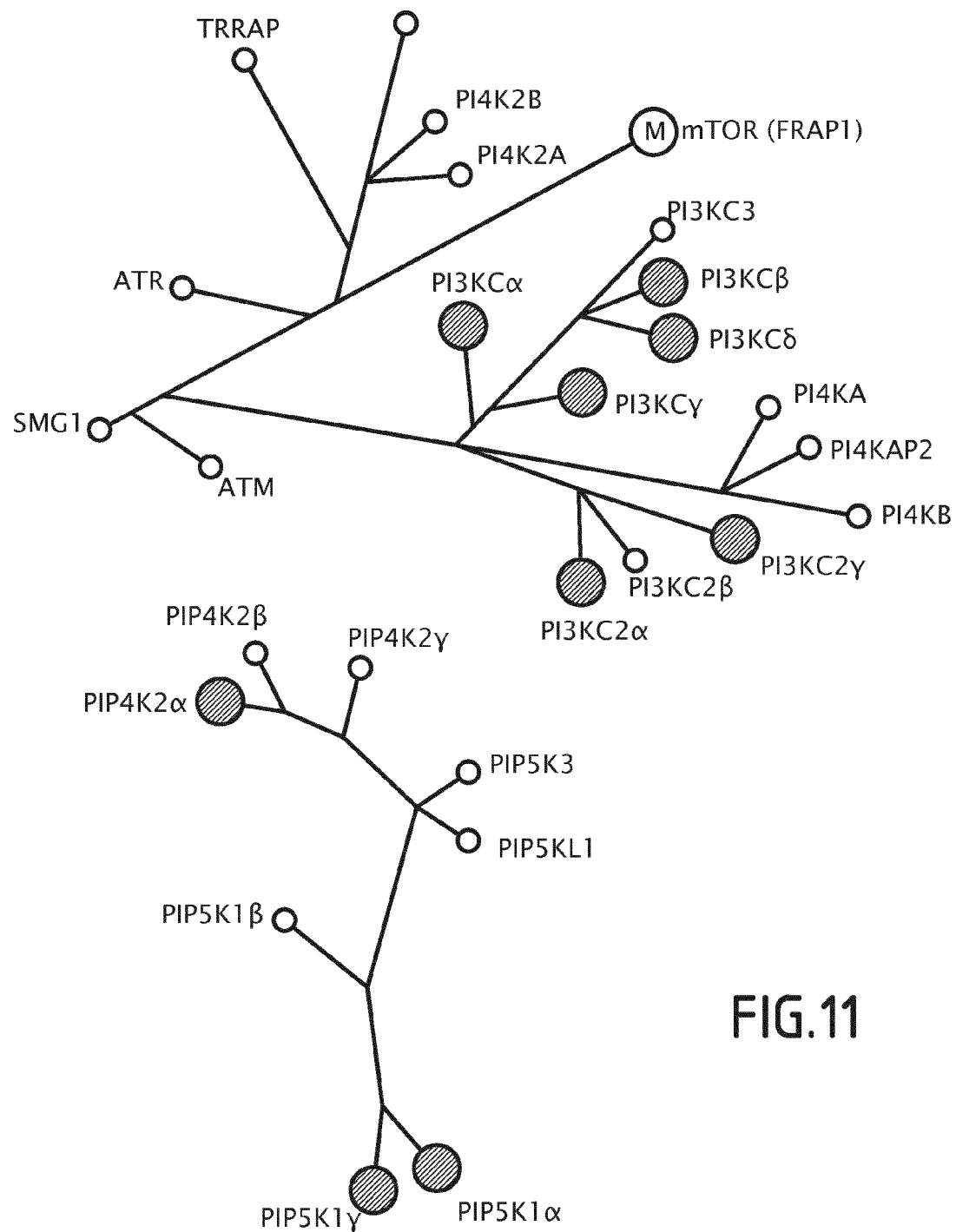
FIG. 11 shows a part of the kinome perfomed by KinaseProfiler™ with compound 25 at 1 μM. It shows the selectivity of compound 25 for the mTOR protein regarding 243 human kinases.
Figure 12:
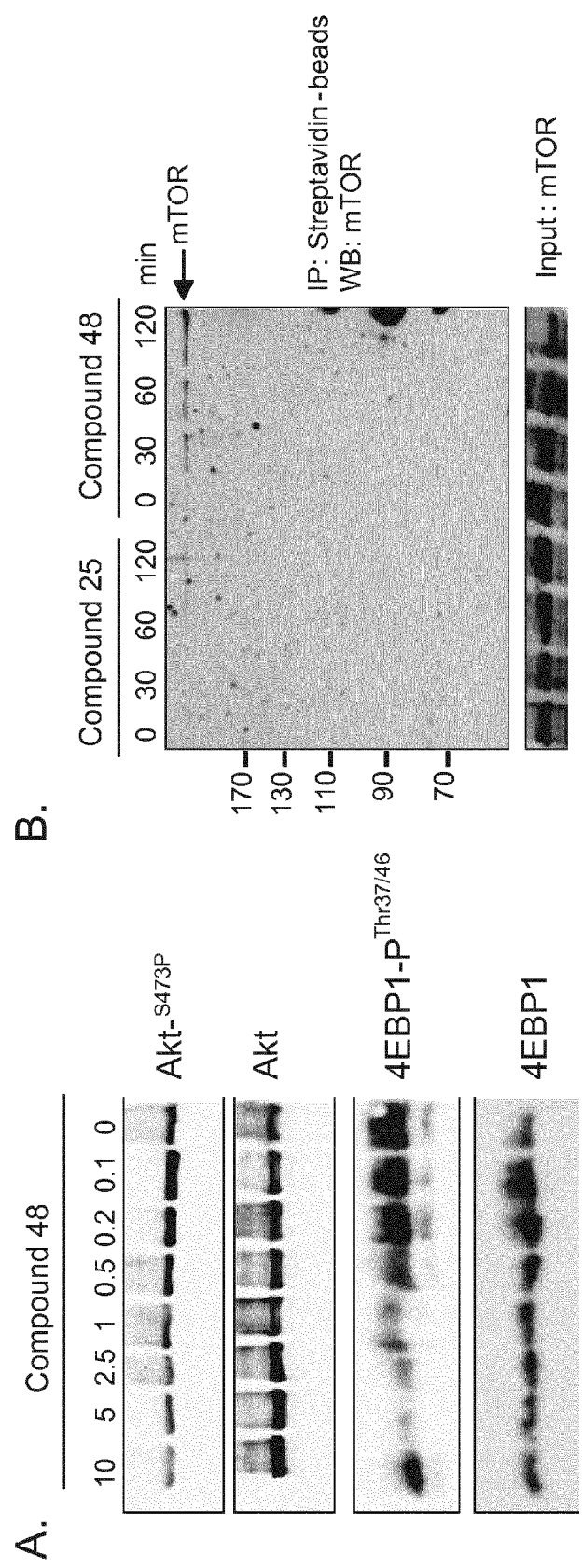
FIG. 12 shows the binding of compound 48 to mTOR and its inhibitory activity.

Results:
In contrast to LY294002, the compounds of formula (I) implement a strong cell death signal in triple-negative breast tumor cells MDA-MB-231 and MDA-MB-468 (see FIGS. 9 and 10). These results confirm that compounds of formula (I) are of interest to prevent and/or treat breast cancers, especially triple-negative breast cancer.

Example 5

Compounds of Formula (I) as Potent Inducers of Cell Death in Non-Triple Negative Breast Cancer Cells Protocol:
The ER-positive breast tumor cell lines MCF-7 and T47-D and the HER2 positive breast tumor cell lines MDA-MB-453 and BT474 (also ER-positive) were incubated with the indicated concentration of each mentioned compound of formula (I) for 24 hours and then cell death was assessed using MTT assay.

Results:
The results are shown in Tables below:
For each cell line, the percentage of cell death (mean of four experiments for cell lines MCF-7 and T47-D, and two experiments for cell lines MDA-MB-453 and BT474) is given in view of the increasing concentration of each tested compound of the invention.

| Cell line MCF-7 (ER-positive) | | | | | | |
|---|---|---|---|---|---|---|
| Concentration (µM) | percentage of cell death with compound 9 | percentage of cell death with compound 10 | percentage of cell death with compound 19 | percentage of cell death with compound 25 | percentage of cell death with compound 7 | percentage of cell death with LY294002 |
| 50 | 80.16 | 81.85 | 84.65 | 94.09 | 95.55 | 18.89 |
| 25 | 52.18 | 49.08 | 52.14 | 76.72 | 79.7 | 13.51 |
| 12.5 | 32.14 | 24.06 | 25.75 | 63.54 | 38.7 | 11.067 |
| 6.25 | 0 | 0 | 0 | 47.86 | 10.88 | 11.53 |

| Cell line T47-D (ER-positive) | | | | | | |
|---|---|---|---|---|---|---|
| Concentration (µM) | percentage of cell death with compound 9 | percentage of cell death with compound 10 | percentage of cell death with compound 18 | percentage of cell death with compound 25 | percentage of cell death with compound 7 | percentage of cell death with LY294002 |
| 50 | 93.62 | 92.93 | 78.28 | 91.25 | 88.3 | 55.69 |
| 25 | 91.2 | 91.71 | 23.71 | 90.23 | 92.07 | 50.01 |
| 12.5 | 92.97 | 87.84 | 0 | 91.27 | 85.1 | 40.42 |
| 6.25 | 20.53 | 4.62 | 0 | 85.31 | 34.43 | 32.33 |

| Cell line MDA-MB-453 (HER2 positive) | | | | | | | |
|---|---|---|---|---|---|---|---|
| Concentration (µM) | percentage of cell death with compound 9 | percentage of cell death with compound 10 | percentage of cell death with compound 18 | percentage of cell death with compound 19 | percentage of cell death with compound 25 | percentage of cell death with compound 7 | percentage of cell death with LY294002 |
| 50 | 98.67 | 99.07 | 100 | 101.13 | 100.76 | 100.25 | 86.55 |
| 25 | 97.49 | 98.46 | 93.72 | 98.05 | 99.35 | 102.46 | 76.61 |
| 12.5 | 87.47 | 93.07 | 81.73 | 91.89 | 95.09 | 97.05 | 53.74 |
| 6.25 | 71.22 | 76.17 | 45.963 | 53.93 | 89.213 | 65.61 | 17.45 |
| 3.125 | 53.8 | 70.42 | 0 | 24.69 | 85.57 | 52.93 | 0 |
| 1.5625 | 4.67 | 5.06 | 0 | 0 | 81 | 13.84 | 0 |
| 0.78125 | 7.56 | 7.8 | 3.17 | 0 | 9.09 | 0 | 0 |
| 0.390625 | 1.52 | 6.6 | 3.17 | 0 | 0 | 1.13 | 0 |

| Cell line BT474 (ER-positive/HER2-positive) | | | | | |
|---|---|---|---|---|---|
| Concentration (µM) | percentage of cell death with compound 9 | percentage of cell death with compound 10 | percentage of cell death with compound 25 | percentage of cell death with compound 7 | percentage of cell death with LY294002 |
| 50 | 93.62 | 93.84 | 96.81 | 96.07 | 77.2 |
| 25 | 88.01 | 69.52 | 90.49 | 91.87 | 62.79 |
| 12.5 | 71.4 | 40.42 | 95.61 | 55.3 | 48.7 |
| 6.25 | 25.95 | 0 | 75.54 | 44.85 | 35.35 |

The percentages of cell death induced by the compounds of formula (I) are higher than the percentages of cell death induced by LY294002 with concentrations from 6.25 to 50 µM. In some cases, the percentages of cell death induced by the compounds of formula (I) are higher than the percentages of cell death induced by LY294002 with concentrations from 0.390625 to 50 µM.

The compounds of formula (I) implement a strong cell death signal on tumor cells MCF-7, T47-D, BT474 and MDA-MB-453. These results confirm that compounds of formula (I) are of interest to prevent and/or treat breast cancers.

Example 6

Compounds of Formula (I) Inhibit the PI3K/Akt/mTOR Pathway and Bind to mTOR

FIG. 12A:

The inhibition of the phosphorylation level of AKT at serine 473, target of mTORC2, and 4EBP1 (also called Eukaryotic translation initiation factor 4E-binding protein 1) at threonines 37/46, which are targets of mTORC1, by compound 48 (compound 25 linked to biotin) was assessed by immunoblotting. Total AKT and 4EBP1 were added as loading controls.

These results show that the phosphorylation of AKT and 4EBP1 decreases with the increase in the compound 48 concentrations. These results show that the compounds of formula (I) inhibit the PI3K/AKT/mTOR pathway by inhibiting the phosphorylation of mTOR downstream effectors such as AKT and 4EBP1.

FIG. 12B:

Compounds 25 and 48 (compound 25 linked to biotin) (1 µM) were incubated with CEM leukemic T cells for indicated times. Then cells were lyzed in RIPA buffer and biotin was immunoprecipitated using streptavidin-coated magnetic beads. Beads were washed and the presence of mTOR was analyzed in compound 48-associated complex by Immunoblotting.

The results show that compound 48 binds to mTOR. Therefore, the compounds of formula (I) target the mTOR protein in tumor cell lines.

Example 7

Toxicity of the Compounds of the Invention in Vivo

The in vivo toxic activity of compound 25 was studied as follows.

Figure 13:
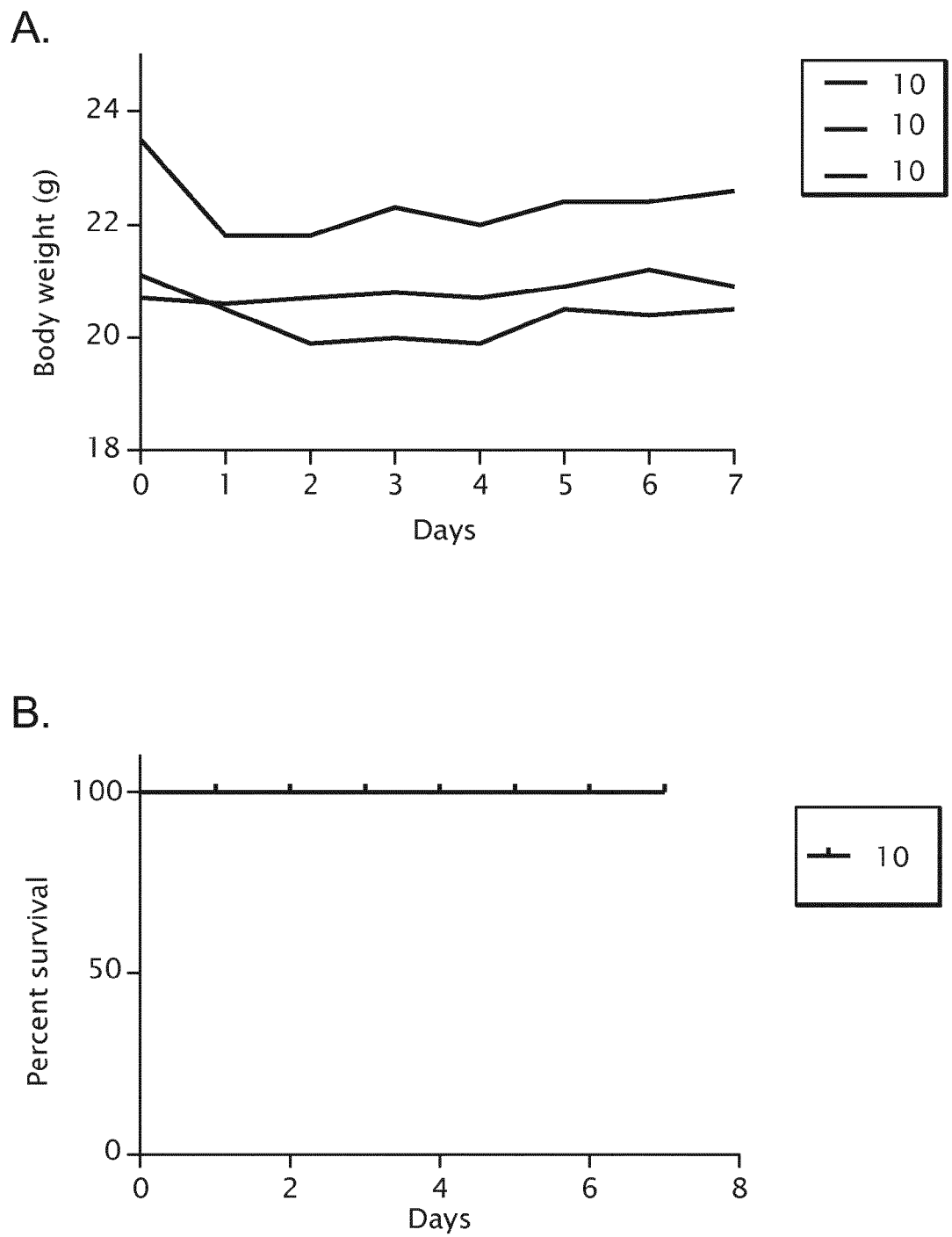
FIG. 13 shows the in vivo tolerance of compound 25 in mice.

Mice received repeated intravenous injections of compound 25 (10 mg/kg) or vehicle. The results show that treatment with compound 25 did not exhibit toxicity in mice: the body weight of the tested mice was maintained and all mice survived at 7 days (see FIGS. 13A and 13B).

Example 8

Figure 14:
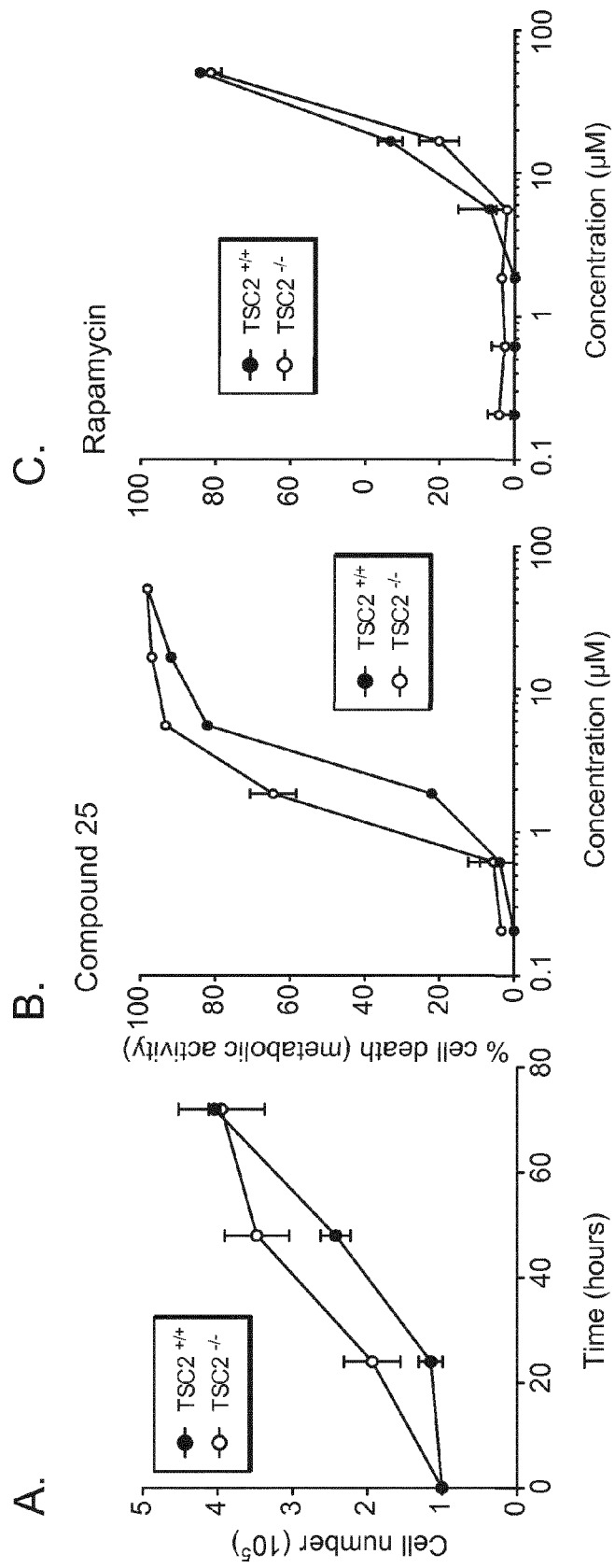
FIG. 14 shows the cytotoxic activity of the compounds of the invention on $TSC2^{-/-}$ and $TSC2^{+/+}$ cells.

Cytotoxic Activity of the Compounds of the Invention on $TSC2^{-/-}$ and $TSC2^{+/+}$ Cells AML (AngioMyoLipoma) cells from a patient (generous gift from Dr M. Pende, Paris) were enriched for $TSC2^{-/-}$ cells, as a model of tuberous sclerosis. These cells have been reconstituted with wild type TSC2 ($TSC2^{+/+}$). Cell proliferation was assessed in cells from angiomyolipomas and their counterparts reconstituted with wild type TSC2. FIG. 14A shows the cell number obtained over time.

Cell viability was assessed by MTT assay. Cells were incubated for 16 hours in a 1% fetal calf serum-containing medium supplemented with the indicated concentrations of the two mTOR inhibitors, compound 25 or rapamycin (see FIGS. 14B and 14C). Data represent mean and standard deviation of three independent experiments.

These results show that $TSC2^{-/-}$ cells are more sensitive to compound 25 than wild type $TSC2^{+/+}$. Moreover, the compound 25 of the invention is more efficient to kill $TSC2^{-/-}$ cells than rapamycin, which is used in the treatment of tuberous sclerosis.

Thus, the compounds of the invention are useful to treat tuberous sclerosis and are more efficient than rapamycin.

Example 9

The Compounds of the Invention Inhibit mTORC1 Activity in $TSC2^{-/-}$ Cells

Figure 15:
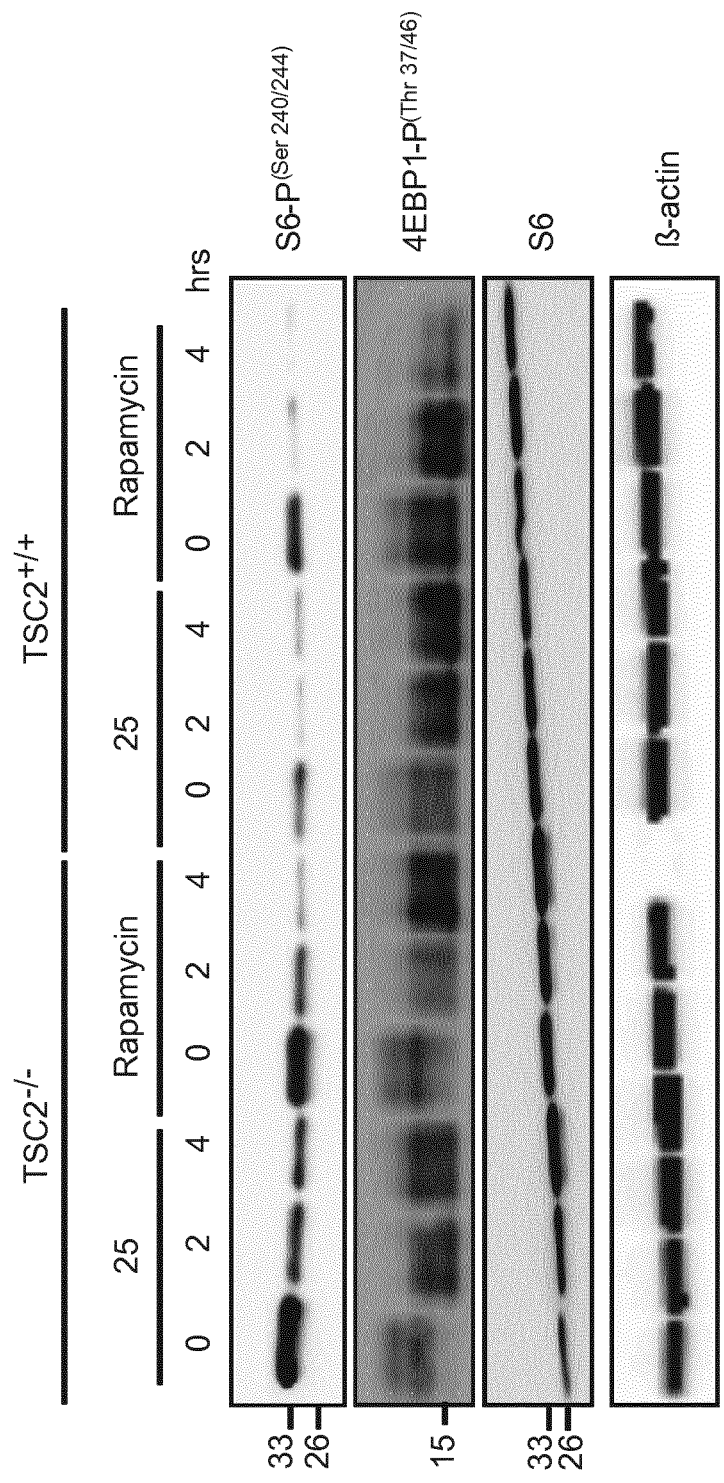
FIG. 15 shows the results of an immunoblot demonstrating that compound 25 inhibits mTORC1 activity in $TSC2^{-/-}$ cells.

AML cells ($1.10^6$ cells) deficient for TSC2 ($TS2^{-/-}$) or reconstituted with wild type TSC2 ($TSC2^{+/+}$) (generous gift from Dr M. Pende, Paris) were treated or untreated for indicated times with 10 µM of compound 25 or rapamycin and then cells were lyzed. 100 µg of protein was loaded and resolved by SDS-PAGE and indicated immunoblots were performed. Total S6 and β-actin serve as loading controls. S6 is phosphorylated by p70S6K on its serine 240 and 244. 4EBP1 is phosphorylated by mTORC1 on its Threonine at positions 37 and 46. p70S6K and 4EBP1 are direct substrates of mTORC1. mTORC1-driven phosphorylation of 4EBP1 can be monitored by the appearance of a high molecular weight band which disappears in presence of compound 25 or Rapamycin (see FIG. 15). Of note, restoration of TS2 expression in AML cells reduces the basal level of S6 and 4EBP1 phosphorylation.

These results show that compounds of the invention such as compound 25, inhibit mTORC1 activity in $TSC2^{-/-}$ cells.

Example 10

Competitive Inhibition of mTOR by the Compounds of the Invention

Unlike rapamycin, which when bound to FKBP12, interacts with and inhibits the kinase activity of mTORC1, competitive mTOR inhibitors target both mTORC1 and mTORC2.

Figure 16:
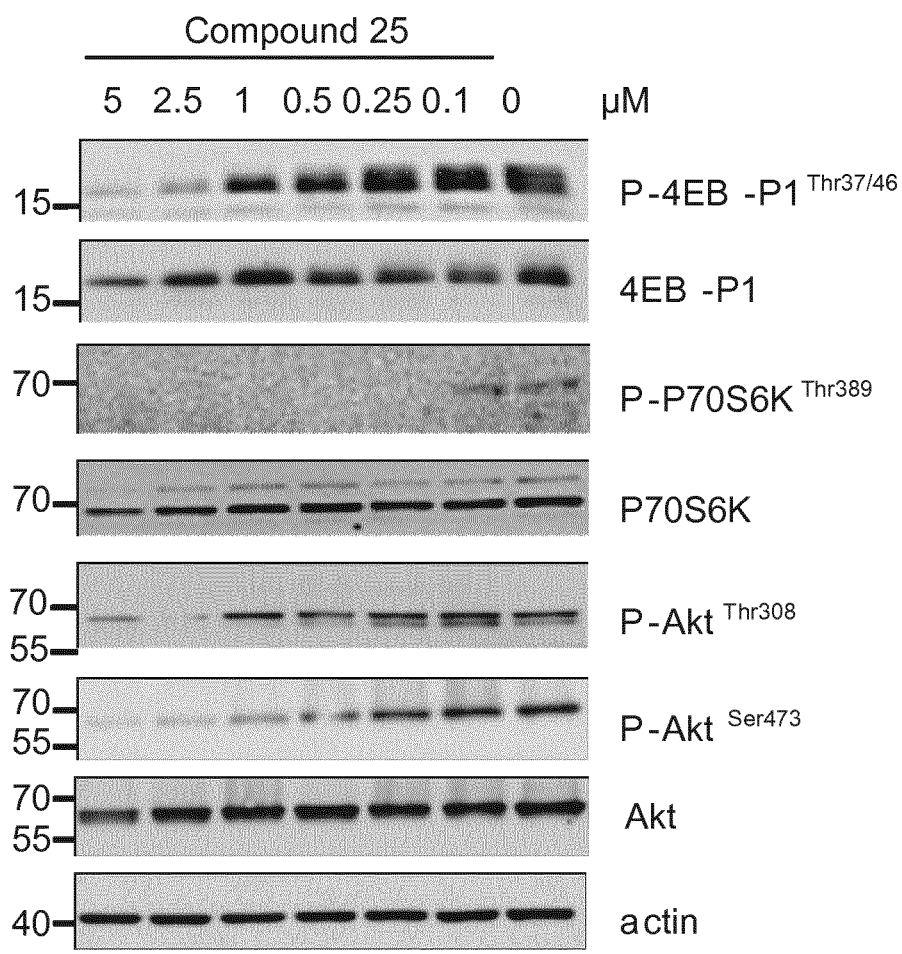
FIG. 16 shows the results of an immunoblot demonstrating that compound 25 inhibits mTORC1 and mTORC2 activities.

CEM cells ($1·10^6$ cells) were incubated with indicated concentrations of compound 25 for 2 hours and lysates of the cells were subjected to Western blot analysis. Inhibitory activity of compound 25 on mTORC1 substrates p70S6K-Thr389 and 4EBP1-Thr37 and 46 and on mTORC2 substrate Akt-Ser473 and on PDK1 substrate Akt-Thr308 was evaluated by immunoblotting. Total 4EBP1, p70S6K, Akt and 1-actin serve as loading controls. The compounds of the invention and more particularly compound 25 may be competitive inhibitors of mTOR because they inhibit mTORC1 (4EBP1 and p70S6K) and mTORC2 substrates (AKT at S473) as shown in FIG. 16.

Example 11

Prevention of Cell Migration by the Compounds of the Invention in Triple Negative Breast Cancer (TNBC) Cells CD95L (also known as FasL) belongs to the TNF (Tumor Necrosis Factor) family and is the ligand for the "death receptor" CD95 (Fas/APO1). This transmembrane cytokine can be cleaved by metalloproteases, to produce a soluble ligand. This naturally-processed CD95L (cl-CD95L) in patients affected by triple negative breast cancer triggers cancer cell migration and by doing so, enhances the risk of metastatic dissemination in these patients. Unlike membrane-bound-CD95L, cl-CD95L fails to induce apoptosis and instead promotes the formation of an atypical receptosome herein designated Motility-Inducing Signaling Complex (MISC).

MISC formation leads to the induction of the pro-oncogenic phosphoinositide 3-kinase (PI3K)/mammalian target of rapamycin (mTOR) signaling pathway.

TNBC (MDA-MB-231 and BT549) cell lines were pre-incubated for 1 hour in presence or absence of non-cytotoxic amount of compound 25 (1 µM) and then treated or untreated with CD95L (100 ng/ml) for 24 hours. Cell migration was analyzed using Boyden chamber assay. Migrating Giemsa-stained cells were lysed and absorbance was measured at a wavelength of 560 nm. Values represent the means±SEM of three independently performed experiments. *$p<0.05$ as calculated using two-tailed Mann-Whitney test.

Figure 17:
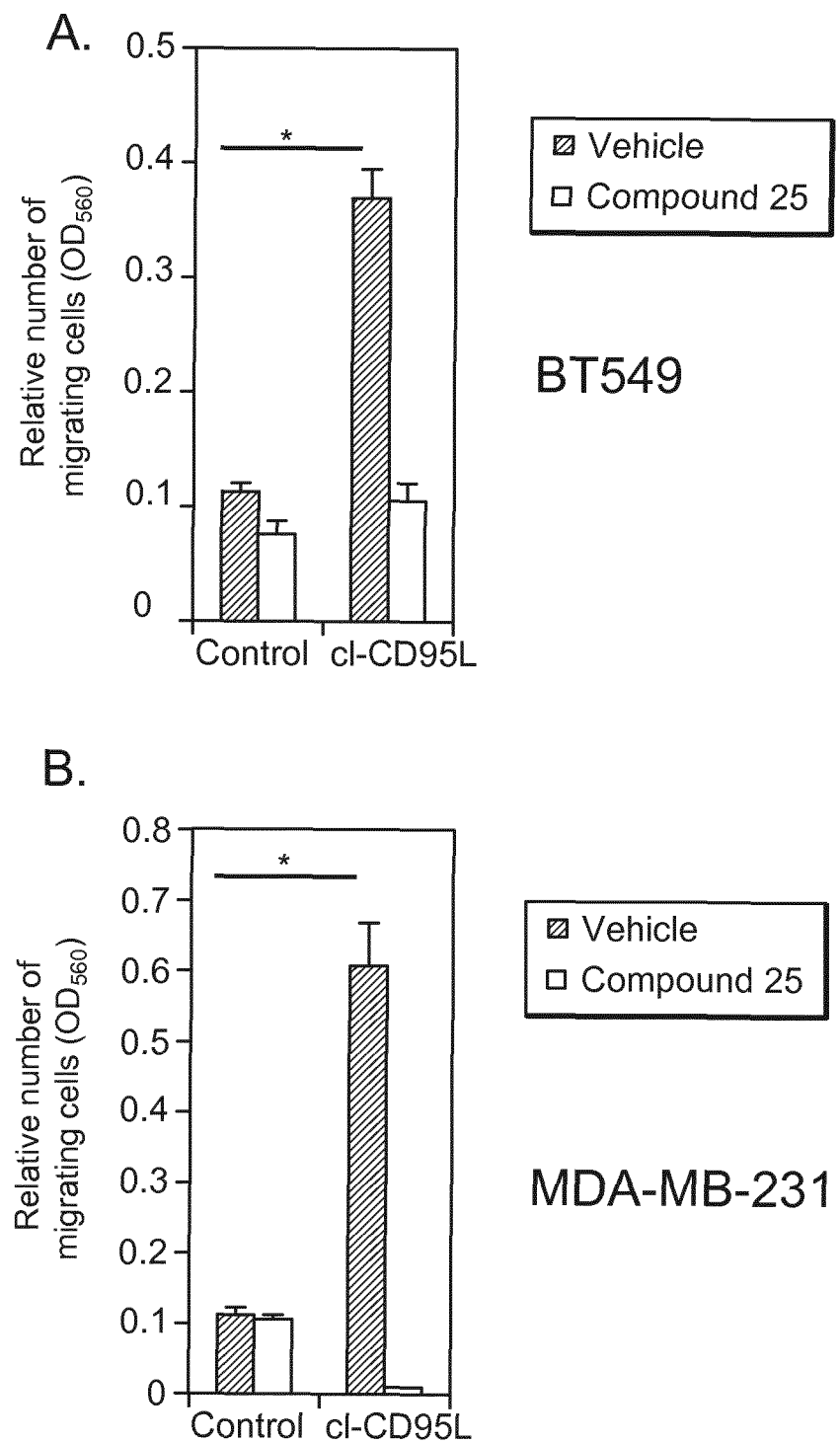
FIG. 17 shows that compound 25 inhibits cell migration of MDA-MB-231 cells (FIG. 17B) and of BT549 cells (FIG. 17A).

The results show that 1 µM of compound 25 was sufficient to abrogate the migration of the tumor cells stimulated with the pro-migratory factor CD95L (see FIG. 17).

Materiel and Methods of the Examples:

Antibodies and Other Reagents

LY294002 and Wortmannin were purchased from Calbiochem (Merck Chemicals Ltd., Nottingham, UK). Anti-mTOR, anti-4EBP, anti-phospho-4EBP, anti-AKT and anti-phospho-AKT antisera were from Cell Signaling Technology, Inc (Boston, Mass., USA).

Cell Lines

The human leukemic T-cell lines Jurkat and CEM and the lymphoma T-cell lines H9 were cultured in RPMI supplemented with 8% (v/v) heat-inactivated FCS and 2 mM L-glutamine at 37° C. in a 5% $CO_2$ incubator. The human breast cancer cell lines BT549, BT474, MDA-MB-231, MDA-MB-468, MDA-MB-453, T47D, and MCF7 were cultured in DMEM supplemented with 8% v/v heat-inactivated fetal calf serum (FCS) and 2 mM L-glutamine at 37° C. in a 5% $CO_2$ incubator. All cells were from American Type Culture Collection (ATCC, LGC Standards, Molsheim, France).

Compound 25-Biotine (Compound 48) Immunoprecipitation

CEM cells ($10^7$ cells) were pre-incubated for indicated times with 1 µM of compound 25 or compound 48, washed with PBS and lysed using RIPA buffer [50 mM Tris pH7.4, 1% NP-40, 0.5% Na-deoxycholate, 0.1% SDS, 150 mM NaCl, 2 mM EDTA, inhibitors of protease and phosphatase (Sigma)]. Next, compound 48 was immunoprecipitated using streptavidin-coated magnetic beads (Ademtech, Bordeaux, France) and after extensive washing, the immune complex was resolved by SDS-PAGE and mTOR was revealed by western blot.

Immunoblots Excepted for immunoprecipitation experiments in which cells were lyzed with RIPA buffer, cells were lyzed for 30 min at 4° C. in Lysis buffer (25 mM HEPES pH 7.4, 1% v/v Triton X-100, 150 mM NaCl, 2 mM EGTA supplemented with a mix of protease inhibitors). Protein concentration was determined by the bicinchoninic acid method (Pierce, Rockford, Ill., USA) according to the manufacturer's protocol. Proteins were resolved by 8, 10 or 12% SDS-PAGE and transferred to a nitrocellulose membrane (GE Healthcare, Buckinghamshire, UK). The membrane was blocked 15 min with TBST (50 mM Tris, 160 mM NaCl, 0.05% v/v Tween 20, pH 7.4) containing 5% w/v dried skimmed milk (TBS™). Primary antibody was incubated overnight at 4° C. in TBS™. The membrane was intensively washed (TBST) and then the peroxydase-labeled anti-mouse IgG1 or IgG2a (CliniSciences, Nanterre, France) was added for 45 min. Proteins were visualized with the enhanced chemiluminescence substrate kit (ECL RevelBIOt®, Ozyme, Saint Quentin en Yvelines, France).

Cell Death Assays

Cell viability was assessed using the 3-[4,5-dimethylthiazol-2-yl]-2,5-diphenyltetrazolium bromide (MTT) viability assay (1). In brief, cells ($4 \times 10^4$ per well) were cultured for 20 h in flat-bottomed 96 well plates with various concentrations of the apoptosis inducer. Then 0.015 ml of MTT (5 mg/ml in PBS) was added to each well and incubated for 4 h at 37° C. Formazan salt precipitats were dissolved by adding 0.115 ml of isopropyl alcohol containing 1% formic acid (v/v), and the absorbance was measured at 570 nm.

In Vitro Motility Assays

After membrane hydration of Boyden chambers (Millipore, Molsheim, France) containing 8 μm pore membranes, $10^5$ cells were added to the top chamber. The bottom chamber was filled with low serum (1%)-containing medium in the presence or absence of cl-CD95L (100 ng/ml). Breast cancer cells were incubated for 24 h. To quantify invasion, cells were fixed with methanol and stained with Giemsa. Stained cells were then removed from the top-side of the membrane using a cotton-tipped swab and five representative pictures for each insert were taken of the invading cells from the reverse side. For each experiment, invading cells were lysed and absorbance at 560 nm was measured.

REFERENCE

Weichert H, Blechschmidt I, Schroder S, Ambrosius H. The MTT-assay as a rapid test for cell proliferation and cell killing: application to human peripheral blood lymphocytes (PBL). Allerg Immunol (Leipz). 1991; 37:139-44.

The invention claimed is:

1. A compound having one of the following formulae:

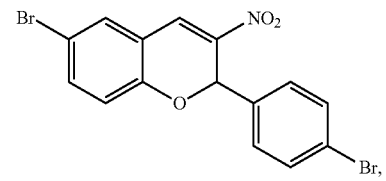

9

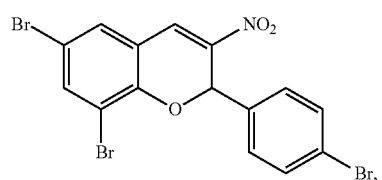

25

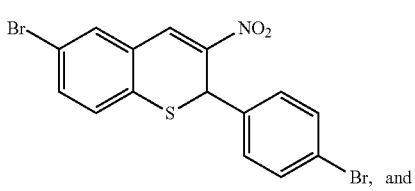

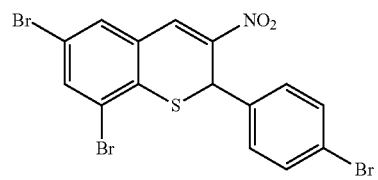

51 or its pharmaceutically acceptable salts, hydrates or hydrated salts or its polymorphic crystalline structures, racemates, diastereomers or enantiomers.

2. The compound according to claim 1, having the following formula:

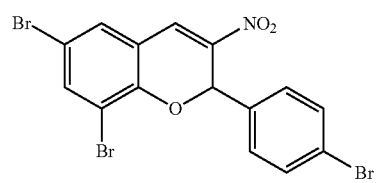

25 or its pharmaceutically acceptable salts, hydrates or hydrated salts or its polymorphic crystalline structures, racemates, diastereomers or enantiomers.

3. A method of treatment of a disease selected from the group consisting of: inflammatory diseases, autoimmune diseases, neurodegenerative diseases, cancers, transplant rejection and diseases characterized by a premature aging comprising administering a pharmaceutical acceptable amount of a compound of formula (I) as defined in claim 1 to a patient in need thereof.

4. The method according to claim 3, wherein the disease is selected among cancers.

5. The method according to claim 4, wherein the cancer is breast cancer.

6. A method of treatment of tuberous sclerosis comprising administering a pharmaceutical acceptable amount of a compound having formula (I):

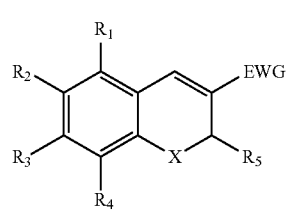

(I)

wherein:

X is O or S;

$R_1$, $R_2$, $R_3$ and $R_4$ are independently selected from the group consisting of:

H, ($C_1$-$C_{10}$)alkyl, ($C_1$-$C_{10}$)alkoxyl, ($C_2$-$C_{10}$)alkenyl, ($C_2$-$C_{10}$)alkynyl, OH, a fluorine atom, a bromine atom, a iodine atom, O($C_1$-$C_{10}$)alkylene-NHCO($C_1$-$C_{10}$)alkylene-($C_5$-$C_{10}$)heterocycloalkyl and O($C_1$-$C_{10}$)alkylene-NH—CS—NH—R" with R" being:

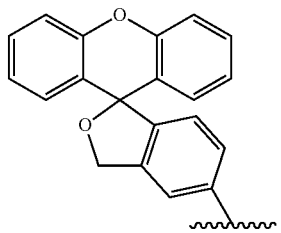

wherein:
R₂ and R₃ may form together with the carbon atoms to which $R_2$ and $R_3$ are attached to form a $(C_6-C_{10})$aryl group; and
R" and the $(C_5-C_{10})$heterocycloalkyl are optionally substituted by at least one substituent selected from OH and =O;
EWG is chosen selected from the group consisting of: $NO_2$, CHO, COR, CN, CN—OH, CONHR, CONRR' and COOR; R and R' being independently from each other chosen from $(C_1-C_{10})$alkyl groups;
$R_5$ is a $(C_6-C_{10})$aryl, a $(C_5-C_{10})$heteroaryl group, a $(C_3-C_{10})$cycloalkyl or a $(C_3-C_{10})$heterocycloalkyl group; said aryl and heteroaryl being optionally substituted by at least one substituent independently chosen from halogen, $(C_1-C_{10})$alkoxyl and nitro;
$R_5$ being different from the group:

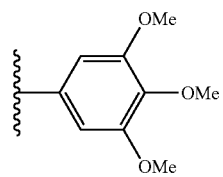 [SMILES: *c1cc(OC)c(OC)c(OC)c1]

and wherein when EWG is COOMe, one of $R_1$, $R_2$, $R_3$ or $R_4$ is different from H;
and provided that the compound of formula (I) is not:

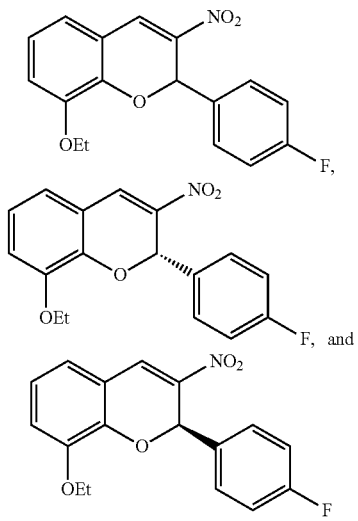

or its pharmaceutically acceptable salts, hydrates or hydrated salts or its polymorphic crystalline structures, racemates, diastereomers or enantiomers to a patient in need thereof.

7. The method of claim 6, wherein EWG is $NO_2$ or CHO.

8. The method of claim 6, wherein $R_1$ is H.

9. The method of claim 6, wherein $R_2$ is H, $(C_2-C_{10})$alkynyl, Br, F, I, OH, $O(C_1-C_{10})$alkylene-NHCO$(C_1-C_{10})$alkylene-$(C_5-C_{10})$heterocycloalkyl or $O(C_1-C_{10})$alkylene-NH—CS—NH—R" with R" being:

wherein:
R" and the $(C_5-C_{10})$heterocycloalkyl group are optionally substituted by OH or =O;
or $R_2$ forms with $R_3$ together with the carbon atoms to which $R_2$ and $R_3$ are attached to form a $(C_6-C_{10})$aryl.

10. The method of claim 6, wherein $R_3$ is H, $(C_1-C_{10})$alkoxyl or $R_3$ forms with $R_2$ together with the carbon atoms to which $R_3$ and $R_2$ are attached to form a $(C_6-C_{10})$aryl.

11. The method of claim 6, wherein $R_4$ is H, halogen or $(C_1-C_{10})$alkoxyl.

12. The method of claim 6, wherein $R_5$ is a possibly substituted phenyl or a tetrahydropyranyl group.

13. A compound having the following formula (i):

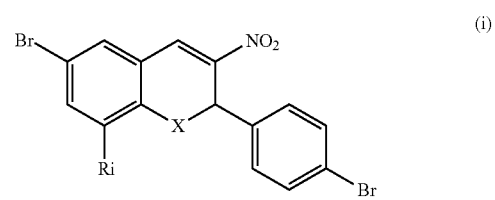

wherein X is O or S and Ri is selected from the group consisting of H, $(C_1-C_{10})$alkyl, $(C_1-C_{10})$alkoxyl, $(C_2-C_{10})$alkenyl, $(C_2-C_{10})$alkynyl, OH, a fluorine atom, a bromine atom and a iodine atom;

or its pharmaceutically acceptable salts, hydrates or hydrated salts or its polymorphic crystalline structures, racemates, diastereomers or enantiomers.

14. The compound according to claim 13, where Ri is selected from the group consisting of H, a fluorine atom, a bromine atom or a iodine atom.

* * * * *

UNITED STATES PATENT AND TRADEMARK OFFICE
CERTIFICATE OF CORRECTION

PATENT NO. : 9,656,984 B2
APPLICATION NO. : 15/025086
DATED : May 23, 2017
INVENTOR(S) : Mickael Jean et al.

It is certified that error appears in the above-identified patent and that said Letters Patent is hereby corrected as shown below:

On the Title Page

Item (54) Title of Invention:
"PI3K/AKT/MTOR INHIBITORS AND PHARMACEUTICAL USES THEREOF" should read
-- NEW PI3K/AKT/MTOR INHIBITORS AND PHARMACEUTICAL USES THEREOF --

Signed and Sealed this
Seventh Day of November, 2017

Joseph Matal
*Performing the Functions and Duties of the*
*Under Secretary of Commerce for Intellectual Property and*
*Director of the United States Patent and Trademark Office*